US010138253B2

(12) United States Patent
Kadow et al.

(10) Patent No.: US 10,138,253 B2
(45) Date of Patent: Nov. 27, 2018

(54) IMIDAZOPYRIDINE MACROCYCLES AS INHIBITORS OF HUMAN IMMUNODEFICIENCY VIRUS REPLICATION

(71) Applicant: ViiV Healthcare UK (No.5) Limited, Brentford, Middlesex (GB)

(72) Inventors: John F. Kadow, Wallingford, CT (US); B. Narasimhulu Naidu, Wallingford, CT (US); Manoj Patel, Wallingford, CT (US); Kevin Peese, Wallingford, CT (US); Zhongyu Wang, Wallingford, CT (US)

(73) Assignee: ViiV HEALTHCARE UK (NO.5) LIMITED, Brentford, Middlesex (GB)

(*) Notice: Subject to any disclaimer, the term of this patent is extended or adjusted under 35 U.S.C. 154(b) by 0 days.

(21) Appl. No.: 15/749,158

(22) PCT Filed: Aug. 10, 2016

(86) PCT No.: PCT/IB2016/054827
§ 371 (c)(1),
(2) Date: Jan. 31, 2018

(87) PCT Pub. No.: WO2017/025913
PCT Pub. Date: Feb. 16, 2017

(65) Prior Publication Data

US 2018/0230165 A1 Aug. 16, 2018

Related U.S. Application Data

(60) Provisional application No. 62/202,973, filed on Aug. 10, 2015.

(51) Int. Cl.

| | |
|---|---|
| ***C07D 471/04*** | (2006.01) |
| ***C07D 498/22*** | (2006.01) |
| ***A61K 31/437*** | (2006.01) |
| ***C07D 498/16*** | (2006.01) |
| ***C07D 498/06*** | (2006.01) |
| ***A61P 31/18*** | (2006.01) |
| *A61K 31/4985* | (2006.01) |

(52) U.S. Cl.
CPC ............ *C07D 498/16* (2013.01); *A61P 31/18* (2018.01); *C07D 498/06* (2013.01); *A61K 31/4985* (2013.01)

(58) Field of Classification Search
USPC ............................ 546/26, 121; 514/279, 300
See application file for complete search history.

(56) References Cited

U.S. PATENT DOCUMENTS 9,409,922 B2 * 8/2016 Peese .................. C07D 471/04

FOREIGN PATENT DOCUMENTS

| | | |
|---|---|---|
| WO | WO 2014/028384 A1 | 2/2014 |
| WO | WO 2014/159959 A1 | 10/2014 |
| WO | WO 2014/164409 A1 | 10/2014 |
| WO | WO 2015/126751 A1 | 8/2015 |

* cited by examiner

*Primary Examiner* — Charanjit Aulakh
(74) *Attorney, Agent, or Firm* — Robert H. Brink; Edward R. Gimmi; William R. Majarian

(57) ABSTRACT

Disclosed are compounds of Formula I, including pharmaceutically acceptable salts, pharmaceutical compositions comprising the compounds, methods for making the compounds and their use in inhibiting HIV integrase and treating those infected with HIV or AIDS.

I

9 Claims, No Drawings

IMIDAZOPYRIDINE MACROCYCLES AS INHIBITORS OF HUMAN IMMUNODEFICIENCY VIRUS REPLICATION

CROSS REFERENCE TO RELATED INVENTION

This application is a § 371 of International Application No. PCT/IB2016/054827, filed 10 Aug. 2016, which claims the benefit of U.S. Provisional Application No. 62/202,973, filed 10 Aug. 2015.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that an estimated 35.3 million people worldwide are infected with the virus (UNAIDS: Report on the Global HIV/AIDS Epidemic, 2013). In addition to the large number of individuals already infected, the virus continues to spread. Estimates from 2013 point to close to 3.4 million new infections in that year alone. In the same year there were approximately 1.6 million deaths associated with HIV and AIDS.

Current therapy for HIV-infected individuals consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity, i.e., cobicistat, available from Gilead Sciences, Inc. under the tradename TYBOST™ (cobicistat) tablets, has recently been approved for use in combinations with certain antiretroviral agents (ARVs) that may benefit from boosting.

In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See, for example, the following patent applications: WO2007131350, WO2009062285, WO2009062288, WO2009062289, WO2009062308, WO2010130034, WO2010130842, WO2011015641, WO2011076765, WO2012033735, WO2013123148, WO2013134113, WO2014164467, WO2014159959, and WO2015126726.

What is now needed in the art are additional compounds which are novel and useful in the treatment of HIV. Additionally, these compounds may desireably provide advantages for pharmaceutical uses, for example, with regard to one or more of their mechanisms of action, binding, inhibition efficacy, target selectivity, solubility, safety profiles, or bioavailability. Also needed are new formulations and methods of treatment which utilize these compounds.

SUMMARY OF THE INVENTION

The invention encompasses compounds of Formula I, including pharmaceutically acceptable salts thereof, as well as pharmaceutical compositions, and their use in inhibiting HIV and treating those infected with HIV or AIDS.

By virtue of the present invention, it is now possible to provide compounds that are novel and are useful in the treatment of HIV. Additionally, the compounds may provide advantages for pharmaceutical uses, for example, with regard to one or more of their mechanism of action, binding, inhibition efficacy, target selectivity, solubility, safety profiles, or bioavailability.

The invention also provides pharmaceutical compositions comprising the compounds of the invention, including pharmaceutically acceptable salts thereof, and a pharmaceutically acceptable carrier, excipient, and/or diluent.

In addition, the invention provides methods of treating HIV infection comprising administering a therapeutically effective amount of the compounds of the invention to a patient.

In addition, the invention provides methods for inhibiting HIV integrase.

Also provided in accordance with the invention are methods for making the compounds of the invention.

The present invention is directed to these, as well as other important ends, hereinafter described.

DESCRIPTION OF THE INVENTION

Unless specified otherwise, these terms have the following meanings.

"Alkyl" means a straight or branched saturated hydrocarbon comprised of 1 to 10 carbons, and preferably 1 to 6 carbons.

"Alkenyl" means a straight or branched alkyl group comprised of 2 to 10 carbons with at least one double bond and optionally substituted with 0-3 halo or alkoxy group.

"Alkynyl" means a straight or branched alkyl group comprised of 2 to 10 carbons, preferably 2 to 6 carbons, containing at least one triple bond and optionally substituted with 0-3 halo or alkoxy group.

"Aryl" mean a carbocyclic group comprised of 1-3 rings that are fused and/or bonded and at least one or a combination of which is aromatic. The non-aromatic carbocyclic portion, where present, will be comprised of $C_3$ to $C_7$ alkyl group. Examples of aromatic groups include, but are not limited to indanyl, indenyl, naphthyl, phenyl, tetrahydronaphthyl and cyclopropylphenyl. The aryl group can be attached to the parent structure through any substitutable carbon atom in the group.

"Arylalkyl" is a $C_1$-$C_5$ alkyl group attached to 1 to 2 aryl groups and linked to the parent structure through the alkyl moiety. Examples include, but are not limited to, —$(CH_2)_n$Ph with n=1-5, —$CH(CH_3)$Ph, —$CH(Ph)_2$.

"Aryloxy" is an aryl group attached to the parent structure by oxygen.

"Cycloalkyl" means a monocyclic ring system composed of 3 to 7 carbons.

"Halo" includes fluoro, chloro, bromo, and iodo.

"Haloalkyl" and "haloalkoxy" include all halogenated isomers from monohalo to perhalo.

"Heteroaryl" is a subset of heterocyclic group as defined below and is comprised of 1-3 rings where at least one or a combination of which is aromatic and that the aromatic group contains at least one atom chosen from a group of oxygen, nitrogen or sulfur.

"Heterocyclyl or heterocyclic" means a cyclic group of 1-3 rings comprised of carbon and at least one other atom selected independently from oxygen, nitrogen and sulfur. The rings could be bridged, fused and/or bonded, through a direct or spiro attachment, with the option to have one or a combination thereof be aromatic. Examples include, but are not limited to, azaindole, azaindoline, azetidine, benzimidazole, bezodioxolyl, benzoisothiazole, benzothiazole, benzothiadiazole, benzothiophene, benzoxazole, carbazole, chroman, dihalobezodioxolyl, dihydrobenzofuran, dihydrobenzo[1,4]oxazine, 1,3-dihydrobenzo[c]thiophene 2,2-dioxide, 2,3-dihydrobenzo[d]isothiazole 1,1-dioxide, 3,4-dihydro-2H-pyrido[3,2-b][1,4]oxazine, 2,3-dihydro-1H-pyrrolo[3,4-c]pyridine and its regioisomeric variants, 6,7-dihydro-5H-pyrrolo[2,3-b]pyrazine and its regioisomeric variants, furanylphenyl, imidazole, imidazo[1,2-a]pyridine, indazole, indole, indoline, isoquinoline, isoquinolinone, isothiazolidine 1,1-dioxide, morpholine, 2-oxa-5-azabicyclo[2.2.1]heptane, oxadiazole-phenyl, oxazole, phenylaztidine, phenylindazole, phenylpiperidine, phenylpiperizine, phenyloxazole, phenylpyrrolidine, piperidine, pyridine, pyridinylphenyl, pyridinylpyrrolidine, pyrimidine, pyrimidinylphenyl, pyrrazole-phenyl, pyrrolidine, pyrrolidin-2-one, 1H-pyrazolo[4,3-c]pyridine and its regioisomeric variants, pyrrole, 5H-pyrrolo[2,3-b]pyrazine, 7H-pyrrolo[2,3-d]pyrimidine and its regioisomeric variants, quinazoline, quinoline, quinoxaline, tetrahydroisoquinoline, 1,2,3,4-tetrahydro-1,8-naphthyridine, tetrahydroquinoline, 4,5,6,7-tetrahydrothieno[3,2-c]pyridine, 1,2,5-thiadiazolidine 1,1-dioxide, thiophene, thiophenylphenyl, triazole, or triazolone. Unless otherwise specifically set forth, the heterocyclic group can be attached to the parent structure through any suitable atom in the group that results in a stable compound.

It is understood that a subset of the noted heterocyclic examples encompass regioisomers. For instance, "azaindole" refers to any of the following regioisomers: 1H-pyrrolo[2,3-b]pyridine, 1H-pyrrolo[2,3-c]pyridine, 1H-pyrrolo[3,2-c]pyridine, and 1H-pyrrolo[3,2-b]pyridine. In addition the "regioisomer variants" notation as in, for example, "5H-pyrrolo[2,3-b]pyrazine and its regioisomeric variants" would also encompass 7H-pyrrolo[2,3-d]pyrimidine, 7H-pyrrolo[2,3-c]pyridazine, 1H-pyrrolo[2,3-d]pyridazine, 5H-pyrrolo[3,2-c]pyridazine, and 5H-pyrrolo[3,2-d]pyrimidine. Similarly, 6,7-dihydro-5H-pyrrolo[2,3-b]pyrazine and its regioisomeric variants would encompass 6,7-dihydro-5H-pyrrolo[2,3-d]pyrimidine and 6,7-dihydro-5H-pyrrolo[2,3-c]pyridazine. It is also understood that the lack of "regioisomeric variants" notation does not in any way restrict the claim scope to the noted example only.

"Heterocyclylalkyl" is a heterocyclyl moiety attached to the parent structure through $C_1$-$C_5$ alkyl group. Examples include, but are not limited to, —$(CH_2)$—$R^Z$ or —$CH(CH_3)$—$(R^Z)$ where n=1-5 and that $R^Z$ is chosen from benzimidazole, imidazole, indazole, isooxazole, phenyl-pyrazole, pyridine, quinoline, thiazole, triazole, triazolone, oxadiazole.

Terms with a hydrocarbon moiety (e.g. alkoxy) include straight and branched isomers for the hydrocarbon portion with the indicated number of carbon atoms.

Bonding and positional bonding relationships are those that are stable as understood by practitioners of organic chemistry.

Parenthetic and multiparenthetic terms are intended to clarify bonding relationships to those skilled in the art. For example, a term such as ((R)alkyl) means an alkyl substituent further substituted with the substituent R.

Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

"Combination," "coadministration," "concurrent" and similar terms referring to the administration of a compound of Formula I with at least one anti-HIV agent mean that the components are part of a combination antiretroviral therapy or highly active antiretroviral therapy ("HAART") as understood by practitioners in the field of AIDS and HIV infection.

"Therapeutically effective" means the amount of agent required to provide a benefit to a patient as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus.

"Treatment," "therapy," "regimen," "HIV infection," "ARC," "AIDS" and related terms are used as understood by practitioners in the field of AIDS and HIV infection.

Those terms not specifically set forth herein shall have the meaning which is commonly understood and accepted in the art.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

In an aspect of the invention, there is provided a compound of Formula I:

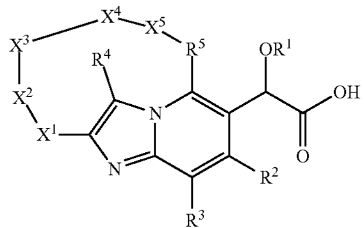

wherein:

$R^1$ is selected from hydrogen or alkyl;

$R^2$ is selected from hydrogen or alkyl;

$R^3$ is selected from hydrogen, cyano, halo, alkyl, hydroxyalkyl, alkoxyalkyl, ($Ar^1$)alkyl, or alkenyl;

$R^4$ is selected from hydrogen, halo, or alkyl;

$R^5$ is selected from azetidinyl, pyrrolidinyl, piperidinyl, piperazinyl, morpholinyl, homopiperidinyl, homopiperazinyl, or homomorpholinyl substituted with 0-3 substituents selected from halo, alkyl, haloalkyl, hydroxy, alkoxy, and haloalkoxy;

$Ar^1$ is selected from pyrazolyl or triazolyl;

$X^1$ is phenyl substituted with 0-3 substituents selected from cyano, halo, alkyl, haloalkyl, alkoxy, and haloalkoxy;

$X^2$ is phenyl substituted with 0-3 substituents selected from cyano, halo, alkyl, haloalkyl, alkoxy, and haloalkoxy;

$X^3$ is —O—;

$X^4$ is alkyleneoxyalkylene; and $X^5$ is —O—;

or a pharmaceutically acceptable salt thereof.

In an aspect of the invention, $R^1$ is alkyl.

In an aspect of the invention, $R^2$ is alkyl.

In an aspect of the invention, $R^3$ is selected from cyano, hydroxyalkyl, alkoxyalkyl, ($Ar^1$)alkyl, or alkenyl.

In an aspect of the invention, $R^4$ is selected from hydrogen or halo.

In an aspect of the invention, $R^5$ is piperidinyl substituted with 0-3 substituents selected from halo, alkyl, haloalkyl, hydroxy, alkoxy, and haloalkoxy.

In an aspect of the invention, $R^1$ and alkyl $R^2$ are alkyl; and $R^5$ is piperidinyl substituted with 0-3 substituents selected from halo, alkyl, haloalkyl, hydroxy, alkoxy, and haloalkoxy;

In an aspect of the invention, there is provided a compound of Formula I:

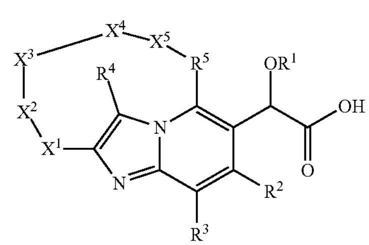

wherein:

$R^1$ is alkyl;

$R^2$ is alkyl;

$R^3$ is selected from hydrogen, cyano, halo, alkyl, hydroxyalkyl, alkoxyalkyl, ($Ar^1$)alkyl, or alkenyl;

$R^4$ is selected from hydrogen, halo, or alkyl;

$R^5$ is piperidinyl substituted with 0-3 substituents selected from halo, alkyl, haloalkyl, hydroxy, alkoxy, and haloalkoxy;

$Ar^1$ is selected from pyrazolyl or triazolyl;

$X^1$ is phenyl substituted with 0-3 substituents selected from cyano, halo, alkyl, haloalkyl, alkoxy, and haloalkoxy;

$X^2$ is phenyl substituted with 0-3 substituents selected from cyano, halo, alkyl, haloalkyl, alkoxy, and haloalkoxy;

$X^3$ is —O—;

$X^4$ is alkyleneoxyalkylene; and $X^5$ is —O—;

or a pharmaceutically acceptable salt thereof.

In an aspect of the invention, there is provided a compound of Formula I:

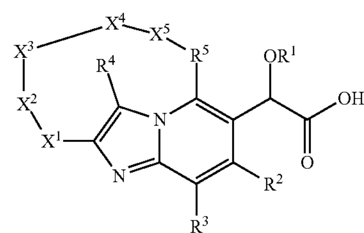

wherein:

$R^1$ is selected from hydrogen or alkyl;

$R^2$ is selected from hydrogen or alkyl;

$R^3$ is selected from cyano, hydroxyalkyl, alkoxyalkyl, ($Ar^1$) alkyl, or alkenyl;

$R^4$ is selected from hydrogen, halo, or alkyl;

$R^5$ is piperidinyl substituted with 0-3 substituents selected from halo, alkyl, haloalkyl, hydroxy, alkoxy, and haloalkoxy;

$Ar^1$ is selected from pyrazolyl or triazolyl;

$X^1$ is phenyl substituted with 0-3 substituents selected from cyano, halo, alkyl, haloalkyl, alkoxy, and haloalkoxy;

$X^2$ is phenyl substituted with 0-3 substituents selected from cyano, halo, alkyl, haloalkyl, alkoxy, and haloalkoxy;

$X^3$ is —O—;

$X^4$ is alkyleneoxyalkylene; and $X^5$ is —O—;

or a pharmaceutically acceptable salt thereof.

For a particular compound of Formula I, the scope of any instance of a variable substituent, including $R^1$, $R^2$, $R^3$, $R^4$, $R^5$, $Ar^1$, $X^1$, $X^2$, $X^3$, $X^4$ and $X^5$ can be used independently with the scope of any other instance of a variable substituent. As such, the invention includes combinations of the different aspects.

In an aspect of the invention, there is provided a composition useful for treating HIV infection comprising a therapeutic amount of a compound of Formula I and a pharmaceutically acceptable carrier. In an aspect of the invention, the composition further comprises a therapeutically effective amount at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier. In an aspect of the invention, the other agent is dolutegravir.

In an aspect of the invention, there is provided a method for treating HIV infection comprising administering a therapeutically effective amount of a compound of Formula I, or a pharmaceutically acceptable salt thereof, to a patient in need thereof. In an aspect of the invention, the method further comprises administering a therapeutically effective amount of at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors. In an aspect of the invention, the other agent is dolutegravir. In an aspect of the invention, the other agent is administered to the patient prior to, simultaneously with, or subsequently to the compound of Formula I.

Preferred compounds in accordance with the present invention include the following:

(2S)-2-(tert-Butoxy)-2-[(22S)-17,18-difluoro-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-17,18-difluoro-4,5,22,28-tetramethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2R)-2-(tert-Butoxy)-2-((6S,Z)-44,45-difluoro-14,27,6-trimethyl-5,8,11-trioxa-2(5,2)-imidazo[1,2-a]pyridina-1(1,4)-piperidina-3(1,3),4(1,2)-dibenzenacycloundecaphane-26-yl)acetic acid;

(2S)-2-[(22S)-17,18-Difluoro-4,5,22,28-tetramethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]-2-[(2-methylbutan-2-yl)oxy]acetic acid;

(2S)-2-[(22S)-17,18-Difluoro-4,5,22,28-tetramethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34), 8,10(33),11,13,15(20),16,18-decaen-3-yl]-2-hydroxyacetic acid;

(2S)-2-(tert-Butoxy)-2-[(22S)-17,18-difluoro-5-(hydroxymethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-8-chloro-17,18-difluoro-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-8-chloro-17,18-difluoro-4,5,22,28-tetramethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-8-chloro-17,18-difluoro-5-(hydroxymethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-8-chloro-17,18-difluoro-4,22,28-trimethyl-5-(1H-pyrazol-1-ylmethyl)-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-8-chloro-17,18-difluoro-5-(methoxymethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-8-chloro-17,18-difluoro-4,22,28-trimethyl-5-(1H-1,2,3-triazol-1-ylmethyl)-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-8-chloro-17,18-difluoro-4,22,28-trimethyl-5-(2H-1,2,3-triazol-2-ylmethyl)-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-17,18-difluoro-4,22,28-trimethyl-5-(prop-1-en-2-yl)-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-17,18-difluoro-4,5,8,22,28-pentamethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-17,18-difluoro-5-(1-hydroxyethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-5-cyano-17,18-difluoro-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen3-yl]acetic acid;

(2S)-2-(tert-Butoxy)-2-[(22S)-16-fluoro-4,18,22,28-tetramethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-((6S,Z)-46-fluoro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetic acid;

(2S)-2-(tert-Butoxy)-2-((6S,Z)-46-fluoro-28-(hydroxymethyl)-14,27,44,6-tetramethyl-5,8,11-trioxa-2(5,2)-imidazo[1,2-a]pyridina-1(1,4)-piperidina-3(1,3),4(1,2)-dibenzenacycloundecaphane-26-yl)acetic acid;

(2S)-2-(tert-Butoxy)-2-((6S,E)-23-chloro-46-fluoro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetic acid;

(2S)-2-(tert-Butoxy)-2-[(22S)-4,18,22,28-tetramethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-((6S,Z)-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetic acid;

(2S)-2-(tert-Butoxy)-2-((6S,E)-23-chloro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetic acid;

(2S)-2-(tert-Butoxy)-2-[(22S)-4,17,22,28-tetramethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-4,5,17,22,28-pentamethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-[(22S)-8-chloro-4,5,17,22,28-pentamethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid;

(2S)-2-(tert-Butoxy)-2-((6S,Z)-45-fluoro-14,27,28,6-tetramethyl-5,8,11-trioxa-2(5,2)-imidazo[1,2-a]pyridina-1(1,4)-piperidina-3(1,3),4(1,2)-dibenzenacycloundecaphane-26-yl)acetic acid;

(2S)-2-(tert-Butoxy)-2-((6S,E)-23-chloro-45-fluoro-14,27,28,6-tetramethyl-5,8,11-trioxa-2(5,2)-imidazo[1,2-a]pyridina-1(1,4)-piperidina-3(1,3),4(1,2)-dibenzenacycloundecaphane-26-yl)acetic acid; and pharmaceutically acceptable salts thereof.

The compounds of the invention herein described may typically be administered as pharmaceutical compositions. These compositions are comprised of a therapeutically effective amount of a compound of Formula I or its pharmaceutically acceptable salt, and a pharmaceutically acceptable carrier and may contain conventional excipients and/or diluents. A therapeutically effective amount is that which is needed to provide a meaningful patient benefit. Pharmaceutically acceptable carriers are those conventionally known carriers having acceptable safety profiles. Compositions encompass all common solid and liquid forms, including capsules, tablets, lozenges, and powders, as well as liquid suspensions, syrups, elixirs, and solutions. Compositions are made using available formulation techniques, and excipients (such as binding and wetting agents) and vehicles (such as water and alcohols) which are generally used for compositions. See, for example, Remington's Pharmaceutical Sciences, 17th edition, Mack Publishing Company, Easton, Pa. (1985).

Solid compositions which are normally formulated in dosage units and compositions providing from about 1 to 1000 milligram ("mg") of the active ingredient per dose are typical. Some examples of dosages are 1 mg, 10 mg, 100 mg, 250 mg, 500 mg, and 1000 mg. Generally, other antiretroviral agents will be present in a unit range similar to agents of that class used clinically. Typically, this is about 0.25-1000 mg/unit.

Liquid compositions are usually in dosage unit ranges. Generally, the liquid composition will be in a unit dosage range of about 1-100 milligram per milliliter ("mg/mL"). Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is about 1-100 mg/mL.

The invention encompasses all conventional modes of administration; oral and parenteral methods are preferred. Generally, the dosing regimen will be similar to other antiretroviral agents used clinically. Typically, the daily dose will be about 1-100 milligram per kilogram ("mg/kg") body weight daily. Generally, more compound is required orally and less parenterally. The specific dosing regimen, however, will be determined by a physician using sound medical judgment.

The compounds of this invention desireably have activity against HIV. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier, excipient and/or diluent.

The invention also encompasses methods where the compound is given in combination therapy. That is, the compound can be used in conjunction with, but separately from, other agents useful in treating AIDS and HIV infection. The compound can also be used in combination therapy wherein the compound and one or more of the other agents are physically together in a fixed-dose combination (FDC). Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, HIV capsid inhibitors, anti-infectives, and immunomodulators, such as, for example, PD-1 inhibitors, PD-L1 inhinitors, antibodies, and the like. In these combination methods, the compound of Formula I will generally be given in a daily dose of about 1-100 mg/kg body weight daily in conjunction with other agents. The other agents generally will be given in the amounts used therapeutically. The specific dosing regimen, however, will be determined by a physician using sound medical judgment.

Examples of nucleoside HIV reverse transcriptase inhibitors include abacavir, didanosine, emtricitabine, lamivudine, stavudine, tenofovir, zalcitabine, and zidovudine.

Examples of non-nucleoside HIV reverse transcriptase inhibitors include delavirdine, efavirenz, etrivirine, nevirapine, and rilpivirine.

Examples of HIV protease inhibitors include amprenavir, atazanavir, darunavir, fosamprenavir, indinavir, lopinavir, nelfinavir, ritonavir, saquinavir and, tipranavir.

An example of an HIV fusion inhibitor is enfuvirtide or T-1249.

An example of an HIV entry inhibitor is maraviroc.

Examples of HIV integrase inhibitors include dolutegravir, elvitegravir, or raltegravir.

An example of an HIV attachment inhibitor is fostemsavir.

An example of an HIV maturation inhibitor is BMS-955176, having the following structure:

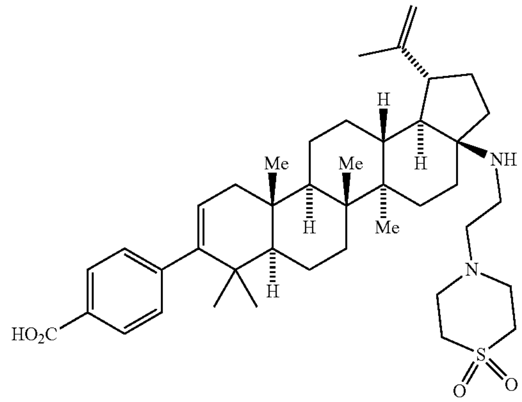

Thus, as set forth above, contemplated herein are combinations of the compounds of Formula I, together with one or more agents useful in the treatment of AIDS. For example, the compounds of the invention may be effectively administered, whether at periods of pre-exposure and/or post-exposure, in combination with effective amounts of the AIDS antivirals, immunomodulators, anti-infectives, or vaccines, such as those in the following non-limiting table:

| Drug Name | Manufacturer | Indication |
|---|---|---|
| | ANTIVIRALS | |
| Rilpivirine | Tibotec | HIV infection, AIDS, ARC (non-nucleoside reverse transcriptase inhibitor) |
| COMPLERA ® | Gilead | HIV infection, AIDS, ARC; combination with emtricitabine, rilpivirine, and tenofovir disoproxil fumarate |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences Ethigen | HIV infection ARC, PGL |
| AL-721 | (Los Angeles, CA) | HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |

-continued

| Drug Name | Manufacturer | Indication |
|---|---|---|
| Cytovene Ganciclovir | Syntex | Sight threatening CMV peripheral CMV retinitis |
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoromethyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |

-continued

| Drug Name | Manufacturer | Indication |
|---|---|---|
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ™ Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® | Oncolys BioPharma | HIV infection AIDs in development |
| CMX-157 Lipid conjugate of nucleotide tenofovir | Chimerix | HIV infection AIDs |
| GSK1349572 Integrase inhibitor TIVICAY ® dolutegravir | GSK | HIV infection AIDS |
| | IMMUNOMODULATORS | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |

-continued

| Drug Name | Manufacturer | Indication |
|---|---|---|
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| | ANTI-INFECTIVES | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc diarrhea | Cryptosporidial |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Methods of Synthesis

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potasium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "$Et_2O$" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds of this invention can be prepared by the methods outlined in the Scheme I.

Scheme I

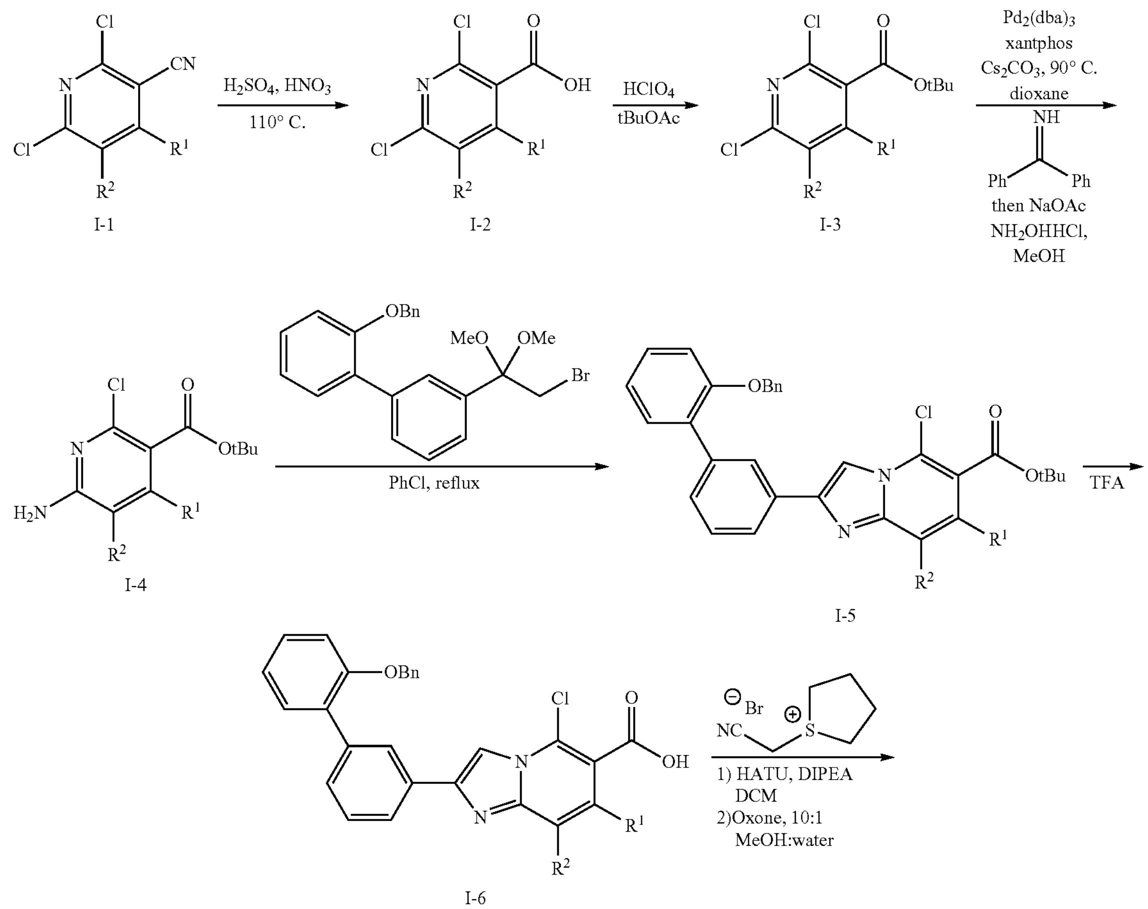

-continued
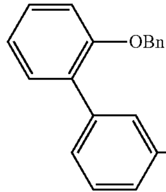
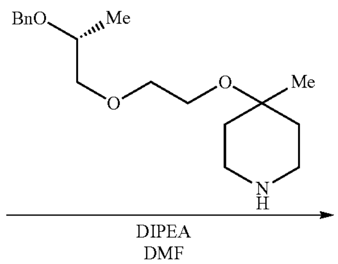
DIPEA
DMF
I-7
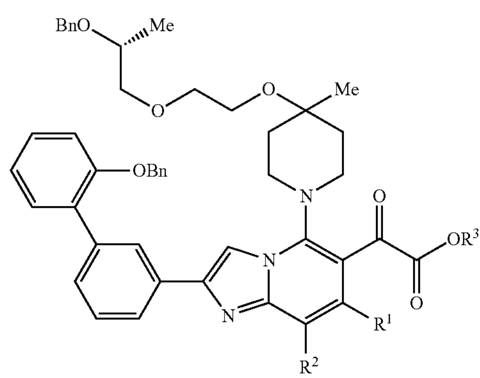
(R)—CBS
catecholborane
toluene, -20° C.
I-8
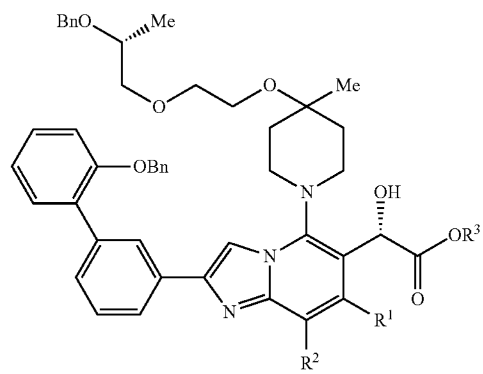
HCl
$O_4$
tBu
OAc
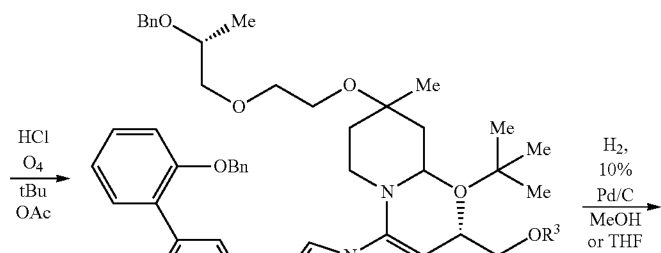
$H_2$,
10%
Pd/C
MeOH
or THF
I-9
I-10
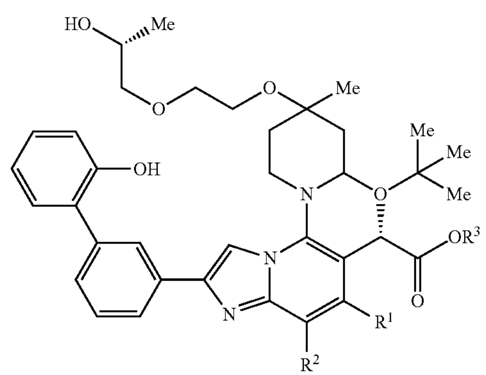
1. DIAD,
2. LiOH
$PPh_3$
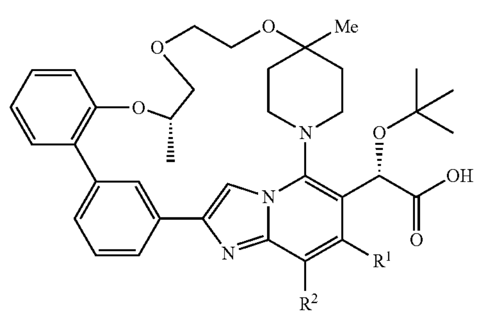
I-12
I-11

Some compounds of this invention can be prepared by the methods outlined in the Scheme II.
Scheme II
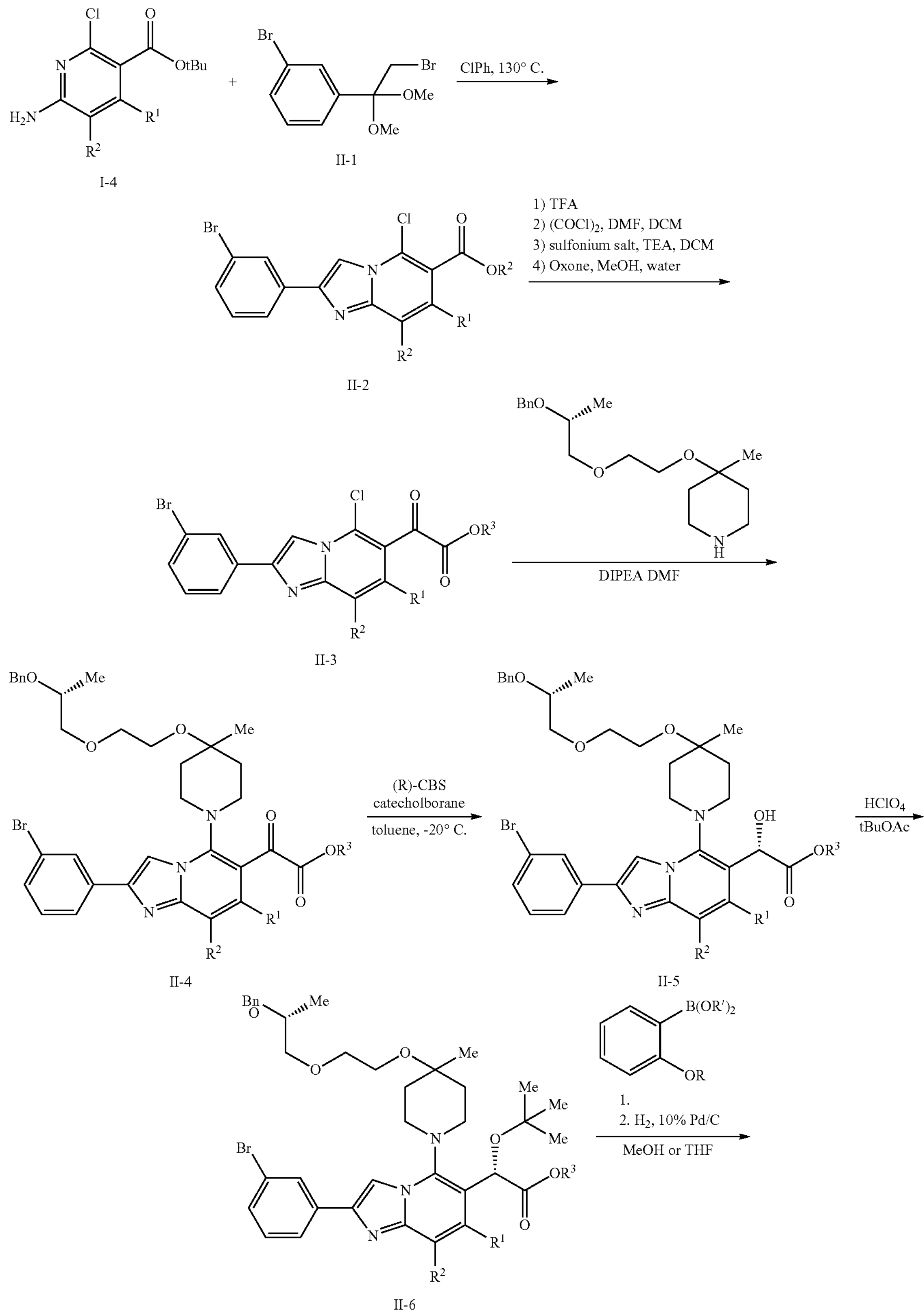

-continued

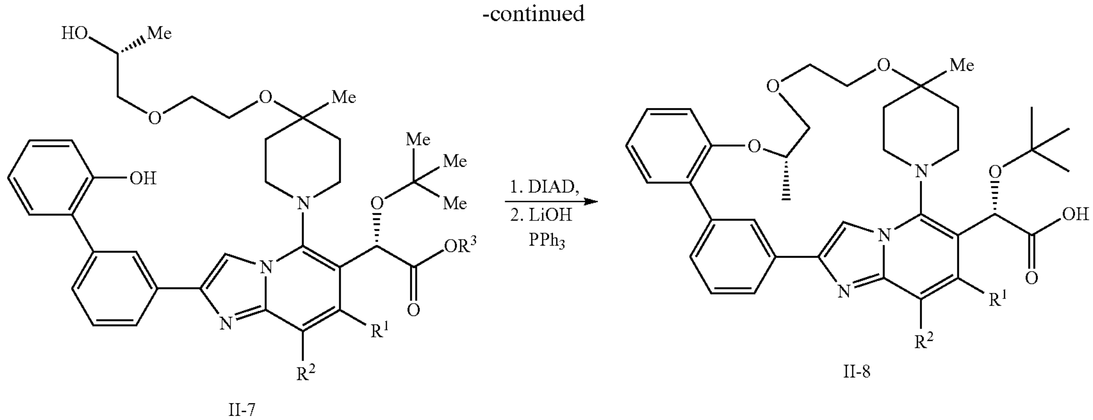

The compounds described herein were purified by the methods well known to those skilled in art by normal phase column chromatography on silica gel column using appropriate solvent system described. Preparative HPLC purifications mentioned in this experimentation section were carried out gradient elution either on Sunfire Prep C18 ODB column (5 μm; 19 or 30×100 mm) or Waters Xbridge C18 column (5 μM; 19×200 or 30×100 mm) or Water Atlantis (5 μm; 19 or 30×100 mm) using the following mobile phases. Mobile phase A: 9:1 $H_2O$/acetonitrile with 10 mM $NH_4OAc$ and mobile phase B:A: 9:1 acetonitrile/$H_2O$ with 10 mM $NH_4OAc$; or mobile phase A: 9:1 $H_2O$/acetonitrile with 0.1% TFA and mobile phase B:A: 9:1 acetonitrile/$H_2O$ with 0.1% TFA; or mobile phase A: water/MeOH (9:1) with 20 mM $NH_4OAc$ and mobile phase B: 95:5 MeOH/$H_2O$ with 20 mM $NH_4OAc$ or mobile phase A:water/MeOH (9:1) with 0.1% TFA and mobile phase B: 95:5 MeOH/$H_2O$ with 0.1% TFA or mobile Phase A: 5:95 acetonitrile:water with 10-mM ammonium acetate; Mobile Phase B: 95:5 acetonitrile:water with 10-mM ammonium acetate.

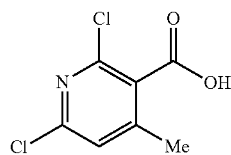 [SMILES: Cc1cc(Cl)nc(Cl)c1C(=O)O]

2,6-dichloro-4-methylnicotinic Acid

Prepared from commercially available 2,6-dichloro-4-methylnicotinonitrile following procedure in U.S. Pat. No. 6,677,352 (2004).

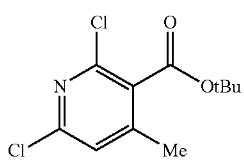 [SMILES: Cc1cc(Cl)nc(Cl)c1C(=O)OC(C)(C)C]

tert-butyl 2,6-dichloro-4-methylnicotinate

To a solution of 2,6-dichloro-4-methylnicotinic acid (1.00 g, 4.85 mmol, 1 equiv) in tert-butyl acetate (24 mL) was added 70% perchloric acid (0.88 mL, 14.56 mmol, 3 equiv). After 1 h, reaction was diluted with DCM, washed cautiously with saturated aqueous sodium bicarbonate solution, dried ($Na_2SO_4$), and concentrated in vacuo to provide the product (1.21 g, 95%) as a pale yellow oil. $^1$H NMR (400 MHz, $CDCl_3$) δ 7.15 (s, 1H), 2.37 (d, J=0.5 Hz, 3H), 1.62 (s, 9H); LCMS (ESI, M+1): 262.1.

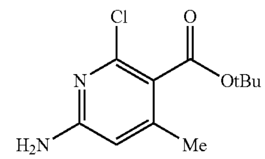 [SMILES: Cc1cc(N)nc(Cl)c1C(=O)OC(C)(C)C]

tert-butyl 6-amino-2-chloro-4-methylnicotinate tert-butyl 2,6-dichloro-4-methylnicotinate (10.5 g, 40.1 mmol, 1 equiv), $Pd_2(dba)_3$ (1.84 g, 2.01 mmol, 0.05 equiv), xantphos (2.32 g, 4.01 mmol, 0.1 equiv), and $Cs_2CO_3$ slurried in dioxane (deoxygenated by bubbling nitrogen through it for 10 min) added. Benzophenone imine (8.0 mL, 48.1 mmol, 1.2 equiv) added and the mixture was heated at 90° C. for 1 h. Upon cooling to ambient temperature, the reaction was diluted with EtOAc and washed with water, dried ($Na_2SO_4$), and concentrated in vacuo. The crude product was taken up in MeOH (200 mL) and NaOAc (9.87, 120 mmol, equiv) and hydroxlamine hydrochloride (5.57 g, 80 mmol, 2 equiv) was added. After 30 min, the reaction was added to 1 N NaOH and extracted with DCM (×2). The combined DCM extracts were dried ($Na_2SO_4$) and concentrated in vacuo. The crude product was purified by flash column chromatography (0-30% EtOAc/hex) to afford tert-butyl 6-amino-2-chloro-4-methylnicotinate (7.5 g, 77%). $^1$H NMR (400 MHz, $CDCl_3$) δ 6.22 (d, J=0.8 Hz, 1H), 4.58 (br. s., 2H), 2.27 (d, J=0.8 Hz, 3H), 1.60 (s, 9H); LCMS (ESI, M+1): 243.1.

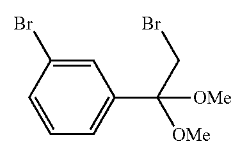 [SMILES: COC(CBr)(OC)c1cccc(Br)c1]

1-Bromo-3-(2-bromo-1,1-dimethoxyethyl)benzene

A solution of 2-bromo-1-(3-bromophenyl)ethanone (48.23 g, 174 mmol) in MeOH (200 ml) was treated with trimethyl orthoformate (57.5 mL) and pTsOH (1.650 g, 8.68 mmol) and heated at reflux (75° C. oil bath) under nitrogen for 2.5 hrs. The mixture was cooled, concentrated to a viscous oil, diluted with $Et_2O$ (250 mL), and washed with 2.0 M aq. $K_2CO_3$ (100 mL), then brine. The organic layer was dried ($MgSO_4$), filtered, and concentrated under reduced pressure, affording the product (56.43 g, 174 mmol, 100% yield) as a mobile yellow oil. $^1$H NMR (500 MHz, $CDCl_3$) δ 7.69 (t, J=1.8 Hz, 1H), 7.48 (ddd, J=7.9, 2.0, 1.0 Hz, 1H), 7.43 (dq, J=7.8, 0.9 Hz, 1H), 7.29-7.24 (m, 2H), 3.60 (s, 2H), 3.24 (s, 6H). $^{13}$C NMR (126 MHz, $CDCl_3$) δ 141.0, 131.5, 130.6, 129.6, 125.9, 122.3, 100.8, 49.5, 35.0. LCMS (M+H-MeOH)=291.97.

tert-Butyl 2-(3-bromophenyl)-5-chloro-7-methylimidazo[1,2-a]pyridine-6-carboxylate A flask charged with chlorobenzene (300 ml) was heated to reflux (140° C. oil bath) and to this was added sequentially 1-bromo-3-(2-bromo-1,1-dimethoxyethyl)benzene (56.05 g, 173 mmol) as an oil, and tert-butyl 6-amino-2-chloro-4-methylnicotinate (33.91 g, 140 mmol) as a powder, rinsing both with additonal chlorobenzene (70 mL total) to facilitate transfer. The reaction was returned to reflux and heated for 90 min, then cooled and poured slowly into vigorously stirred $Et_2O$ (1500 mL). The resulting suspension was stirred for 15 min, then solids were collected by vacuum filtration to afford the product (47 g, 111 mmol, 64.4% yield) as a tan powdery solid. A 3 g sample of product was first purified by biotage (80 g $SiO_2$, 0% (3 CV), 0-60% (15 CV), 60% (2 CV), EtOAc in hexanes), then recrystallized from hot acetonitrile to afford a high purity sample for spectra. $^1$H NMR (500 MHz, $CDCl_3$) δ 8.14 (t, J=1.7 Hz, 1H), 8.02 (d, J=0.5 Hz, 1H), 7.89 (dq, J=7.7, 0.9 Hz, 1H), 7.48 (ddd, J=8.0, 2.0, 1.1 Hz, 1H), 7.41-7.39 (m, 1H), 7.32 (t, J=7.9 Hz, 1H), 2.45 (d, J=0.9 Hz, 3H), 1.65 (s, 9H). $^{13}$C NMR (126 MHz, $CDCl_3$) δ 164.3, 145.6, 145.2, 135.3, 133.6, 131.3, 130.3, 129.2, 124.7, 123.9, 123.0, 121.7, 115.4, 107.6, 83.9, 28.1, 19.9. LCMS (M+H)=421.3.

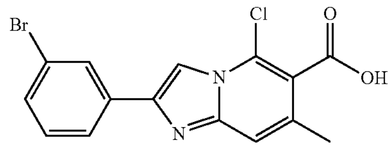 [SMILES: Cc1cc2nc(-c3cccc(Br)c3)cn2c(Cl)c1C(=O)O]

2-(3-Bromophenyl)-5-chloro-7-methylimidazo[1,2-a]pyridine-6-carboxylic Acid, HCl Salt A suspension of tert-butyl 2-(3-bromophenyl)-5-chloro-7-methylimidazo[1,2-a]pyridine-6-carboxylate (35.5 g, 84 mmol) in 4.0 N HCl in dioxane (800 ml) was stirred for 48 hrs. The reaction was concentrated to a thick paste, then the residue was triturated with acetonitrile, collecting solids by vacuum filtration and washing with several small portions of acetonitrile. The reside was resuspended in fresh acetonitrile, stirred for 20 min, then filtered to collect solids. The solids were dried once from $Et_2O$ by rotary evaporator, to afford the product (23.3 g, 58.0 mmol, 68.8% yield) as an off-white powder. $^1$H NMR (500 MHz, DMSO-$d_6$) δ 8.90 (s, 1H), 8.35 (t, J=1.7 Hz, 1H), 8.17-8.08 (m, 1H), 7.73 (s, 1H), 7.67-7.59 (m, 1H), 7.48 (t, J=8.0 Hz, 1H), 2.46 (d, J=0.9 Hz, 3H). $^{13}$C NMR (126 MHz, DMSO-$d_6$) δ 165.9, 143.1, 132.6, 131.7, 129.2, 125.6, 125.1, 125.1, 124.3, 123.0, 113.2, 110.9, 66.8, 20.0. LCMS (M+H)=367.1.

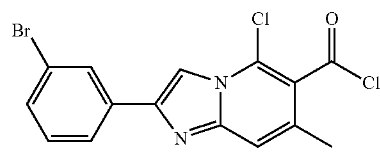 [SMILES: Cc1cc2nc(-c3cccc(Br)c3)cn2c(Cl)c1C(=O)Cl]

2-(3-Bromophenyl)-5-chloro-7-methylimidazo[1,2-a]pyridine-6-carbonyl Chloride

A suspension of 2-(3-bromophenyl)-5-chloro-7-methylimidazo[1,2-a]pyridine-6-carboxylic acid, HCl salt (22.03 g, 60.3 mmol) in dry dichlormethane (600 ml) was treated with oxalyl chloride (13 ml, 149 mmol) followed by DMF (1.5 mL). The suspension was stirred for 3.5 hrs, then concentrated under reduced pressure to afford the acid-chloride as a brown powdery solid which was then used immediately in the following step.

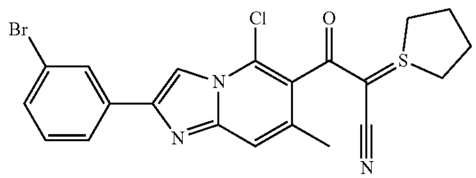 [SMILES: Cc1cc2nc(-c3cccc(Br)c3)cn2c(Cl)c1C(=O)C(C#N)=S1CCCC1]

3-[2-(3-Bromophenyl)-5-chloro-7-methylimidazo[1,2-a]pyridin-6-yl]-3-oxo-2-[(1E)-1λ$^4$-thiolan-1-ylidene]propanenitrile A stirred solution of 2-(3-bromophenyl)-5-chloro-7-methylimidazo[1,2-a]pyridine-6-carbonyl chloride (23.16 g, 60.3 mmol) in dichloromethane (600 ml) was treated with 1-(cyanomethyl)tetrahydro-1H-thiophen-1-ium bromide (18.82 g, 90 mmol) followed by Hunig's Base (31.6 ml, 181 mmol). The reaction was stirred for 16 hrs at room temperature, then the mixture was washed with saturated sodium bicarbonate solution (2×200 mL) and the combined aqueous layer was back extracted (2×50 mL). The combined organic layers were dried ($Na_2SO_4$), filtered, and concentrated under reduced pressure to a reduced volume. The concentrated solution was purified by biotage (330 g $SiO_2$, 10% (3 CV), 10-100% (10 CV), 100% (2 CV), EtOAc in hexanes, then 0% (2 CV), 0-10% (10 CV), 10% (2 CV) MeOH in $CH_2Cl_2$). Product fractions were pooled and concentrated under reduced pressure, affording the product (24.6 g, 51.8 mmol, 86% yield) as a brown glassy solid. This material was used as-is in the following step. Separately, a small sample of column purified product was dissolved in minimal acetonitrile, then further diluted with approximately 4 volumes of $Et_2O$. After 10 min, the resulting crystals were collected by vacuum filtration, washing with $Et_2O$, to afford a higher purity sample for spectra. $^1$H NMR (500 MHz, $CDCl_3$) δ 8.14 (t, J=1.7 Hz, 1H), 8.00 (d, J=0.5 Hz, 1H), 7.92-7.86 (m, 1H), 7.49-7.45 (m, 1H), 7.44-7.39 (m, 1H), 7.36-7.28 (m, 1H), 3.62-3.52 (m, 4H), 2.78-2.67 (m, 2H), 2.42 (d, J=1.1 Hz, 3H), 2.26-2.14 (m, 2H). LCMS (M+H)=476.1.

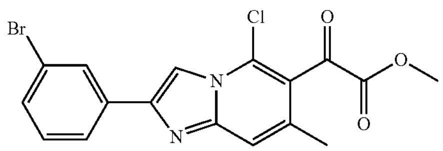 [SMILES: COC(=O)C(=O)c1c(C)cc2nc(-c3cccc(Br)c3)cn2c1Cl]

Methyl 2-(2-(3-bromophenyl)-5-chloro-7-methyl-imidazo[1,2-a]pyridin-6-yl)-2-oxoacetate A suspension of 3-[2-(3-Bromophenyl)-5-chloro-7-methylimidazo[1,2-a]pyridin-6-yl]-3-oxo-2-[(1E)-1$\lambda^4$-thiolan-1-ylidene]propanenitrile (18.92 g, 39.8 mmol) and oxone (39.2 g, 63.8 mmol) in anhydrous MeOH (660 ml) was heated (75° C. oil bath) and stirred exposed to air. Additional oxone (12.25 g, 19.92 mmol) was added after each of 5 hrs and 7.5 hrs respectively. The temperature was reduced (40° C.) and the reaction was stirred for 16 hrs, then warmed again (80° C.) and stirred for 20 hrs. Solids were removed by filtration, and the filtrate was concentrated. The residue was dissolved in EtOAc and washed with water. The organic layer was dried ($MgSO_4$) and concentrated to a small volume. Solids were collected and the filtrate was further concentrated, affording a second crop of solids, both of similar purity, and combined to afford the desired product (9 g, 22.08 mmol, 55.4% yield) as a yellow powdery solid. LCMS (M+H)=409.0.

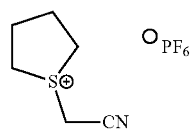

1-(Cyanomethyl)tetrahydro-1H-thiophen-1-ium hexafluorophosphate(V)

To a slurry of 1-(cyanomethyl)tetrahydro-1H-thiophen-1-ium bromide (19.7 g, 95 mmol, 1 equiv) in acetone (316 mL) was added $AgPF_6$ (26.3 g, 104 mmol, 1 equiv). After 15 min, the yellow slurry was filtered. The filtrate was then added slowly to vigorously stirring ether (1.2 L). After 15 min, the white solid was filtered to provide the product (23.7 g, 92%). $^1$H NMR (400 MHz, DMSO-$d_6$) δ 4.63 (s, 2H), 3.71-3.52 (m, 4H), 2.33-2.13 (m, 4H); $^{19}$F NMR (376 MHz, DMSO-$d_6$) δ −70.18 (d, $J_{PF}$=710.9 Hz, 6F).

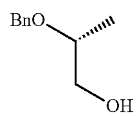

(R)-2-(Benzyloxy)propan-1-ol

To a solution of (R)-2-(benzyloxy)propanoic acid (4.4 g, 24.4 mmol, 1 equiv) in THF (300 mL) at 0° C. was added LAH (1.85 g, 48.8 mmol, 2 equiv). After warming to ambient temperature, the gray slurry was stirred 18 h. The reaction was cooled to 0° C. and water (2 mL) was added dropwise. A solution of 10 M NaOH (0.75 mL) in water (1.25 mL) was then added dropwise followed by slow addition of water (6 mL). After 10 min, the mixture was allowed to warm to ambient temperature and stirred for 4 h. The mixture was the filtered through Celite and the filtrate was concentrated in vacuo to provide the product (4.2 g, 100%) as a pale yellow oil. $^1$H NMR (400 MHz, $CDCl_3$) δ 7.41-7.29 (m, 5H), 4.68 (d, J=11.5 Hz, 1H), 4.51 (d, J=11.5 Hz, 1H), 3.75-3.60 (m, 2H), 3.56-3.49 (m, 1H), 2.04 (dd, J=8.0, 4.5 Hz, 1H), 1.20 (d, J=6.3 Hz, 3H).

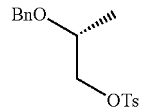

(R)-2-(Benzyloxy)propyl 4-methylbenzenesulfonate

To a solution of (R)-2-(benzyloxy)propan-1-ol (0.86 g, 5.17 mmol, 1 equiv) and TEA (1.5 mL, 10.87 mmol, 2.1 equiv) in DCM (17 mL) was added TsCl (1.18 g, 6.21 mmol, 1.2 equiv). After stirring 18 h, the reaction was washed with saturated sodium bicarbonate, dried ($Na_2SO_4$), and concentrated in vacuo. The crude product was purified via silica gel flash column chromatoraphy (0-30% EtOAc/hexane) to provide the product (1.38 g, 83%) as a viscous colorless oil. $^1$H NMR (400 MHz, $CDCl_3$) δ 7.80 (d, J=8.3 Hz, 2H), 7.39-7.28 (m, 7H), 4.60-4.43 (m, 2H), 4.02 (dd, J=5.0, 3.8 Hz, 2H), 3.78 (td, J=6.2, 4.6 Hz, 1H), 2.45 (s, 3H), 1.18 (d, J=6.3 Hz, 3H).

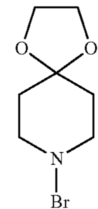

8-Benzyl-1,4-dioxa-8-azaspiro[4.5]decane

To a solution of 1,4-dioxa-8-azaspiro[4.5]decane (5.1 g, 35.6 mmol, 1 equiv) in DMF (71 mL) was added potassium carbonate (9.9 g, 71.2 mmol, 2 equiv) and BnBr (5.1 mL, 42.7 mmol, 1.2 equiv). The resulting pale yellow slurry was stirred for 1 h and then diluted with ether. The ether solution was washed with water, brine, dried ($MgSO_4$), and concentrated in vacuo. The crude product was purified via silica gel flash column chromatoraphy (0-100% EtOAc[2% TEA]/hexane) to provide the product (6.8 g, 82%) as a clear colorless oil. $^1$H NMR (400 MHz, CDCl3) δ 7.35-7.28 (m, 5H), 3.96 (s, 4H), 3.54 (s, 2H), 2.54 (br. s., 4H), 1.76 (t, J=5.6 Hz, 4H).

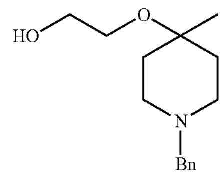 [SMILES: CC1(OCCO)CCN(Cc2ccccc2)CC1]

2-((1-Benzyl-4-methylpiperidin-4-yl)oxy)ethanol

To a solution of 8-benzyl-1,4-dioxa-8-azaspiro[4.5]decane (5.8 g, 24.9 mmol, 1 equiv) in toluene (100 mL) was added MeMgBr (24.9 mL of a 3 M solution in ether, 74.6 mmol, 3 equiv). The reaction was heated slowly to 90° C. allowing the residual ether to boil off. After heating for 4 h, the solution was allowed to cool to ambient temperature. The reaction was added cautiously to saturated aqueous ammonium chloride and extracted with DCM (×3). The combined DCM extractions were dried ($Na_2SO_4$) and concentrated in vacuo. The crude product was purified via silica gel flash column chromatoraphy (30-100% EtOAc[2% TEA]/hexane) to provide the product (4.0 g, 65%) as a pale yellow oil. $^1$H NMR (500 MHz, $CDCl_3$) δ 7.36-7.27 (m, 5H), 3.73 (br. s., 2H), 3.52 (s, 2H), 3.49-3.42 (m, 2H), 2.58-2.49 (m, 2H), 2.41-2.32 (m, 2H), 2.12-2.08 (m, 1H), 1.83-1.76 (m, 2H), 1.65-1.56 (m, 2H), 1.19 (s, 3H); LCMS (ESI, M+1): 250.15.

(R)-1-Benzyl-4-(2-(2-(benzyloxy)propoxy)ethoxy)-4-methylpiperidine

To a solution of 2-((1-benzyl-4-methylpiperidin-4-yl)oxy) ethanol (1.1 g, 4.46 mmol, 1.1 equiv) and (R)-2-(benzyloxy) propyl 4-methylbenzenesulfonate (1.3 g, 4.06 mmol, 1 equiv) in DMF (13.5 mL) was added NaH (0.23 g of a 60% suspension in mineral oil, 5.68 mmol, 1.4 equiv). Gas evolution. After 2 h, the reaction was quenched with water and then partitioned between ether and water. The ether layer was dried ($MgSO_4$) and concentrated in vacuo. The crude product was purified via silica gel flash column chromatography (0-100% EtOAc[2% TEA]/DCM) to provide the product (1.2 g, 76%) as a viscous yellow oil. $^1$H NMR (400 MHz, $CDCl_3$) δ 7.45-7.22 (m, 10H), 4.65 (s, 2H), 3.81-3.45 (m, 9H), 2.50 (d, J=10.8 Hz, 2H), 2.42-2.30 (m, 2H), 1.77 (d, J=13.6 Hz, 2H), 1.59-1.51 (m, 2H), 1.22 (d, J=6.3 Hz, 3H), 1.16 (s, 3H); LCMS (ESI, M+1): 398.25.

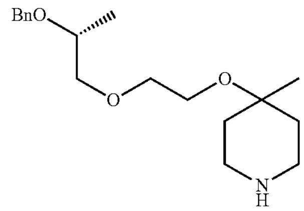 [SMILES: C[C@H](COCCOC1(C)CCNCC1)OCc1ccccc1]

(R)-4-(2-(2-(Benzyloxy)propoxy)ethoxy)-4-methylpiperidine

To a solution of (R)-1-benzyl-4-(2-(2-(benzyloxy) propoxy)ethoxy)-4-methylpiperidine (1.2 g, 3.07 mmol, 1 equiv) in DCE (15 mL) was added 1-chloroethyl chloroformate (1.3 mL, 12.28 mmol, 4 equiv). The reaction was then heated at 80° C. for 2 h. Upon cooling to ambient temperature, the reaction was concentrated in vacuo. The crude residue was then treated with MeOH (25 mL) and heated at 60° C. for 1 h. Upon cooling to ambient temperature, the reaction was concentrated in vacuo to give the HCl salt of the product as a tan glass (1.17 g, ~100%) which was used crude for the next reaction. LCMS (ESI, M+1): 308.40.

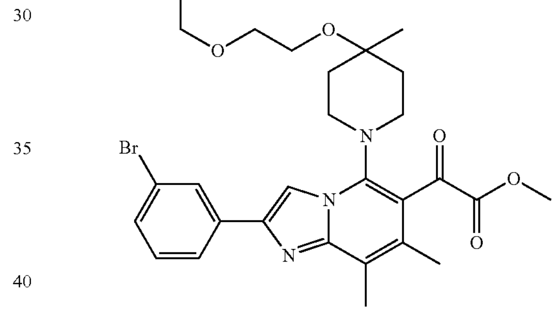

Methyl (R)-2-(5-(4-(2-(2-(benzyloxy)propoxy)ethoxy)-4-methylpiperidin-1-yl)-2-(3-bromophenyl)-7,8-dimethylimidazo[1,2-a]pyridin-6-yl)-2-oxoacetate To a yellow solution of 2-(3-bromophenyl)-5-chloro-7,8-dimethylimidazo[1,2-a]pyridine-6-carboxylic acid hydrochloride (10.2 g, 24.51 mmol, 1 equiv) and DIPEA (12.8 mL, 73.5 mmol, 3 equiv) in DCE (245 mL) was added HATU (11.2 g, 29.4 mmol, 1.2 equiv). After stirring 1 h, the reaction was diluted with EtOAc and washed with water (×1) and brine (×1). The EtOAc layer was then dried (Na2SO4) and concentrated in vacuo. The crude activated ester was then slurried in DCE (245 mL). 1-(cyanomethyl) tetrahydro-1H-thiophen-1-ium hexafluorophosphate(V) (9.4 g, 34.3 mmol, 1.4 equiv) followed by DIPEA (12.8 mL, 73.5 mmol, 3 equiv) were added. After stirring 18 h, the reaction was diluted with EtOAc and washed with water (×1) and brine (×1). The EtOAc layer was then dried ($Na_2SO_4$) and concentrated in vacuo to deliver a tan foam. The crude sulfonium ylide was taken up in MeOH (1000 mL) and THF (100 mL). Water (100 mL) then $KHSO_5$ monohydrate (12.5 g, 73.5 mmol, 3 equiv) (*Eur. J. Org. Chem.* 2002, 3429-3434) were added. After 3 d, the reaction stalled at ~40% conversion as judged by LCMS. The reaction mixture was neutralized with saturated aqueous NaHCO3 and concentrated in vacuo. The aquous residue was then partitioned between DCM and water. The DCM layer was then dried ($Na_2SO_4$) and concentrated in vacuo. The crude isolated sulfonium ylide ketoester mixture was then taken up in MeOH (1000 mL) and THF (100 mL). Water (100 mL) then $KHSO_5$ monohydrate (12.5 g, 73.5 mmol, 3 equiv) were added. After stirring 18 h, the oxidation was complete. The reaction mixture was neutralized with saturated aqueous $NaHCO_3$ and concentrated in vacuo. The aquous residue was then partitioned between DCM and water. The DCM layer was then dried ($Na_2SO_4$) and concentrated in vacuo to provide ~20 g viscous orange brown oil. The crude ketoester was dissolved in DMF (100 mL). DIPEA (12.8 mL, 73.5 mmol, 3 equiv) was added followed by (R)-4-(2-(2-(benzyloxy)propoxy)ethoxy)-4-methylpiperidine (7.53 g, 24.5 mmol, 1 equiv). After 18 h, the reaction was diluted with EtOAc and washed with water (×1) and brine (×1). The EtOAc layer was then dried (Na2SO4) and concentrated in vacuo. The crude product was purified by silica gel flash chromatography (0-100% EtOAc/hexane) to give the product (4.5 g, 27%) as a yellow solid. LCMS (ESI, M+1): 692.05.

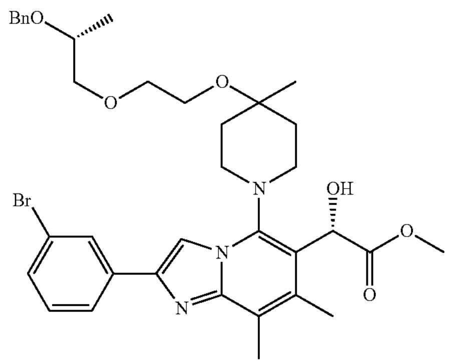 [SMILES: COC(=O)[C@@H](O)c1c(C)c(C)c2nc(-c3cccc(Br)c3)cn2c1N1CCC(C)(OCCOC[C@@H](C)OCc2ccccc2)CC1]

Methyl (S)-2-(5-(4-(2-((R)-2-(benzyloxy)propoxy)ethoxy)-4-methylpiperidin-1-yl)-2-(3-bromophenyl)-7,8-dimethylimidazo[1,2-a]pyridin-6-yl)-2-hydroxyacetate To a solution methyl (R)-2-(5-(4-(2-(2-(benzyloxy)propoxy)ethoxy)-4-methylpiperidin-1-yl)-2-(3-bromophenyl)-7,8-dimethylimidazo[1,2-a]pyridin-6-yl)-2-oxoacetate (4.5 g, 6.50 mmol, 1 equiv) and R-5,5-diphenyl-2-methyl-3,4-propano-1,3,2-oxazaborlidine (1.80 g, 6.50 mmol, 1 equiv) in toluene (130 mL) at −78° C. (IPA/dry ice) was added catechol borane (4.2 mL of a 50% solution in toluene, 19.5 mmol, 3 equiv). The reaction was then placed in a freezer at −25° C. for 3 d. The reaction was then cooled to −78° C. (IPA/dry ice) and quenched with 10% aqueous $K_2CO_3$. EtOAc was then added and the mixture was allowed to warm to ambient temperature. The mixture was then added to water and extract with EtOAc (×3). The combined EtOAc extracts were dried ($Na_2SO_4$) and concentrated in vacuo. The crude product was purified by silica gel flash chromatography (10-100% EtOAc/hexane) to give the product (4.5 g, 100%) as a white solid. LCMS (ESI, M+1): 694.05.

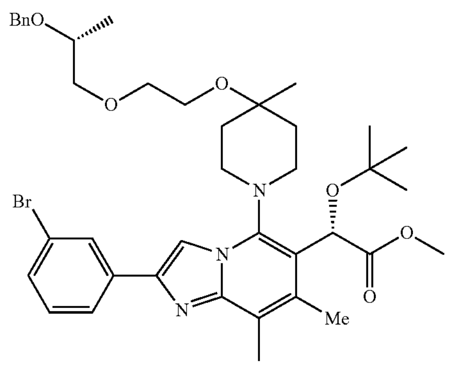 [SMILES: COC(=O)[C@@H](OC(C)(C)C)c1c(C)c(C)c2nc(-c3cccc(Br)c3)cn2c1N1CCC(C)(OCCOC[C@@H](C)OCc2ccccc2)CC1]

Methyl (S)-2-(5-(4-(2-((R)-2-(benzyloxy)propoxy)ethoxy)-4-methylpiperidin-1-yl)-2-(3-bromophenyl)-7,8-dimethylimidazo[1,2-a]pyridin-6-yl)-2-(tert-butoxy)acetate To a solution of methyl (S)-2-(5-(4-(2-((R)-2-(benzyloxy)propoxy)ethoxy)-4-methylpiperidin-1-yl)-2-(3-bromophenyl)-7,8-dimethylimidazo[1,2-a]pyridin-6-yl)-2-hydroxyacetate (4.50 g, 6.48 mmol, 1 equiv) in DCE (162 mL) and tert-butyl acetate (162 mL) was added 70% perchloric acid (1.2 mL, 19.4 mmol, 3 equiv). The reaction was sealed and stirred 3 h. The reaction was then diluted with EtOAc and washed with 10% aqueous $K_2CO_3$. The organic layer was then dried ($Na_2SO_4$) and concentrated in vacuo. The crude product was purified by silica gel flash chromatography (0-100% EtOAc/hexane) to give the product (2.9 g, 60%) as a pale yellow foam. In addition, starting material (1.0 g, 22%) was also recovered. LCMS (ESI, M+1): 750.15.

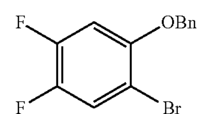 [SMILES: Fc1cc(Br)c(OCc2ccccc2)cc1F]

1-(Benzyloxy)-2-bromo-4,5-difluorobenzene

To a solution of 2-bromo-4,5-difluorophenol (3.92 g, 18.8 mmol, 1 equiv) and BnCl (2.6 mL, 22.51 mmol, 1.2 equiv) in MeCN (75 mL) was added potassium carbonate (5.2 g, 37.5 mmol, 2 equiv). The yellow slurry was heated to reflux for 3 h. Upon cooling to ambient temperature, the mixture was diluted with ether and filtered. The filtrate was concentrated in vacuo to provide the product (5.4 g, 96%) as a pale yellow oil. $^1H$ NMR (400 MHz, CDCl3) δ 7.50-7.32 (m, 6H), 6.81 (dd, J=11.8, 7.0 Hz, 1H), 5.12 (s, 2H).

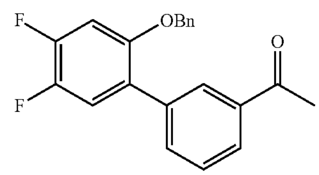 [SMILES: CC(=O)c1cccc(-c2cc(F)c(F)cc2OCc2ccccc2)c1]

1-(2'-(Benzyloxy)-4',5'-difluoro-[1,1'-biphenyl]-3-yl) ethanone

A solution of 1-(benzyloxy)-2-bromo-4,5-difluorobenzene (4.7 g, 15.7 mmol, 1 equiv), (3-acetylphenyl)boronic acid (3.6 g, 22.0 mmol, 1.4 equiv), $Pd(OAc)_2$ (0.35 g, 1.57 mmol, 0.1 equiv), 2 M $K_3PO_4$ (63 mL, 126 mmol, 8 equiv), and Sphos (1.29 g, 3.14 mmol, 0.2 equiv) in dioxane (157 mL) was heated at 80° C. for 2 h. Upon cooling to ambient temperature, the mixture was diluted with ether and washed with water. The ether layer was dried ($MgSO_4$) and concentrated in vacuo. The crude product was purified via silica gel flash column chromatography (0-30% EtOAc/hexane) to provide the product (3.6 g, 68%) as a yellow solid. $^1$H NMR (400 MHz, CDCl3) δ 8.13 (t, J=1.6 Hz, 1H), 7.98-7.91 (m, 1H), 7.74-7.69 (m, 1H), 7.54-7.47 (m, 1H), 7.37-7.28 (m, 5H), 7.22 (dd, J=10.8, 8.8 Hz, 1H), 6.91 (dd, J=11.8, 6.8 Hz, 1H), 5.03 (s, 2H), 2.57 (s, 3H); $^{19}$F NMR (376 MHz, CDCl3) δ −135.65 (s, 1F), −147.37 (s, 1F); LCMS (ESI, M+1): 339.05.

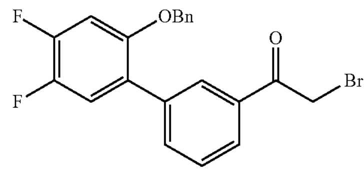 [SMILES: O=C(CBr)c1cccc(-c2cc(F)c(F)cc2OCc2ccccc2)c1]

1-(2'-(Benzyloxy)-4',5'-difluoro-[1,1'-biphenyl]-3-yl)-2-bromoethanone

To a solution of 1-(2'-(benzyloxy)-4',5'-difluoro-[1,1'-biphenyl]-3-yl)ethanone (4.0 g, 11.8 mmol, 1 equiv) in THF (59 mL) was added cupric bromide (5.3 g, 23.6 mmol, 2 equiv). The dark brown solution was heated at 40° C. for 3 h at which time the reaction was a yellow solution with a white precipitate. Upon cooling to ambient temperature, the mixture was diluted with ether and filtered. The filtrate was concentrated in vacuo. The crude product was purified via silica gel flash column chromatography (20-100% DCM/hexane) to provide the product (3.5 g, 69%) as a white solid. $^1$H NMR (500 MHz, $CDCl_3$) δ 8.17 (t, J=1.8 Hz, 1H), 7.97 (dt, J=7.8, 1.4 Hz, 1H), 7.75 (dt, J=7.7, 1.3 Hz, 1H), 7.55 (t, J=7.8 Hz, 1H), 7.40-7.30 (m, 5H), 7.23 (dd, J=10.7, 9.0 Hz, 1H), 6.93 (dd, J=12.0, 6.8 Hz, 1H); $^{19}$F NMR (471 MHz, CDCl3) δ −135.22 (s, 1F), −147.16 (s, 1F).

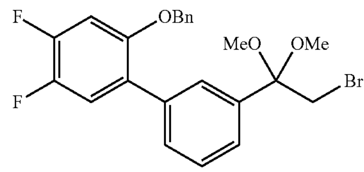 [SMILES: COC(CBr)(OC)c1cccc(-c2cc(F)c(F)cc2OCc2ccccc2)c1]

2-(Benzyloxy)-3'-(2-bromo-1,1-dimethoxyethyl)-4,5-difluoro-1,1'-biphenyl

To a solution of 1-(2'-(benzyloxy)-4',5'-difluoro-[1,1'-biphenyl]-3-yl)-2-bromoethanone (3.4 g, 8.24 mmol, 1 equiv) in MeOH (33 mL) and trimethyl orthoformate (9 mL) was added TsOH (0.157 g, 0.824 mmol, 0.1 equiv). The reaction was heated at reflux for 4 h. Upon cooling to ambient temperature, the mixture was diluted with ether and washed with 10% aqueous potassium carbonate, dried ($MgSO_4$), and concentrated in vacuo to provide the product (3.8 g, 99%) yellow glass that slowly crystalized. $^1$H NMR (400 MHz, $CDCl_3$) δ 7.74-7.67 (m, 1H), 7.52-7.39 (m, 3H), 7.36-7.17 (m, 6H), 6.89 (dd, J=12.0, 6.8 Hz, 1H), 5.00 (s, 2H), 3.57 (s, 2H), 3.21 (s, 6H).

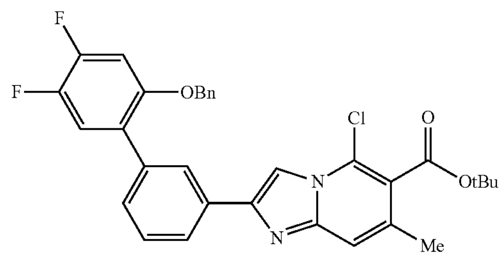 [SMILES: Cc1cc2nc(-c3cccc(-c4cc(F)c(F)cc4OCc4ccccc4)c3)cn2c(Cl)c1C(=O)OC(C)(C)C]

tert-Butyl 2-(2'-(benzyloxy)-4',5'-difluoro-[1,1'-biphenyl]-3-yl)-5-chloro-7-methylimidazo[1,2-a]pyridine-6-carboxylate A mixture of 2-(benzyloxy)-3'-(2-bromo-1,1-dimethoxyethyl)-4,5-difluoro-1,1'-biphenyl (3.8 g, 8.20 mmol, 1 equiv) and tert-butyl 6-amino-2-chloro-4-methylnicotinate (1.99 g, 8.20 mmol, 1 equiv) in chlorobenzene was heated to reflux for 75 min. Upon cooling to ambient temperature, the mixture was diluted with ether and filtered to provide the HBr salt of the product (2.88 g, 55%) as a tan solid. LCMS (ESI, M+1): 561.10.

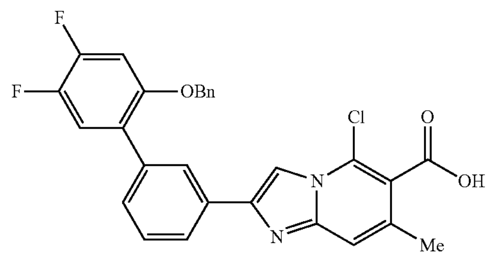 [SMILES: Cc1cc2nc(-c3cccc(-c4cc(F)c(F)cc4OCc4ccccc4)c3)cn2c(Cl)c1C(=O)O]

2-(2'-(Benzyloxy)-4',5'-difluoro-[1,1'-biphenyl]-3-yl)-5-chloro-7-methylimidazo[1,2-a]pyridine-6-carboxylic Acid A solution of tert-butyl 2-(2'-(benzyloxy)-4',5'-difluoro-[1,1'-biphenyl]-3-yl)-5-chloro-7-methylimidazo[1,2-a]pyridine-6-carboxylate HBr (2.9 g, 5.13 mmol, 1 equiv) in TFA (10 mL) was stirred for 2 h. The reaction was concentrated in vacuo. The residue was reconcentrated from THF (×3) to remove residual TFA to provide the TFA salt of the product (3.0 g, 94%) as a pale tan foam. LCMS (ESI, M+1): 505.15.

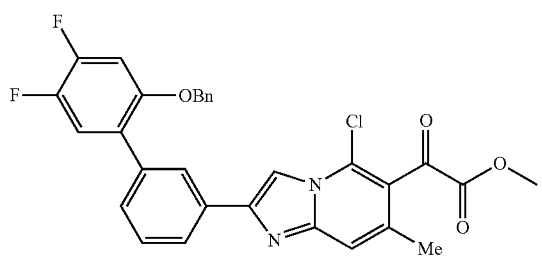 [SMILES: COC(=O)C(=O)c1c(C)cc2nc(-c3cccc(-c4cc(F)c(F)cc4OCc4ccccc4)c3)cn2c1Cl]

Methyl 2-(2-(2'-(benzyloxy)-4',5'-difluoro-[1,1'-biphenyl]-3-yl)-5-chloro-7-methylimidazo[1,2-a]pyridin-6-yl)-2-oxoacetate To a solution of 2-(2'-(benzyloxy)-4',5'-difluoro-[1,1'-biphenyl]-3-yl)-5-chloro-7-methylimidazo[1,2-a]pyridine-6-carboxylic acid TFA (3.0 g, 4.85 mmol, 1 equiv) and DIPEA (2.54 mL, 14.5 mmol, 3 equiv) in DCE (49 mL) was added HATU (2.2 g, 5.82 mmol, 1.2 equiv). After stirring 2 h, 1-(cyanomethyl)tetrahydro-1H-thiophen-1-ium, bromide salt (1.4 g, 6.79 mmol, 1.4 equiv) was added. After stirring 4 h, the reaction was washed with brine, dried ($Na_2SO_4$), and concentrated in vacuo. The crude sulfonium ylide was purified via silica gel flash column chromatography (20-100% EtOAc/hexane then 0-10% MeOH/DCM). The sulfonium ylide was repurified via silica gel flash column chromatography (0-60% acetone/hexane) to provide the sulfonium ylide (1.9 g) as a tan solid. The sulfonium ylide was taken up in MeOH (90 mL) and water (10 mL). Oxone (6.0 g, 9.69 mmol, 2 equiv) was added and the slurry was stirred 18 h. The mixture was diluted with THF and filtered. The filtrate was concentrated in vacuo and redissolved in DCM. This was washed with saturated aqueous sodium bicarbonate, dried ($Na_2SO_4$), and concentrated in vacuo. The crude product was purified via silica gel flash column chromatography (0-100% EtOAc/hexane) to provide product (0.50 g). The silica gel column was flushed (10% MeOH/DCM) to provide the saponified product (0.7 g). A solution of this acid in 1:1 MeOH:THF (49 mL) was treated with TMSdiazomethane (excess). After 1 h, the mixture was diluted with DCM and washed with saturated aqueous sodium bicarbonate, dried ($Na_2SO_4$), and concentrated in vacuo to provide another portion of product (0.6 g). Total isolation of product (1.1 g, 42%) as a tan solid. $^1$H NMR (400 MHz, $CDCl_3$) δ 8.14 (s, 1H), 7.97 (s, 2H), 7.55-7.45 (m, 3H), 7.35-7.14 (m, 7H), 6.90 (dd, J=11.9, 6.7 Hz, 1H), 5.05 (s, 2H), 4.01 (s, 3H), 2.42 (s, 3H); LCMS (ESI, M+1): 547.3.

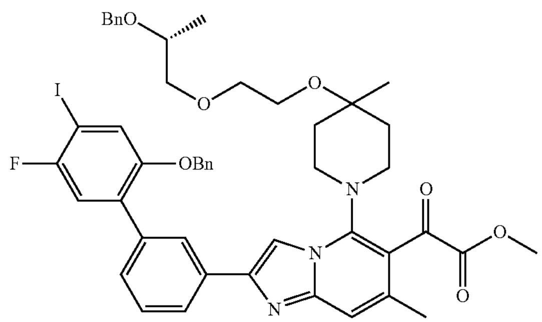 [SMILES: COC(=O)C(=O)c1c(C)cc2nc(-c3cccc(-c4cc(F)c(I)cc4OCc4ccccc4)c3)cn2c1N1CCC(C)(OCCOC[C@@H](C)OCc2ccccc2)CC1]

(R)-Methyl 2-(2-(2'-(benzyloxy)-4',5'-difluoro-[1,1'-biphenyl]-3-yl)-5-(4-(2-(2-(benzyloxy)propoxy)ethoxy)-4-methylpiperidin-1-yl)-7-methylimidazo[1,2-a]pyridin-6-yl)-2-oxoacetate To a solution of methyl 2-(2-(2'-(benzyloxy)-4',5'-difluoro-[1,1'-biphenyl]-3-yl)-5-chloro-7-methylimidazo[1,2-a]pyridin-6-yl)-2-oxoacetate (0.50 g, 0.914 mmol, 1 equiv) and (R)-4-(2-(2-(benzyloxy)propoxy)ethoxy)-4-methylpiperidine HCl (0.38 g, 1.10 mmol, 1.2 equiv) in DMF (5 mL) was added DIPEA (0.48 mL, 2.74 mmol, 3 equiv). After stirring 5 h, the reaction was diluted with EtOAc and washed with water. The EtOAc layer was dried ($Na_2SO_4$) and concentrated in vacuo. The crude product was purified via silica gel flash column chromatography (0-60% EtOAc[2% TEA]/hexane) to provide the product (0.49 g, 66%) as a yellow foam. $^1$H NMR (400 MHz, CDCl3) δ 8.14 (s, 1H), 8.04 (br. s., 1H), 7.96 (d, J=7.3 Hz, 1H), 7.57-7.44 (m, 2H), 7.40-7.24 (m, 12H), 6.87 (dd, J=11.8, 7.0 Hz, 1H), 5.01 (s, 2H), 4.49-4.41 (m, 1H), 4.39-4.32 (m, 1H), 3.94 (s, 3H), 3.89-3.14 (m, 10H), 2.72 (br. s., 1H), 2.41 (br. s., 3H), 1.86 (d, J=13.8 Hz, 2H), 1.64-1.58 (m, 2H), 1.25 (s, 3H), 1.00 (d, J=6.0 Hz, 3H); LCMS (ESI, M+1): 818.20.

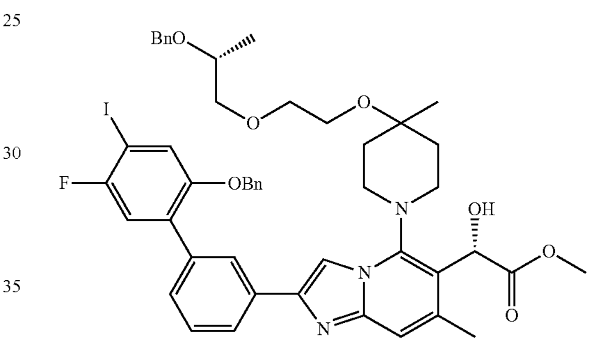

(S)-Methyl 2-(2-(2'-(benzyloxy)-4',5'-difluoro-[1,1'-biphenyl]-3-yl)-5-(4-(2-((R)-2-(benzyloxy)propoxy)ethoxy)-4-methylpiperidin-1-yl)-7-methylimidazo[1,2-a]pyridin-6-yl)-2-hydroxyacetate A solution of (R)-methyl 2-(2-(2'-(benzyloxy)-4',5'-difluoro-[1,1'-biphenyl]-3-yl)-5-(4-(2-(2-(benzyloxy)propoxy)ethoxy)-4-methylpiperidin-1-yl)-7-methylimidazo[1,2-a]pyridin-6-yl)-2-oxoacetate (0.90 g, 1.10 mmol, 1 equiv) and R-5,5-diphenyl-2-methyl-3,4-propano-1,3,2-oxazaborlidine (0.31 g, 1.10 mmol, 1 equiv) in toluene (22 mL) was cooled to −20° C. (IPA/dry ice). Catecholborane (0.47 mL of a 50% solution in toluene, 2.20 mmol, 2 equiv) was added. The reaction was stirred for 3 h with the temperature being maintained between −15° C. and −30° C. Upon warming to ambient temperature, the reaction was diluted with EtOAc, washed with 10% aqueous potassium carbonate, dried ($Na_2SO_4$), and concentrated in vacuo. The crude product was purified via silica gel flash column chromatography (10-100% EtOAc[2% TEA]/hexane) to provide the product (0.79 g, 88%) as a white foam. $^1$H NMR (400 MHz, CDCl3) δ 8.13 (s, 1H), 8.08 (s, 1H), 7.99-7.93 (m, 1H), 7.54-7.12 (m, 14H), 6.90-6.81 (m, 1H), 5.54 (s, 1H), 5.00 (s, 2H), 4.41 (d, J=12.3 Hz, 2H), 3.98-3.86 (m, 2H), 3.77 (s, 3H), 3.76-3.54 (m, 5H), 3.50-3.43 (m, 1H), 3.38-3.29 (m, 1H), 2.90-2.80 (m, 1H), 2.64-2.56 (m, 1H), 2.49 (s, 3H), 1.97-1.86 (m, 2H), 1.84-1.70 (m, 2H), 1.29 (s, 3H), 1.00 (d, J=6.3 Hz, 3H); LCMS (ESI, M+1): 820.15.

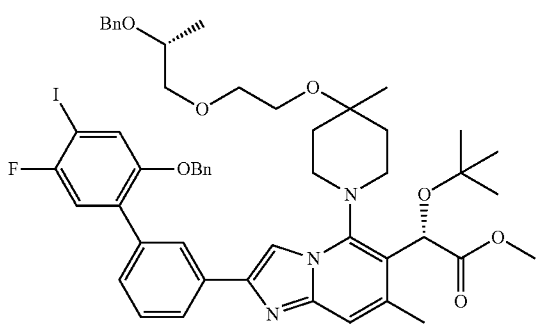 [SMILES: COC(=O)[C@@H](OC(C)(C)C)c1c(C)cc2nc(-c3cccc(-c4cc(F)c(I)cc4OCc4ccccc4)c3)cn2c1N1CCC(C)(OCCOC[C@@H](C)OCc2ccccc2)CC1]

(S)-Methyl 2-(2-(2'-(benzyloxy)-4',5'-difluoro-[1,1'-biphenyl]-3-yl)-5-(4-(2-((R)-2-(benzyloxy)propoxy) ethoxy)-4-methylpiperidin-1-yl)-7-methylimidazo[1,2-a]pyridin-6-yl)-2-(tert-butoxy)acetate To a solution of (9-methyl 2-(2-(2'-(benzyloxy)-4',5'-difluoro-[1,1'-biphenyl]-3-yl)-5-(4-(2-((R)-2-(benzyloxy) propoxy)ethoxy)-4-methylpiperidin-1-yl)-7-methylimidazo [1,2-a]pyridin-6-yl)-2-hydroxyacetate (0.79 g, 0.96 mmol, 1 equiv) in DCE (24 mL) and t-butyl acetate (24 mL) was added 70% $HClO_4$ (0.25 mL, 2.89 mml, 3 equiv). After 4 h, the reaction mixture was diluted with EtOAc and washed with 10% aqueous $K_2CO_3$. The organic layer was dried ($Na_2SO_4$) and concentrated in vacuo. The crude product was purified via silica gel flash column chromatography (0-100% EtOAc[2% TEA]/hexane) to provide the product (0.53 g, 63%) as a white foam. $^1$H NMR (400 MHz, $CDCl_3$) δ 8.15-8.09 (m, 1H), 8.05-8.02 (m, 1H), 7.97-7.92 (m, 1H), 7.54-7.42 (m, 3H), 7.34-7.14 (m, 11H), 6.89-6.81 (m, 1H), 6.11-6.05 (m, 1H), 5.01-4.98 (m, 2H), 4.51-4.40 (m, 2H), 3.69 (s, 3H), 4.00-3.35 (m, 9H), 3.03-2.93 (m, 1H), 2.70-2.63 (m, 1H), 2.48 (s, 3H), 1.96-1.88 (m, 2H), 1.71-1.61 (m, 2H), 1.30 (s, 3H), 1.26 (s, 9H), 1.08-1.03 (m, 3H); LCMS (ESI, M+1): 876.25.

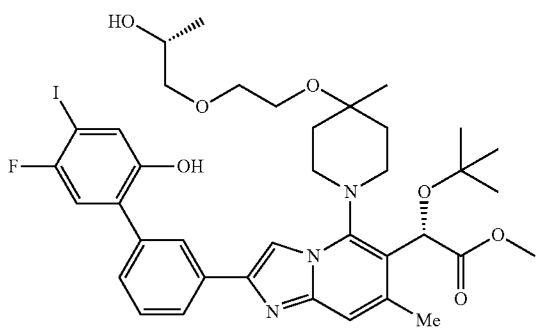 [SMILES: COC(=O)[C@@H](OC(C)(C)C)c1c(C)cc2nc(-c3cccc(-c4cc(F)c(I)cc4O)c3)cn2c1N1CCC(C)(OCCOC[C@@H](C)O)CC1]

(S)-Methyl 2-(tert-butoxy)-2-(2-(4',5'-difluoro-2'-hydroxy-[1,1'-biphenyl]-3-yl)-5-(4-(2-((R)-2-hydroxypropoxy)ethoxy)-4-methylpiperidin-1-yl)-7-methylimidazo[1,2-a]pyridin-6-yl)acetate To a solution of (S)-methyl 2-(2-(2'-(benzyloxy)-4',5'-difluoro-[1,1'-biphenyl]-3-yl)-5-(4-(2-((R)-2-(benzyloxy) propoxy)ethoxy)-4-methylpiperidin-1-yl)-7-methylimidazo [1,2-a]pyridin-6-yl)-2-(tert-butoxy)acetate (1.5 g, 1.71 mmol, 1 equiv) in THF (86 mL) was added CSA (0.40 g, 1.71 mmol, 1 equiv) and 10% Pd/C (0.36 g, 0.342 mmol, 0.2 equiv). The reaction mixture was then stirred under a balloon of hydrogen for 7 h. Upon completion, the reaction was filtered through celite and the filtrate was concentrated in vacuo. The crude residue was partitioned between DCM and saturated aqueous $NaHCO_3$. The DCM layer was dried ($Na_2SO_4$) and concentrated in vacuo to provide the product (1.1 g, 92%) which was used without further purification. $^1$H NMR (400 MHz, CDCl3) δ 8.15 (s, 1H), 8.07 (s, 1H), 7.99 (d, J=8.0 Hz, 1H), 7.54 (t, J=7.8 Hz, 1H), 7.35 (d, J=7.5 Hz, 1H), 7.29 (br. s., 1H), 7.13 (dd, J=10.8, 9.0 Hz, 1H), 6.82 (dd, J=11.5, 7.0 Hz, 1H), 6.03 (s, 1H), 3.69 (s, 3H), 4.06-3.66 (m, 6H), 3.64-3.60 (m, 1H), 3.52 (dd, J=10.3, 3.0 Hz, 1H), 3.25 (dd, J=10.2, 8.4 Hz, 1H), 3.03 (d, J=7.5 Hz, 1H), 2.75 (d, J=8.8 Hz, 1H), 2.57 (br. s., 1H), 2.46 (s, 3H), 1.99-1.70 (m, 4H), 1.33 (s, 3H), 1.26 (s, 9H), 1.05 (d, J=6.5 Hz, 3H); LCMS (ESI, M+1): 696.15.

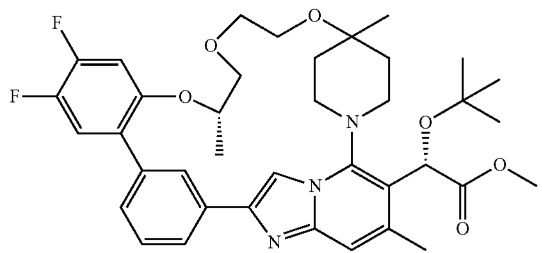 [SMILES: COC(=O)[C@@H](OC(C)(C)C)c1c(C)cc2nc3cn2c1N1CCC(C)(CC1)OCCOC[C@H](C)Oc1cc(F)c(F)cc1-c1cccc-3c1]

Methyl (2S)-2-(tert-butoxy)-2-[(22S)-17,18-difluoro-4,22,28-trimethyl-21,24,27-trioxa-1,7,34-triazahexacyclo[$26.2.2.1^{6,9}.1^{10,14}.0^{2,7}.0^{15,20}$]tetratriaconta-2,4,6(34),8,10(33),11,13,15(20),16,18-decaen-3-yl]acetate To a solution of (9-methyl 2-(tert-butoxy)-2-(2-(4',5'-difluoro-2'-hydroxy-[1,1'-biphenyl]-3-yl)-5-(4-(2-((R)-2-hydroxypropoxy)ethoxy)-4-methylpiperidin-1-yl)-7-methylimidazo[1,2-a]pyridin-6-yl)acetate (1.19 g, 1.71 mmol, 1 equiv) and triphenylphosphine (0.54 g, 2.05 mmol, 1.2 equiv) in THF (171 mL) was added DIAD (0.40 mL, 2.05 mmol, 1.2 equiv). After 0.5 h, dilute with DCM and wash with saturated aqueous $NaHCO_3$. The DCM layer was dried ($Na_2SO_4$) and concentrated in vacuo. The crude product was purified via silica gel flash column chromatography (0-100% EtOAc[2% TEA]/hexane) to provide the product (1.1 g, 95%) as an off white foam. $^1$H NMR (400 MHz, $CDCl_3$) δ 8.32 (s, 1H), 8.21 (d, J=7.8 Hz, 1H), 8.13 (s, 1H), 7.52 (t, J=7.7 Hz, 1H), 7.32 (s, 1H), 7.26 (d, J=2.3 Hz, 1H), 6.87 (dd, J=12.2, 6.9 Hz, 1H), 6.06 (s, 1H), 4.66-4.55 (m, 1H), 4.04 (t, J=10.7 Hz, 1H), 3.93 (dd, J=12.0, 7.3 Hz, 2H), 3.84 (t, J=10.7 Hz, 1H), 3.69 (s, 3H), 3.66 (d, J=3.0 Hz, 1H), 3.62-3.56 (m, 2H), 3.05 (d, J=9.3 Hz, 1H), 2.67 (d, J=8.5 Hz, 1H), 2.47 (s, 3H), 2.02-1.88 (m, 2H), 1.85-1.69 (m, 2H), 1.58 (s, 3H), 1.26 (s, 9H), 1.13 (d, J=6.3 Hz, 3H); LCMS (ESI, M+1): 678.15.

Example 1

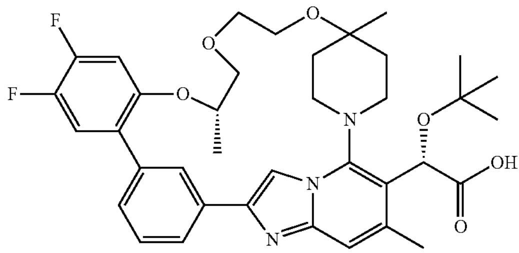 [SMILES: Cc1cc2nc3cn2c(c1[C@H](OC(C)(C)C)C(=O)O)N1CCC(C)(CC1)OCCOC[C@H](C)Oc1cc(F)c(F)cc1-c1cccc-3c1]

(2S)-2-(tert-Butoxy)-2-[(22S)-17,18-difluoro-4,22,28-trimethyl-21,24,27-trioxa-1,7,34-triazahexacyclo[26.2.2.1^{6,9}.1^{10,14}.0^{2,7}.0^{15,20}]tetratriaconta-2,4,6(34),8,10(33),11,13,15(20),16,18-decaen-3-yl]acetic Acid To a solution of methyl (2S)-2-(tert-butoxy)-2-[(22S)-17,18-difluoro-4,22,28-trimethyl-21,24,27-trioxa-1,7,34-triazahexacyclo[26.2.2.1^{6,9}.1^{10,14}.0^{2,7}.0^{15,20}]tetratriaconta-2,4,6(34),8,10(33),11,13,15(20),16,18-decaen-3-yl]acetate (40 mg, 0.059 mmol, 1 equiv) in MeOH (0.59 mL) was added 10 N NaOH (0.059 mL, 0.59 mmol, 10 equiv). The mixture was heated at 70° C. for 2 h. Upon cooling to ambient temperature, the mixture was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-90% B over 15 minutes, then a 5-minute hold at 100% B; Flow: 20 mL/min. Fractions containing the desired product were combined and dried via centrifugal evaporation to provide the product (18 mg, 47%). $^1$H NMR (500 MHz, DMSO-$d_6$) δ 8.39 (s, 1H), 8.16 (s, 1H), 8.11 (d, J=7.7 Hz, 1H), 7.54-7.44 (m, 2H), 7.40 (dd, J=12.8, 7.0 Hz, 1H), 7.32 (d, J=7.7 Hz, 1H), 7.29 (s, 1H), 5.94 (br. s., 1H), 4.91 (br. s., 1H), 3.94 (t, J=11.7 Hz, 1H), 3.80-3.57 (m, 6H), 3.41 (d, J=7.3 Hz, 1H), 3.05 (d, J=7.3 Hz, 1H), 2.57 (d, J=9.2 Hz, 1H), 2.41 (s, 3H), 2.01 (d, J=13.2 Hz, 1H), 1.83-1.76 (m, 1H), 1.75-1.66 (m, 2H), 1.22 (s, 3H), 1.19 (s, 9H), 1.09 (d, J=5.9 Hz, 3H); LCMS (ESI, M+1): 664.0.

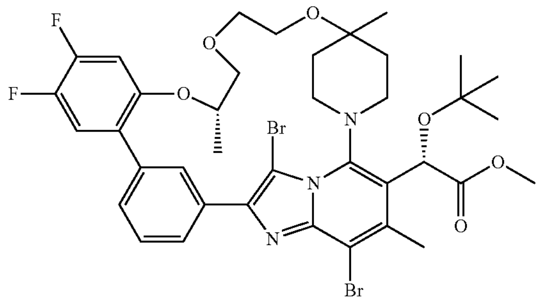 [SMILES: COC(=O)[C@@H](OC(C)(C)C)c1c(C)c(Br)c2nc3c(Br)n2c1N1CCC(C)(CC1)OCCOC[C@H](C)Oc1cc(F)c(F)cc1-c1cccc-3c1]

Methyl (2S)-2-(tert-butoxy)-2-[(22S)-5,8-dibromo-17,18-difluoro-4,22,28-trimethyl-21,24,27-trioxa-1,7,34-triazahexacyclo[26.2.2.1^{6,9}.1^{10,14}.0^{2,7}.0^{15,20}]tetratriaconta-2,4,6(34),8,10(33),11,13,15(20),16,18-decaen-3-yl]acetate To a solution of methyl (2S)-2-(tert-butoxy)-2-[(22S)-17,18-difluoro-4,22,28-trimethyl-21,24,27-trioxa-1,7,34-triazahexacyclo[26.2.2.1^{6,9}.1^{10,14}.0^{2,7}.0^{15,20}]tetratriaconta-2,4,6(34),8,10(33),11,13,15(20),16,18-decaen-3-yl]acetate (0.30 g, 0.443 mmol, 1 equiv) in MeCN (4.4 mL) was added NBS (0.17 g, 0.974 mmol, 2.2 equiv). After 2 h, the yellow solution was diluted with EtOAc and washed with 1 N $Na_2S_2O_3$. The organic layer was dried ($Na_2SO_4$) and concentrated in vacuo. The crude product was purified via silica gel flash column chromatography (0-100% EtOAc [2% TEA]/hexane) to provide the product (0.325 g, 88%) as an off white solid. $^1$H NMR (400 MHz, CDCl3) δ 8.55 (s, 1H), 8.03 (d, J=7.8 Hz, 1H), 7.53 (t, J=7.8 Hz, 1H), 7.31 (d, J=7.5 Hz, 2H), 7.22 (dd, J=11.0, 9.3 Hz, 1H), 6.81 (dd, J=12.5, 6.8 Hz, 1H), 6.34-5.93 (m, 1H), 4.55-4.46 (m, 1H), 4.44-4.34 (m, 2H), 3.95 (d, J=10.8 Hz, 1H), 3.83-3.63 (m, 7H), 3.31 (br. s., 1H), 2.59 (s, 3H), 2.54 (br. s., 1H), 2.01-1.61 (m, 4H), 1.30 (s, 3H), 1.26 (s, 9H), 1.24 (d, J=6.8 Hz, 3H); LCMS (ESI, M+1): 833.95.

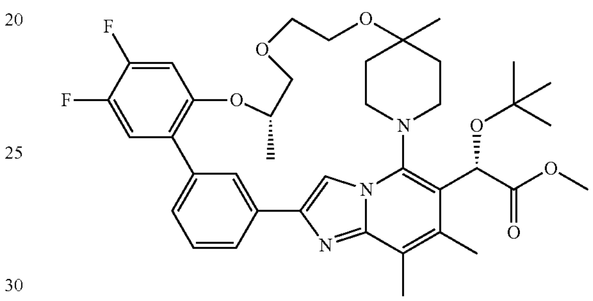

Methyl (2S)-2-(tert-butoxy)-2-[(22S)-17,18-difluoro-4,5,22,28-tetramethyl-21,24,27-trioxa-1,7,34-triazahexacyclo[26.2.2.1^{6,9}.1^{10,14}.0^{2,7}.0^{15,20}]tetratriaconta-2,4,6(34),8,10(33),11,13,15(20),16,18-decaen-3-yl]acetate A solution of methyl (2S)-2-(tert-butoxy)-2-[(22S)-5,8-dibromo-17,18-difluoro-4,22,28-trimethyl-21,24,27-trioxa-1,7,34-triazahexacyclo[26.2.2.1^{6,9}.1^{10,14}.0^{2,7}.0^{15,20}]tetratriaconta-2,4,6(34),8,10(33),11,13,15(20),16,18-decaen-3-yl]acetate (50 mg, 0.060 mmol, 1 equiv), methylboronic acid (36 mg, 0.598 mmol, 10 equiv), $Pd(OAc)_2$ (8 mg, 0.036 mmol, 0.6 equiv), Sphos (29 mg, 0.072 mmol, 1.2 equiv), and 2 M $K_3PO_4$ (0.30 mL, 0.598 mmol, 10 equiv) in dioxane (1.2 mL) was heated at 100° C. for 1 h. Upon cooling to ambient temperature, reaction mixture was diluted with EtOAc and washed with water. The organic layer was dried ($Na_2SO_4$) and concentrated in vacuo. The crude product was purified via silica gel flash column chromatography (0-100% EtOAc [2% TEA]/hexane) to provide the product (37 mg, 89%) as a white foam. $^1$H NMR (400 MHz, CDCl3) δ 8.34-8.27 (m, 2H), 8.12 (s, 1H), 7.52 (t, J=7.5 Hz, 1H), 7.28-7.23 (m, 2H), 6.88 (dd, J=12.2, 6.9 Hz, 1H), 6.20 (s, 1H), 4.59 (td, J=6.6, 2.9 Hz, 1H), 4.08-4.01 (m, 1H), 3.99-3.89 (m, 2H), 3.85 (t, J=10.5 Hz, 1H), 3.74-3.69 (m, 2H), 3.69 (s, 3H), 3.62-3.56 (m, 2H), 3.04 (d, J=10.0 Hz, 1H), 2.70 (d, J=8.0 Hz, 1H), 2.62 (s, 3H), 2.38 (s, 3H), 2.02-1.89 (m, 2H), 1.75 (qd, J=13.2, 4.8 Hz, 2H), 1.29 (d, J=1.0 Hz, 3H), 1.26 (s, 9H), 1.13 (d, J=6.3 Hz, 3H); LCMS (ESI, M+1): 692.55.

Example 2

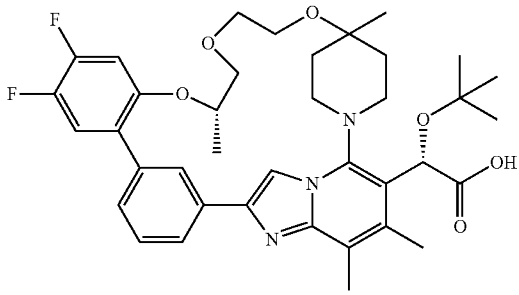 [SMILES: Cc1c([C@H](OC(C)(C)C)C(=O)O)c2n3cc(nc3c1C)-c1cccc(c1)-c1cc(F)c(F)cc1O[C@@H](C)COCCOC1(C)CCN2CC1]

(2S)-2-(tert-Butoxy)-2-[(22S)-17,18-difluoro-4,5,22,28-tetramethyl-21,24,27-trioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic Acid To a solution of methyl (2S)-2-(tert-butoxy)-2-[(22S)-17,18-difluoro-4,5,22,28-tetramethyl-21,24,27-trioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (37 mg, 0.053 mmol, 1 equiv) in MeOH (1.1 mL) was added 10 N NaOH (0.107 mL, 1.07 mmol, 20 equiv). A few drops THF added to aid solubility. The mixture was heated at 70° C. for 2 h. Upon cooling to ambient temperature, the crude mixture was purified directly by reverse phase C18 chromatography (0-100% MeCN/water) to provide the Na salt of the product (27 mg, 68%) as a white solid. $^1$H NMR (400 MHz, DMSO-$d_6$) δ 8.33 (s, 1H), 8.14 (d, J=7.8 Hz, 1H), 8.08 (s, 1H), 7.53-7.44 (m, 2H), 7.38 (dd, J=13.1, 7.0 Hz, 1H), 7.29 (d, J=7.5 Hz, 1H), 5.61 (s, 1H), 4.89 (dd, J=6.1, 3.6 Hz, 1H), 3.95 (t, J=10.5 Hz, 1H), 3.82-3.55 (m, 7H), 3.49-3.40 (m, 1H), 2.55 (br. s., 1H), 2.43 (s, 3H), 2.31 (s, 3H), 1.92 (d, J=13.3 Hz, 1H), 1.82 (d, J=12.5 Hz, 1H), 1.72-1.54 (m, 2H), 1.20 (s, 3H), 1.13 (s, 9H), 1.09 (d, J=6.0 Hz, 3H); LCMS (ESI, M+1): 678.25.

Example 3

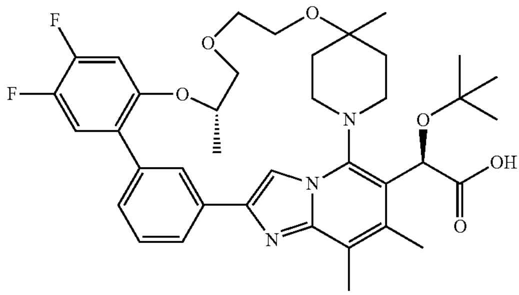 [SMILES: Cc1c([C@@H](OC(C)(C)C)C(=O)O)c2n3cc(nc3c1C)-c1cccc(c1)-c1cc(F)c(F)cc1O[C@@H](C)COCCOC1(C)CCN2CC1]

(2R)-2-(tert-butoxy)-2-((6S,Z)-44,45-difluoro-14,27,6-trimethyl-5,8,11-trioxa-2(5,2)-imidazo[1,2-a]pyridina-1(1,4)-piperidina-3(1,3),4(1,2)-dibenzenacycloundecaphane-26-yl)acetic Acid To a solution of Methyl (2S)-2-(tert-butoxy)-2-[(22S)-17,18-difluoro-4,5,22,28-tetramethyl-21,24,27-trioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (1.42 g, 2.05 mmol, 1 equiv) in THF (4 mL). MeOH (16 mL) added followed by 10 N NaOH (4.1 mL, 41.1 mmol, 20 equiv). The reaction was heated at 60° C. for 1.5 h. Upon cooling to ambient temperature, the crude reaction mixture was purified via C18 column (5-80% MeCN/water) to provide 1.37 g white solid contaminated with a small amount of a diastereomer. Further purification SFC chromatography provided the minor diastereomer (8 mg, 0.6%). LCMS (ESI, M+1): 678.15.

Example 4

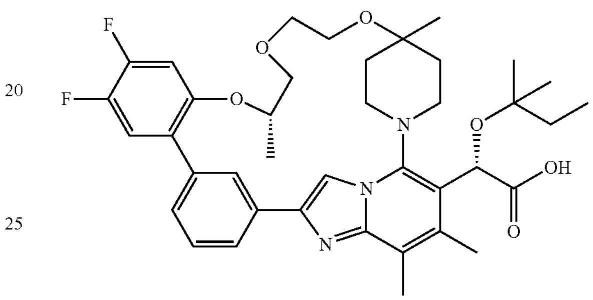

(2S)-2-[(22S)-17,18-Difluoro-4,5,22,28-tetramethyl-21,24,27-trioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-[(2-methylbutan-2-yl)oxy]acetic Acid To a solution of methyl (2S)-2-(tert-butoxy)-2-[(22S)-17,18-difluoro-4,5,22,28-tetramethyl-21,24,27-trioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (20 mg, 0.029 mmol, 1 equiv) in DCM (1.5 mL) and 2-methyl-2-butene (2 mL) was added 70% perchloric acid (5 μL, 0.087 mmol, 3 equiv). The reaction was stirred at ambient temperature for 18 h and then heated in the microwave (1 h @ 80° C.). The reaction mixture was then added to saturated aqueous $NaHCO_3$ and extracted with DCM (×2). The combined DCM extracts were dried ($Na_2SO_4$) and concentrated in vacuo. The crude product was then taken up in DCM (1.5 mL) and 2-methyl-2-butene (2 mL). 70% Perchloric acid (5 μL, 0.087 mmol, 3 equiv) was added. After 1 h, 10 N NaOH (0.5 mL) followed by MeOH (2 mL) was added. After ~10 s, the yellow solution became colorless. The mixture was then heated to 70° C. for 2 h. After cooling to ambient temperature, the crude reaction mixture was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 20 minutes, then a 6-minute hold at 100% B; Flow: 20 mL/min. Fractions containing the desired products were combined and dried via centrifugal evaporation. (2S)-2-[(22S)-17,18-difluoro-4,5,22,28-tetramethyl-21,24,27-trioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-[(2-methylbutan-2-yl)oxy]acetic acid (1.7 mg, 8%) was isolated. $^1$H NMR (500 MHz, DMSO-$d_6$) δ 8.35 (s, 1H), 8.15 (d, J=7.7 Hz, 1H), 8.10 (s, 1H), 7.53-7.48 (m, 2H), 7.39 (dd, J=13.2, 7.0 Hz, 1H), 7.30 (d, J=8.1 Hz, 1H), 5.67 (s, 1H), 4.90 (d, J=4.0 Hz, 1H), 3.96 (t, J=11.9 Hz, 1H), 3.82-3.36 (m, 10H), 2.45 (s, 3H), 2.34 (s, 3H), 1.93 (d, J=11.7 Hz, 1H), 1.83 (d, J=12.5 Hz, 1H), 1.70-1.60 (m, 2H), 1.50-1.39 (m, 2H), 1.21 (s, 3H), 1.12 (s, 3H), 1.10 (d, J=6.2 Hz, 3H), 1.08 (s, 3H), 0.76 (t, J=7.3 Hz, 3H); LCMS (ESI, M+1): 692.2.

Example 5

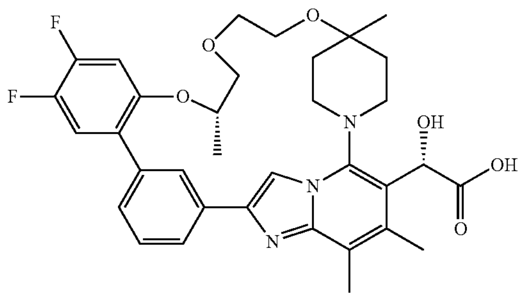 [SMILES: Cc1c([C@H](O)C(=O)O)c2n3cc(nc3c1C)-c1cccc(c1)-c1cc(F)c(F)cc1O[C@@H](C)COCCOC1(C)CCN2CC1]

(2S)-2-[(22S)-17,18-Difluoro-4,5,22,28-tetramethyl-21,24,27-trioxa-1,7,34-triazahexacyclo[26.2.2.$1^{6,9}.1^{10,14}.0^{2,7}.0^{15,20}$]tetratriaconta-2,4,6(34),8,10(33),11,13,15(20),16,18-decaen-3-yl]-2-hydroxy-acetic Acid Isolated from preceeding reaction (6.5 mg, 36%). $^1$H NMR (500 MHz, DMSO-$d_6$) δ 8.36 (s, 1H), 8.17 (d, J=7.7 Hz, 1H), 8.08 (s, 1H), 7.56-7.48 (m, 2H), 7.38 (dd, J=13.2, 7.0 Hz, 1H), 7.30 (d, J=7.7 Hz, 1H), 5.41 (br. s., 1H), 4.90 (br. s., 1H), 3.91-3.54 (m, 8H), 3.08 (br. s., 1H), 2.59 (d, J=11.4 Hz, 1H), 2.46 (s, 3H), 2.21 (s, 3H), 1.92 (d, J=12.1 Hz, 1H), 1.73 (br. s., 2H), 1.63 (br. s., 1H), 1.20 (s, 3H), 1.11 (d, J=6.2 Hz, 3H); LCMS (ESI, M+1): 622.2.

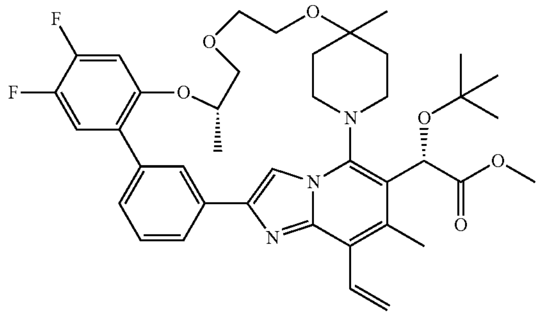 [SMILES: C=Cc1c(C)c([C@H](OC(C)(C)C)C(=O)OC)c2n3cc(nc13)-c1cccc(c1)-c1cc(F)c(F)cc1O[C@@H](C)COCCOC1(C)CCN2CC1]

Methyl (2S)-2-(tert-butoxy)-2-[(22S)-5-ethenyl-17,18-difluoro-4,22,28-trimethyl-21,24,27-trioxa-1,7,34-triazahexacyclo[26.2.2.$1^{6,9}.1^{10,14}.0^{2,7}.0^{15,20}$]tetratriaconta-2,4,6(34),8,10(33),11,13,15(20),16,18-decaen-3-yl]acetate A solution of methyl (2S)-2-(tert-butoxy)-2-[(22S)-5,8-dibromo-17,18-difluoro-4,22,28-trimethyl-21,24,27-trioxa-1,7,34-triazahexacyclo[26.2.2.$1^{6,9}.1^{10,14}.0^{2,7}.0^{15,20}$]tetratriaconta-2,4,6(34),8,10(33),11,13,15(20),16,18-decaen-3-yl] acetate (0.27 g, 0.323 mmol, 1 equiv), potassium vinyltrifluoroborate (0.43 g, 3.23 mmol, 10 equiv), $Pd(OAc)_2$ (44 mg, 0.194 mmol, 0.6 equiv), Sphos (159 mg, 0.388 mmol, 1.2 equiv), and 2 M $K_3PO_4$ (1.6 mL, 3.23 mmol, 10 equiv) in dioxane (6.5 mL) was heated at 100° C. for 3 h. Upon cooling to ambient temperature, reaction mixture was diluted with EtOAc and washed with water. The organic layer was dried ($Na_2SO_4$) and concentrated in vacuo. The crude product was purified via silica gel flash column chromatography (0-100% EtOAc [2% TEA]/hexane) to provide the product (115 mg, 51%) as a yellow foam. $^1$H NMR (400 MHz, CDCl3) δ 8.37-8.26 (m, 2H), 8.13 (s, 1H), 7.57-7.47 (m, 1H), 7.30-7.22 (m, 2H), 7.13 (dd, J=17.4, 11.7 Hz, 1H), 6.95-6.81 (m, 2H), 6.22 (br. s., 1H), 5.82 (dd, J=11.7, 2.4 Hz, 1H), 4.60 (td, J=6.7, 2.8 Hz, 1H), 4.05 (t, J=10.7 Hz, 1H), 4.00-3.90 (m, 2H), 3.85 (t, J=10.5 Hz, 1H), 3.69 (s, 3H), 3.74-3.66 (m, 2H), 3.65-3.54 (m, 2H), 3.07 (d, J=10.0 Hz, 1H), 2.70 (d, J=8.3 Hz, 1H), 2.49 (s, 3H), 2.04-1.88 (m, 2H), 1.76 (qd, J=12.5, 5.0 Hz, 2H), 1.30 (s, 3H), 1.26 (s, 9H), 1.14 (d, J=6.3 Hz, 3H); LCMS (ESI, M+1): 704.70.

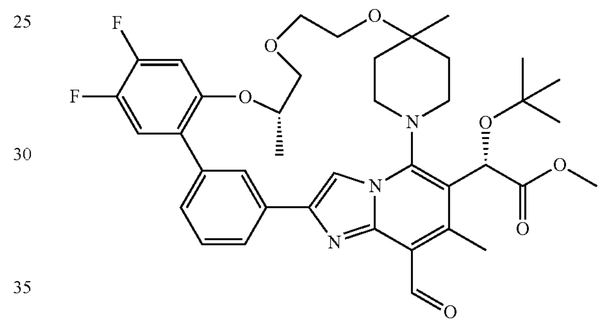

Methyl (2S)-2-(tert-butoxy)-2-[(22S)-17,18-difluoro-5-formyl-4,22,28-trimethyl-21,24,27-trioxa-1,7,34-triazahexacyclo[26.2.2.$1^{6,9}.1^{10,14}.0^{2,7}.0^{15,20}$]tetratriaconta-2,4,6(34),8,10(33),11,13,15(20),16,18-decaen-3-yl]acetate To a solution of methyl (2S)-2-(tert-butoxy)-2-[(22S)-5-ethenyl-17,18-difluoro-4,22,28-trimethyl-21,24,27-trioxa-1,7,34-triazahexacyclo[26.2.2.$1^{6,9}.1^{10,14}.0^{2,7}.0^{15,20}$]tetratriaconta-2,4,6(34),8,10(33),11,13,15(20),16,18-decaen-3-yl] acetate (115 mg, 0.163 mmol, 1 equiv) in dioxane (4.9 mL) and water (1.6 mL) was added $NaIO_4$ (122 mg, 0.572 mmol, 3.5 equiv) followed by aqueous 4% $OsO_4$ (0.128 mL, 0.016 mmol, 0.1 equiv). After 2 h, the yellow slurry was diluted with EtOAc and washed with 1 N $Na_2S_2O_3$. The organic layer was dried ($Na_2SO_4$) and concentrated in vacuo. The crude product was purified via silica gel flash column chromatography (0-100% EtOAc [2% TEA]/hexane) to provide the product (80 mg, 69%) as a yellow solid. $^1$H NMR (400 MHz, CDCl3) δ 11.24 (s, 1H), 8.38 (s, 1H), 8.31 (d, J=7.8 Hz, 1H), 8.22 (s, 1H), 7.56 (t, J=7.8 Hz, 1H), 7.32-7.23 (m, 2H), 6.86 (dd, J=12.0, 6.8 Hz, 1H), 6.08 (br. s., 1H), 4.70-4.56 (m, 1H), 4.06 (t, J=10.8 Hz, 1H), 4.01-3.89 (m, 2H), 3.85 (t, J=10.7 Hz, 1H), 3.71 (s, 3H), 3.74-3.56 (m, 4H), 3.14 (d, J=11.0 Hz, 1H), 2.78 (s, 3H), 2.66 (d, J=11.0 Hz, 1H), 2.04-1.66 (m, 4H), 1.31 (s, 3H), 1.26 (s, 9H), 1.15 (d, J=6.3 Hz, 3H); LCMS (ESI, M+1): 706.20.

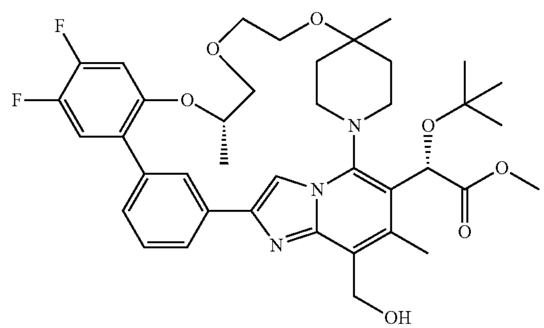 [SMILES: COC(=O)[C@@H](OC(C)(C)C)c1c(C)c(CO)c2nc3cn2c1N1CCC(C)(CC1)OCCOC[C@H](C)Oc1cc(F)c(F)cc1-c1cccc-3c1]

Methyl (2S)-2-(tert-butoxy)-2-[(22S)-17,18-difluoro-5-(hydroxymethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate To a solution of methyl (2S)-2-(tert-butoxy)-2-[(22S)-17,18-difluoro-5-formyl-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate (42 mg, 0.060 mmol, 1 equiv) in MeOH (1.2 mL) was added $NaBH_4$ (9 mg, 0.238 mmol, 4 equiv). After 1 h, the reaction was diluted with DCM and washed with saturated aqueous $NaHCO_3$. The DCM layer was dried ($Na_2SO_4$) and concentrated in vacuo. The crude product was purified via silica gel flash column chromatography (0-100% EtOAc[2% TEA]/hexane) to provide the product (29 mg, 69%) as a white solid. $^1$H NMR (400 MHz, CDCl3) δ 8.35 (s, 1H), 8.22 (d, J=7.8 Hz, 1H), 8.14 (s, 1H), 7.53 (t, J=7.7 Hz, 1H), 7.27 (s, 2H), 6.86 (dd, J=12.3, 6.8 Hz, 1H), 6.19 (br. s., 1H), 5.12 (s, 2H), 4.66-4.54 (m, 1H), 4.08-3.80 (m, 4H), 3.69 (s, 3H), 3.74-3.56 (m, 4H), 3.04 (d, J=10.0 Hz, 1H), 2.67 (d, J=10.0 Hz, 1H), 2.38 (s, 3H), 2.00 (d, J=15.1 Hz, 1H), 1.92 (d, J=12.3 Hz, 1H), 1.82-1.69 (m, 2H), 1.30 (s, 3H), 1.25 (s, 9H), 1.15 (d, J=6.3 Hz, 3H); LCMS (ESI, M+1): 708.20.

Example 6

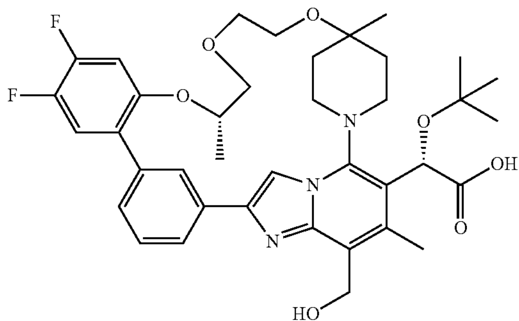 [SMILES: Cc1c([C@H](OC(C)(C)C)C(=O)O)c2n3cc(nc3c1CO)-c1cccc(c1)-c1cc(F)c(F)cc1O[C@@H](C)COCCOC1(C)CCN2CC1]

(2S)-2-(tert-Butoxy)-2-[(22S)-17,18-difluoro-5-(hydroxymethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic Acid To a solution of methyl (2S)-2-(tert-butoxy)-2-[(22S)-17,18-difluoro-5-(hydroxymethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate (29 mg, 0.041 mmol, 1 equiv) in MeOH (1.0 mL) was added 10 N NaOH (0.082 mL, 0.819 mmol, 20 equiv). A few drops THF added to aid solubility. The mixture was heated at 70° C. for 3 h. Upon cooling to ambient temperature, the crude mixture was purified directly by reverse phase C18 chromatography (0-100% MeCN/water) to provide the Na salt of the product (30 mg, 97%) as a white solid. $^1$H NMR (400 MHz, DMSO-$d_6$) δ 8.35 (s, 1H), 8.15-8.07 (m, 2H), 7.54-7.44 (m, 2H), 7.39 (dd, J=13.1, 7.3 Hz, 1H), 7.29 (d, J=7.5 Hz, 1H), 5.59 (s, 1H), 5.09-4.79 (m, 4H), 3.96 (t, J=10.8 Hz, 1H), 3.82-3.53 (m, 8H), 3.45 (d, J=6.5 Hz, 1H), 2.41 (s, 3H), 1.93 (d, J=12.5 Hz, 1H), 1.82 (d, J=12.8 Hz, 1H), 1.72-1.57 (m, 2H), 1.21 (s, 3H), 1.13 (s, 9H), 1.09 (d, J=6.3 Hz, 3H); LCMS (ESI, M+1): 694.20.

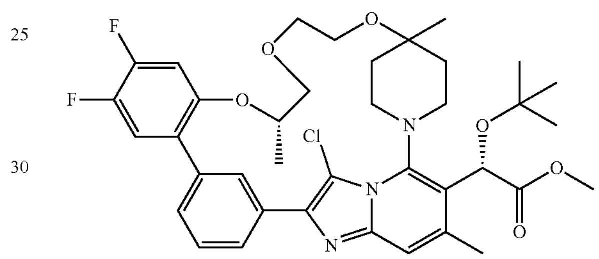

Methyl (2S)-2-(tert-butoxy)-2-[(22S)-8-chloro-17,18-difluoro-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate To a solution of methyl (2S)-2-(tert-butoxy)-2-[(22S)-17,18-difluoro-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate (61 mg, 0.090 mmol, 1 equiv) in MeCN (0.90 mL) was added NCS (12 mg, 0.090 mmol, 1 equiv). After 2 h, the yellow solution was diluted with EtOAc and washed with saturated aqueous $NaHCO_3$. The organic layer was dried ($Na_2SO_4$) and concentrated in vacuo. The crude product was purified via silica gel flash column chromatography (0-100% EtOAc/hexane) to provide the product (43 mg, 67%) as a white solid. $^1$H NMR (400 MHz, CDCl3) δ 8.64 (s, 1H), 7.99 (d, J=7.8 Hz, 1H), 7.60-7.49 (m, 1H), 7.36-7.30 (m, 2H), 7.25-7.19 (m, 1H), 6.82 (dd, J=12.5, 6.8 Hz, 1H), 6.01 (br. s., 1H), 4.69-4.38 (m, 1H), 4.28-4.18 (m, 1H), 3.70 (s, 3H), 3.87-3.56 (m, 7H), 3.28 (br. s., 1H), 2.54 (br. s., 1H), 2.49 (s, 3H), 1.91 (br. s., 3H), 1.74-1.66 (m, 1H), 1.30 (s, 3H), 1.27 (s, 9H), 1.22 (d, J=6.3 Hz, 3H); LCMS (ESI, M+1): 712.10.

Example 7

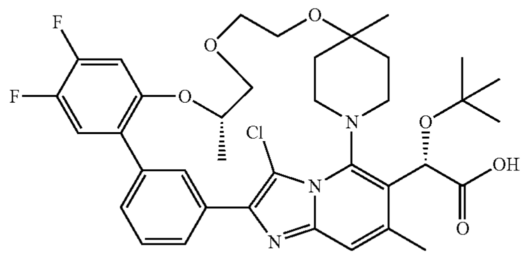 [SMILES: Cc1cc2nc3c(Cl)n2c(c1[C@H](OC(C)(C)C)C(=O)O)N1CCC(C)(CC1)OCCOC[C@H](C)Oc1cc(F)c(F)cc1-c1cccc-3c1]

(2S)-2-(tert-Butoxy)-2-[(22S)-8-chloro-17,18-difluoro-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic Acid To a solution of methyl (2S)-2-(tert-butoxy)-2-[(22S)-8-chloro-17,18-difluoro-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate (43 mg, 0.060 mmol, 1 equiv) in MeOH (1.0 mL) was added 10 N NaOH (0.121 mL, 1.21 mmol, 20 equiv). A few drops THF added to aid solubility. The mixture was heated at 70° C. for 2 h. Upon cooling to ambient temperature, the crude mixture was purified directly by reverse phase C18 chromatography (0-100% MeCN/water) to provide the Na salt of the product (27 mg, 59%) as a white solid. $^1$H NMR (400 MHz, DMSO-$d_6$) δ 8.61 (s, 1H), 7.92 (d, J=8.0 Hz, 1H), 7.56-7.43 (m, 2H), 7.40-7.31 (m, 2H), 7.12 (s, 1H), 5.46 (br. s., 1H), 4.72 (br. s., 1H), 4.11-3.53 (m, 10H), 2.43 (s, 3H), 1.88-1.88 (m, 1H), 1.83 (d, J=16.6 Hz, 2H), 1.73-1.51 (m, 2H), 1.21 (s, 3H), 1.16 (d, J=6.3 Hz, 3H), 1.13 (s, 9H); LCMS (ESI, M+1): 698.10.

Example 8

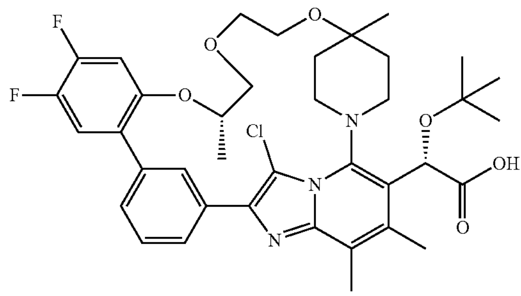 [SMILES: Cc1c([C@H](OC(C)(C)C)C(=O)O)c2n3c(Cl)c(nc3c1C)-c1cccc(c1)-c1cc(F)c(F)cc1O[C@@H](C)COCCOC1(C)CCN2CC1]

(2S)-2-(tert-Butoxy)-2-[(22S)-8-chloro-17,18-difluoro-4,5,22,28-tetramethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic Acid To a solution of methyl (2S)-2-(tert-butoxy)-2-[(22S)-17,18-difluoro-4,5,22,28-tetramethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate (100 mg, 0.145 mmol, 1 equiv) in acetonitrile (3 mL) was added NCS (23 mg, 0.538 mmol, 1.2 equiv). The solution turned yellow. After 2 h, dilute with EtOAc and wash with 1 N $Na_2S_2O_3$. The EtOAc layer was dried ($Na_2SO_4$) and concentrated in vacuo to provide the crude product.

The crude product was purified via silica gel flash chromatography (0-60% EtOAc/hexane) to provide a 2:1 mixture of the monochloride product:dichloride product (102 mg) as a yellow glass. This material was taken up in MeOH (2 mL) with a few drops of THF added to aid solubility. To this solution was added 10 N NaOH (0.28 mL, 2.81 mmol, 20 equiv). The reaction mixture was then heated at 70° C. for 2 h. Upon cooling to ambient temperature, the crude mixture was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: 45-85% B over 20 minutes, then a 5-minute hold at 100% B; Flow: 20 mL/min. Fractions containing the desired product were combined and dried via centrifugal evaporation. The major product (2S)-2-(tert-butoxy)-2-[(22S)-8-chloro-17,18-difluoro-4,5,22,28-tetramethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid (35.3 mg, 35%) was isolated. $^1$H NMR (500 MHz, DMSO-$d_6$) δ 8.61 (s, 1H), 7.97 (d, J=8.1 Hz, 1H), 7.58 (t, J=7.7 Hz, 1H), 7.52-7.46 (m, 1H), 7.42 (d, J=7.7 Hz, 1H), 7.36 (dd, J=13.2, 7.0 Hz, 1H), 5.99 (br. s., 1H), 4.72 (br. s., 1H), 4.08-3.93 (m, 2H), 3.92-3.82 (m, 1H), 3.73-3.50 (m, 6H), 3.28 (br. s., 1H), 2.50 (br. s., 3H), 2.34 (s, 3H), 1.86 (br. s., 2H), 1.76 (br. s., 1H), 1.62 (br. s., 1H), 1.22 (s, 3H), 1.20 (s, 9H), 1.15 (d, J=6.2 Hz, 3H); LCMS (ESI, M+1): 712.1. The minor product (2S)-2-(tert-butoxy)-2-[(22S)-8-chloro-17,18-difluoro-5-(hydroxymethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid was also isolated (see below).

Example 9

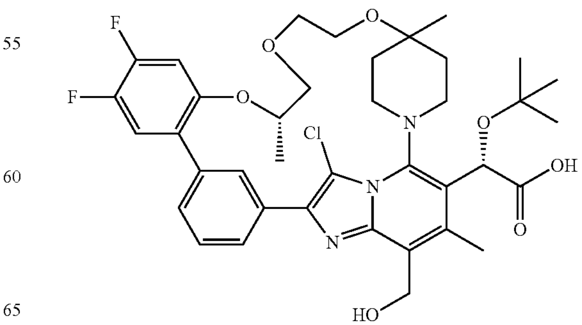

(2S)-2-(tert-Butoxy)-2-[(22S)-8-chloro-17,18-difluoro-5-(hydroxymethyl)-4,22,28-trimethyl-21,24,27-trioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic Acid Isolated from the same reaction mixture as previous (6.4 mg, 6%). LCMS (ESI, M+1): 728.1.

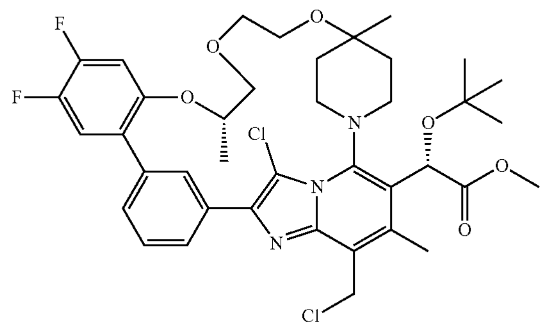 [SMILES: COC(=O)[C@@H](OC(C)(C)C)c1c(C)c(CCl)c2nc3c(Cl)n2c1N1CCC(C)(CC1)OCCOC[C@H](C)Oc1cc(F)c(F)cc1-c1cccc-3c1]

Methyl (2S)-2-(tert-butoxy)-2-[(22S)-8-chloro-5-(chloromethyl)-17,18-difluoro-4,22,28-trimethyl-21,24,27-trioxa-1,7,34-triazahexacyclo-[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate To a solution of methyl (2S)-2-(tert-butoxy)-2-[(22S)-17,18-difluoro-4,5,22,28-tetramethyl-21,24,27-trioxa-1,7,34-triazahexacyclo-[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (155 mg, 0.224 mmol, 1 equiv) in acetonitrile (5 mL) was added NCS (72 mg, 0.538 mmol, 2.4 equiv). The solution turned yellow and then orange with a precipitate forming. THF (2 mL) added to resolubalize precipitate producing an orange solution. After 5 h, the reaction was concentrated in vacuo. The crude product was purified via silica gel flash chromatography (0-60% EtOAc/hexane) to provide the product (152 mg, 89%) as a white solid. $^{1}$H NMR (400 MHz, CDCl3) δ 8.61 (s, 1H), 8.05 (d, J=7.8 Hz, 1H), 7.56 (t, J=7.8 Hz, 1H), 7.25-7.18 (m, J=10.8 Hz, 2H), 6.83 (dd, J=12.5, 6.8 Hz, 1H), 6.28 (br. s., 1H), 5.28 (d, J=11.3 Hz, 1H), 4.91 (d, J=11.8 Hz, 1H), 4.56 (br. s., 1H), 4.30-4.10 (m, 2H), 3.85-3.62 (m, 9H), 3.32 (br. s., 1H), 2.77 (s, 3H), 2.61 (br. s., 1H), 1.97 (br. s., 1H), 1.86-1.59 (m, 3H), 1.31 (s, 3H), 1.28 (s, 9H), 1.21 (d, J=6.5 Hz, 3H); $^{19}$F NMR (376 MHz, CDCl3) δ −137.21 (d, J=22.5 Hz, 1F), −148.14 (d, J=22.5 Hz, 1F); LCMS (ESI, M+1): 760.05.

Example 10

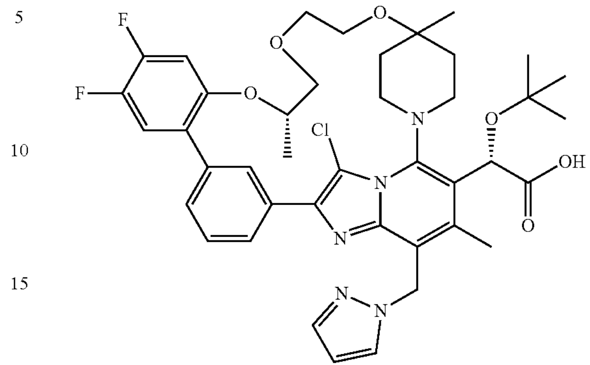

(2S)-2-(tert-Butoxy)-2-[(22S)-8-chloro-17,18-difluoro-4,22,28-trimethyl-5-(1H-pyrazol-1-ylmethyl)-21,24,27-trioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid To 1H-pyrazole (27 mg, 0.394 mmol, 10 equiv) in DMF (1 mL) was added 60% sodium hydride (16 mg, 0.394 mmol, 10 equiv). The solution became homgenous after addition. The reaction was stirred 0.5 h. To this solution was methyl (2S)-2-(tert-butoxy)-2-[(22S)-8-chloro-5-(chloromethyl)-17,18-difluoro-4,22,28-trimethyl-21,24,27-trioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (30 mg, 0.039 mmol, 1 equiv). The reaction was stirred 3 h and then warmed to 40° C. for 1 h. The reaction was then partitioned between EtOAc and water. The EtOAc layer appeared to darken during workup. The EtOAc layer was dried ($Na_2SO_4$) and concentrated in vacuo. The crude product was taken up in MeOH (1.5 mL) and water (0.5 mL) with a few drops THF added to aid solubiliity. LiOH (94 mg, 3.94 mmol, 100 equiv) was added and the mixture was heated at 60° C. for 2 h. Upon cooling to ambient temperature, the reaction mixture was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-90% B over 15 minutes, then a 5-minute hold at 100% B; Flow: 20 mL/min. Fractions containing the desired product were combined and dried via centrifugal evaporation to provide (2S)-2-(tert-butoxy)-2-[(22S)-8-chloro-17,18-difluoro-4,22,28-trimethyl-5-(1H-pyrazol-1-ylmethyl)-21,24,27-trioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid (16.6 mg, 54%). $^{1}$H NMR (500 MHz, DMSO-$d_6$) δ 8.62 (s, 1H), 7.96 (s, 1H), 7.59-7.32 (m, 7H), 6.16 (s, 1H), 6.03 (br. s., 1H), 5.69 (d, J=15.0 Hz, 1H), 5.56 (d, J=14.7 Hz, 1H), 4.72 (d, J=5.1 Hz, 1H), 4.04 (br. s., 1H), 3.97 (t, J=10.6 Hz, 1H), 3.87 (d, J=11.0 Hz, 1H), 3.73-3.49 (m, 7H), 2.23 (br. s., 3H), 1.94-1.86 (m, 2H), 1.76 (br. s., 1H), 1.62 (d, J=5.1 Hz, 1H), 1.23 (s, 3H), 1.15 (d, J=6.2 Hz, 3H), 1.13 (s, 9H); LCMS (ESI, M+1): 778.2.

Example 11

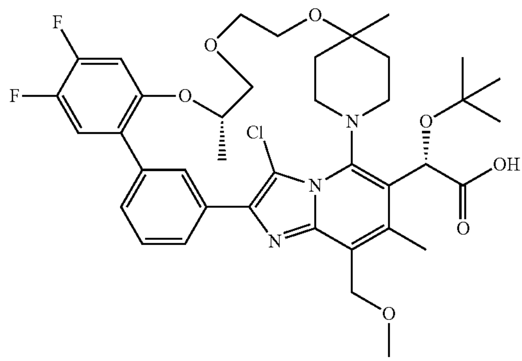 [SMILES: COCc1c(C)c([C@H](OC(C)(C)C)C(=O)O)c2n3c(Cl)c(nc13)-c1cccc(c1)-c1cc(F)c(F)cc1O[C@@H](C)COCCOC1(C)CCN2CC1]

(2S)-2-(tert-Butoxy)-2-[(22S)-8-chloro-17,18-difluoro-5-(methoxymethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic Acid To a solution of methyl (2S)-2-(tert-butoxy)-2-[(22S)-8-chloro-5-(chloromethyl)-17,18-difluoro-4,22,28-trimethyl-21,24,27-trioxa-1,7,34-triazahexacyclo-[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate (20 mg, 0.026 mmol, 1 equiv) in DMF (0.3 mL) was added NaOMe (7 mg, 0.131 mmol, 5 equiv). The reaction was stirred 3 h and then warmed to 40° C. for 1 h. Upon cooling to ambient temperature, the reaction was partitioned between EtOAc and water. The EtOAc layer appeared to darken during workup. The EtOAc layer was dried ($Na_2SO_4$) and concentrated in vacuo. The crude product was taken up in MeOH (1 mL) and water (0.5 mL) with a few drops THF added to aid solubiliity. LiOH (63 mg, 2.63 mmol, 100 equiv) was added and the mixture was heated at 60° C. for 2 h. Upon cooling to ambient temperature, the crude reaction mixture was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-90% B over 20 minutes, then a 5-minute hold at 100% B; Flow: 20 mL/min. Fractions containing the desired product were combined and dried via centrifugal evaporation to provide (2S)-2-(tert-butoxy)-2-[(22S)-8-chloro-17,18-difluoro-5-(methoxymethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic acid (6 mg, 31%). $^1$H NMR (500 MHz, DMSO-$d_6$) δ 8.62 (br. s., 1H), 8.02-7.94 (m, 1H), 7.57 (t, J=7.3 Hz, 1H), 7.49 (t, J=10.3 Hz, 1H), 7.42 (d, J=7.7 Hz, 1H), 7.36 (dd, J=13.0, 6.8 Hz, 1H), 5.73 (br. s., 1H), 4.81-4.60 (m, 3H), 4.01 (br. s., 1H), 3.87 (d, J=11.0 Hz, 2H), 3.75-3.36 (m, 10H), 2.42 (br. s., 3H), 1.85 (br. s., 2H), 1.70 (br. s., 1H), 1.58 (br. s., 1H), 1.21 (br. s., 3H), 1.18-1.12 (m, 12H); LCMS (ESI, M+1): 742.2.

Example 12

(2S)-2-(tert-Butoxy)-2-[(22S)-8-chloro-17,18-difluoro-4,22,28-trimethyl-5-(1H-1,2,3-triazol-1-ylmethyl)-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic Acid To a solution of 1H-1,2,3-triazole (27 mg, 0.394 mmol, 10 equiv) in DMF (1 mL) was added 60% sodium hydride (16 mg, 0.394 mmol, 10 equiv). The solution became homgenous after addition. The reaction was stirred 0.5 h. To this solution was added methyl (2S)-2-(tert-butoxy)-2-[(22S)-8-chloro-5-(chloromethyl)-17,18-difluoro-4,22,28-trimethyl-21,24,27-trioxa-1,7,34-triazahexacyclo-[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate (30 mg, 0.039 mmol, 1 equiv). The reaction was stirred 3 h and then warmed to 40° C. for 1 h. The reaction was then partitioned between EtOAc and water. The EtOAc layer appeared to darken during workup. The EtOAc layer was dried ($Na_2SO_4$) and concentrated in vacuo. The crude product was taken up in MeOH (1.5 mL) and water (0.5 mL) with a few drops THF added to aid solubiliity. LiOH (94 mg, 3.94 mmol, 100 equiv) was added and the mixture was heated at 60° C. for 2 h. Upon cooling to ambient temperature, the crude reaction was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-85% B over 25 minutes, then a 5-minute hold at 100% B; Flow: 20 mL/min. Fractions containing the desired product were combined and dried via centrifugal evaporation to provide the major N1 isomer (8.8 mg, 27%) and the minor N2 isomer (2.5 mg, 8%). Major isomer: $^1$H NMR (500 MHz, DMSO-$d_6$) δ 8.63 (s, 1H), 7.96 (d, J=8.1 Hz, 1H), 7.71 (s, 1H), 7.64 (s, 1H), 7.57 (t, J=7.7 Hz, 1H), 7.49 (dd, J=11.4, 9.5 Hz, 1H), 7.43 (d, J=7.7 Hz, 1H), 7.36 (dd, J=13.2, 7.0 Hz, 1H), 6.09 (br. s., 1H), 6.01 (d, J=14.7 Hz, 1H), 5.86 (d, J=14.7 Hz, 1H), 4.77-4.68 (m, 1H), 4.11-3.94 (m, 2H), 3.87 (s, 1H), 3.74-3.55 (m, 6H), 2.60 (br. s., 1H), 2.26 (s, 3H), 1.96-1.88 (m, 2H), 1.84-1.73 (m, 1H), 1.68-1.58 (m, 1H), 1.24 (s, 3H), 1.16 (d, J=6.6 Hz, 3H), 1.10 (s, 9H); LCMS (ESI, M+1): 779.2.

Example 13

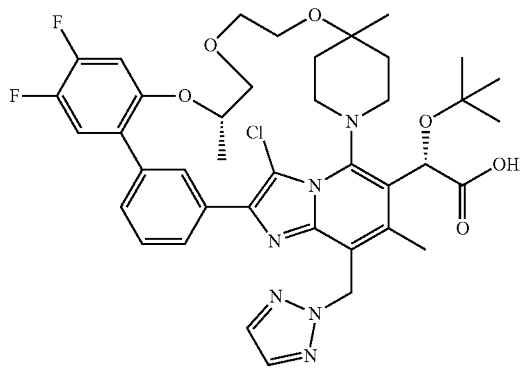 [SMILES: Cc1c([C@H](OC(C)(C)C)C(=O)O)c2n3c(Cl)c(nc3c1Cn1nccn1)-c1cccc(c1)-c1cc(F)c(F)cc1O[C@@H](C)COCCOC1(C)CCN2CC1]

(2S)-2-(tert-butoxy)-2-[(22S)-8-chloro-17,18-difluoro-4,22,28-trimethyl-5-(2H-1,2,3-triazol-2-ylmethyl)-21,24,27-trioxa-1,7,34-triazahexacyclo [26.2.2.$1^{6,9}$.$1^{10,14}$.$0^{2,7}$.$0^{15,20}$]tetratriaconta-2,4,6(34), 8,10(33),11,13,15(20),16,18-decaen-3-yl]acetic Acid Isolated in the same reaction as previous compound. $^{1}$H NMR (500 MHz, DMSO-$d_6$) δ 8.62 (s, 1H), 7.95 (d, J=7.7 Hz, 1H), 7.71 (s, 2H), 7.58 (t, J=7.9 Hz, 1H), 7.49 (dd, J=11.4, 9.5 Hz, 1H), 7.44 (d, J=7.7 Hz, 1H), 7.37 (dd, J=13.2, 6.6 Hz, 1H), 6.08 (br. s., 1H), 5.97 (s, 2H), 4.73 (br. s., 1H), 4.10-3.97 (m, 2H), 3.87 (d, J=11.4 Hz, 1H), 3.74-3.55 (m, 7H), 2.29 (br. s., 3H), 1.92 (br. s., 2H), 1.79 (br. s., 1H), 1.67-1.57 (m, 1H), 1.24 (s, 3H), 1.16 (d, J=6.6 Hz, 3H), 1.08 (s, 9H); LCMS (ESI, M+1): 779.2.

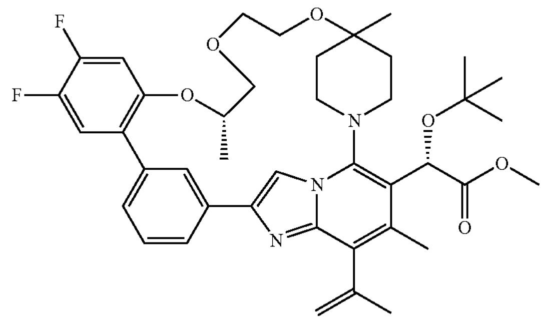 [SMILES: C=C(C)c1c(C)c([C@H](OC(C)(C)C)C(=O)OC)c2n3cc(nc13)-c1cccc(c1)-c1cc(F)c(F)cc1O[C@@H](C)COCCOC1(C)CCN2CC1]

Methyl (2S)-2-(tert-butoxy)-2-[(22S)-17,18-difluoro-4,22,28-trimethyl-5-(prop-1-en-2-yl)-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15 (20),16,18-decaen-3-yl]acetate A solution of methyl (2S)-2-(tert-butoxy)-2-[(22S)-5,8-dibromo-17,18-difluoro-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl] acetate (100 mg, 0.120 mmol, 1 equiv), 4,4,5,5-tetramethyl-2-(prop-1-en-2-yl)-1,3,2-dioxaborolane (40 mg, 0.239 mmol, 2 equiv), $Pd(OAc)_2$ (16 mg, 0.072 mmol, 0.6 equiv), Sphos (59 mg, 0.144 mmol, 1.2 equiv), and 2 M $K_3PO_4$ (0.6 mL, 1.60 mmol, 10 equiv) in dioxane (2.4 mL) was heated at 100° C. for 1 h. Upon cooling to ambient temperature, reaction mixture was diluted with EtOAc and washed with water. The organic layer was dried ($Na_2SO_4$) and concentrated in vacuo. The crude product was purified via silica gel flash column chromatography (0-100% EtOAc [2% TEA]/hexane) to provide the product (80 mg, 93%) as a white foam. LCMS (ESI, M+1): 718.5.

Example 14

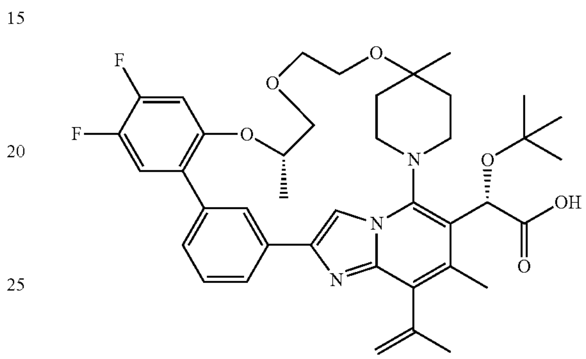

(2S)-2-(tert-Butoxy)-2-[(22S)-17,18-difluoro-4,22,28-trimethyl-5-(prop-1-en-2-yl)-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic Acid To a solution of methyl (2S)-2-(tert-butoxy)-2-[(22S)-17,18-difluoro-4,22,28-trimethyl-5-(prop-1-en-2-yl)-21,24,27-trioxa-1,7,34-triazahexacyclo[26.2.2.$1^{6,9}$.$1^{10,14}$.$0^{2,7}$.$0^{15,20}$] tetratriaconta-2,4,6(34),8,10(33),11,13,15(20),16,18-decaen-3-yl]acetate (100 mg, 0.139 mmol, 1 equiv) in MeOH (1.4 mL), water (0.5 mL), and THF (0.9 mL) was added LiOH (67 mg, 2.79 mmol, 20 equiv). The reaction was heated at 60° C. for 2 h. Upon cooling to ambient temperature, the crude reaction mixture was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-90% B over 15 minutes, then a 5-minute hold at 100% B; Flow: 20 mL/min. Fractions containing the desired product were combined and dried via centrifugal evaporation to provide the product (11.5 mg, 12%). 1H NMR (500 MHz, DMSO-$d_6$) δ 8.39 (s, 1H), 8.17 (s, 1H), 8.11 (d, J=7.7 Hz, 1H), 7.55-7.45 (m, 2H), 7.39 (dd, J=13.2, 7.0 Hz, 1H), 7.32 (d, J=7.7 Hz, 1H), 6.06 (br. s., 1H), 5.45 (s, 1H), 4.91 (s, 2H), 3.99-3.90 (m, 1H), 3.79-3.57 (m, 7H), 3.04 (d, J=6.2 Hz, 1H), 2.60 (d, J=9.9 Hz, 1H), 2.34 (s, 3H), 2.17 (s, 3H), 2.02 (d, J=13.9 Hz, 1H), 1.83-1.67 (m, 3H), 1.22 (s, 3H), 1.20 (s, 9H), 1.09 (d, J=6.2 Hz, 3H); LCMS (ESI, M+1): 704.55.

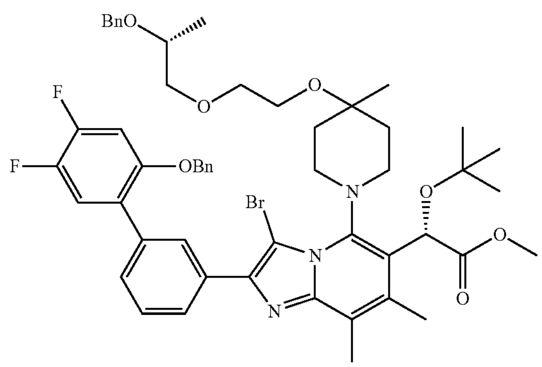 [SMILES: COC(=O)[C@@H](OC(C)(C)C)c1c(C)c(C)c2nc(-c3cccc(-c4cc(F)c(F)cc4OCc4ccccc4)c3)c(Br)n2c1N1CCC(C)(OCCOC[C@@H](C)OCc2ccccc2)CC1]

Methyl (S)-2-(2-(2'-(benzyloxy)-4',5'-difluoro-[1,1'-biphenyl]-3-yl)-5-(4-(2-((R)-2-(benzyloxy)propoxy)ethoxy)-4-methylpiperidin-1-yl)-3-bromo-7,8-dimethylimidazo[1,2-a]pyridin-6-yl)-2-(tert-butoxy)acetate To a solution of methyl (S)-2-(2-(2'-(benzyloxy)-4',5'-difluoro-[1,1'-biphenyl]-3-yl)-5-(4-(2-((R)-2-(benzyloxy)propoxy)ethoxy)-4-methylpiperidin-1-yl)-7,8-dimethylimidazo[1,2-a]pyridin-6-yl)-2-(tert-butoxy)acetate (170 mg, 0.191 mmol, 1 equiv) in MeCN (3.8 mL) was added NBS (37 mg, 0.210 mmol, 1.1 equiv). The reaction turned orange and was stirred 30 min. The reaction was then partitioned between EtOAc and 1 N $Na_2S_2O_3$. The EtOAc layer was dried ($Na_2SO_4$) and concentrated in vacuo. The crude product was purified via silica gel flash column chromatography (0-100% EtOAc [2% TEA]/hexane) to provide the product (172 mg, 93%) as an off white foam. LCMS (ESI, M+1): 968.45.

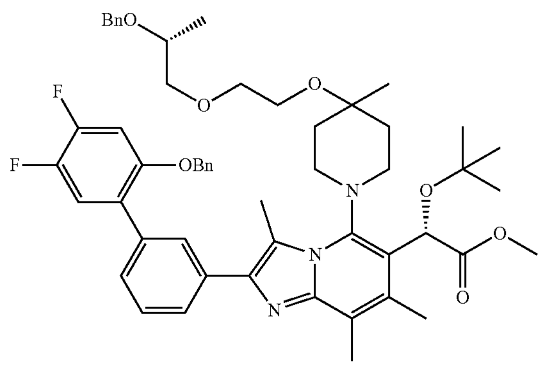 [SMILES: COC(=O)[C@@H](OC(C)(C)C)c1c(C)c(C)c2nc(-c3cccc(-c4cc(F)c(F)cc4OCc4ccccc4)c3)c(C)n2c1N1CCC(C)(OCCOC[C@@H](C)OCc2ccccc2)CC1]

Methyl (S)-2-(2-(2'-(benzyloxy)-4',5'-difluoro-[1,1'-biphenyl]-3-yl)-5-(4-(2-((R)-2-(benzyloxy)propoxy)ethoxy)-4-methylpiperidin-1-yl)-3,7,8-trimethylimidazo[1,2-a]pyridin-6-yl)-2-(tert-butoxy)acetate To a solution of methyl (S)-2-(2-(2'-(benzyloxy)-4',5'-difluoro-[1,1'-biphenyl]-3-yl)-5-(4-(2-((R)-2-(benzyloxy)propoxy)ethoxy)-4-methylpiperidin-1-yl)-3-bromo-7,8-dimethylimidazo[1,2-a]pyridin-6-yl)-2-(tert-butoxy)acetate (1.0 g, 1.03 mmol, 1 equiv), $Pd_2(dba)_3$ (53 mg, 0.052 mmol, 0.05 equiv), and RuPhos (96 mg, 0.206 mmol, 0.2 equiv) in THF (21 mL) was added $ZnMe_2$ (4.1 mL of a 1 M solution in heptane, 4.13 mmol, 4 equiv). The reaction was then heated to 60° C. for 2 h. After cooling to ambient temperature, the reaction was quenched with water and extracted with EtOAc (×1). The EtOAc layer was dried ($Na_2SO_4$) and concentrated in vacuo. The crude product was purified via silica gel flash column chromatography (0-60% EtOAc [2% TEA]/hexane) to provide the product (0.25 g, 27%) as a white foam. LCMS (ESI, M+1): 904.75.

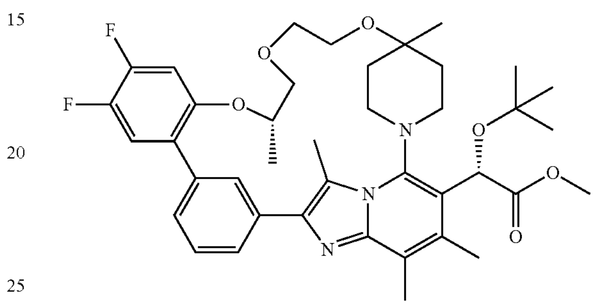

Methyl (2S)-2-(tert-butoxy)-2-[(22S)-17,18-difluoro-4,5,8,22,28-pentamethyl-21,24,27-trioxa-1,7,34-triazahexacyclo[26.2.2.1$^{6,9}$.1$^{10,14}$.0$^{2,7}$.0$^{15,20}$]tetratriaconta-2,4,6(3,4),8,10(33),11,13,15(20),16,18-decaen-3-yl]acetate To a solution of methyl (S)-2-(2-(2'-(benzyloxy)-4',5'-difluoro-[1,1'-biphenyl]-3-yl)-5-(4-(2-((R)-2-(benzyloxy)propoxy)ethoxy)-4-methylpiperidin-1-yl)-3,7,8-trimethylimidazo[1,2-a]pyridin-6-yl)-2-(tert-butoxy)acetate (0.25 g, 0.277 mmol, 1 equiv) and camphorsulfonic acid (64 mg, 0.277 mmol, 1 equiv) in THF (14 mL) was added 10% Pd/C (29 mg, 0.028 mmol, 0.1 equiv). The reaction was then put under a balloon of hydrogen and stirred 18 h. The reaction mixture was then filtered through Celite eluting with THF. The THF filtrate was concentrated in vacuo. The residue was partitioned between EtOAc and saturated aqueous $NaHCO_3$. The EtOAc layer was dried ($Na_2SO_4$) and concentrated in vacuo to provide the crude diol (0.29 g) as a yellow glass. LCMS (ESI, M+1): 724.70. The crude diol was then taken up in THF (100 mL). $PPh_3$ (80 mg, 0.305 mmol, 1.1 equiv) added followed by dropwise addition of DIAD (0.059 mL, 0.305 mmol, 1.1 equiv). The solution quickly became dark yellow and then slowly lightened over 1 h. After stirring 1 h, the reaction was diluted with EtOAc and washed with water. The organic layer was dried ($Na_2SO_4$) and concentrated in vacuo. The crude product was purified via silica gel flash column chromatography (0-60% EtOAc [2% TEA]/hexane) to provide the product (0.058 g, 30%) as a white foam. $^1$H NMR (500 MHz, CDCl3) δ 8.00 (d, J=7.9 Hz, 1H), 7.94 (s, 1H), 7.56 (t, J=7.6 Hz, 1H), 7.27 (br. s., 1H), 7.21 (dd, J=10.8, 9.5 Hz, 1H), 6.85 (dd, J=12.5, 6.7 Hz, 1H), 6.32 (br. s., 1H), 4.66 (t, J=6.1 Hz, 1H), 3.92-3.58 (m, 13H), 3.04 (s, 3H), 2.61 (br. s., 3H), 2.38 (br. s., 3H), 1.99-1.89 (m, J=10.9 Hz, 2H), 1.70-1.62 (m, 2H), 1.31 (br. s., 3H), 1.26 (s, 9H), 1.20 (d, J=6.3 Hz, 3H); LCMS (ESI, M+1): 706.40.

Example 15

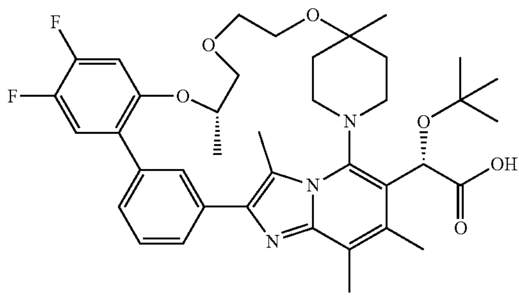 [SMILES: Cc1c([C@H](OC(C)(C)C)C(=O)O)c2n3c(C)c(nc3c1C)-c1cccc(c1)-c1cc(F)c(F)cc1O[C@@H](C)COCCOC1(C)CCN2CC1]

(2S)-2-(tert-Butoxy)-2-[(22S)-17,18-difluoro-4,5,8,22,28-pentamethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic Acid To a solution of methyl (2S)-2-(tert-butoxy)-2-[(22S)-17,18-difluoro-4,5,8,22,28-pentamethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate (58 mg, 0.082 mmol, 1 equiv) in MeOH (2 mL) was added 10 N NaOH (0.16 mL, 1.64 mmol, 20 equiv). The reaction was heated at 70° C. After cooling to ambient temperature, the crude reaction mixture was purified by C18 column chromatography (5-100% MeCN/water) to provide the sodium salt of the product (29 mg, 46%) as a white solid. $^{1}$H NMR (400 MHz, DMSO-$d_6$) δ 7.88 (d, J=7.8 Hz, 1H), 7.85 (s, 1H), 7.53 (t, J=7.7 Hz, 1H), 7.48-7.37 (m, 2H), 7.32 (d, J=7.8 Hz, 1H), 5.36 (s, 1H), 4.83 (t, J=5.8 Hz, 1H), 4.20 (d, J=5.5 Hz, 1H), 3.77-3.51 (m, 8H), 2.92 (s, 3H), 2.43 (d, J=7.0 Hz, 1H), 2.39 (s, 3H), 2.30 (s, 3H), 1.91-1.79 (m, 1H), 1.70 (d, J=7.0 Hz, 1H), 1.60-1.45 (m, 2H), 1.24 (br. s., 3H), 1.09 (s, 9H), 0.87-0.82 (m, 3H); LCMS (ESI, M+1): 692.45.

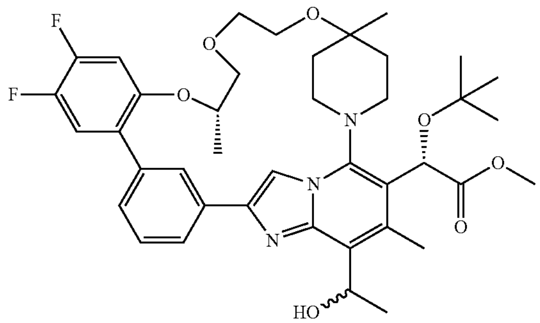 [SMILES: COC(=O)[C@@H](OC(C)(C)C)c1c(C)c(C(C)O)c2nc3cn2c1N1CCC(C)(CC1)OCCOC[C@H](C)Oc1cc(F)c(F)cc1-c1cccc-3c1]

Methyl (2S)-2-(tert-butoxy)-2-[(22S)-17,18-difluoro-5-(1-hydroxyethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate To a solution of methyl (2S)-2-(tert-butoxy)-2-[(22S)-17,18-difluoro-5-formyl-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate (150 mg, 0.213 mmol, 1 equiv) and (1-methylpiperidin-2-yl)methanol (27 mg, 0.213 mmol, 1 equiv) in toluene (11 mL) was added $ZnMe_2$ (0.85 mL of a 1 M solution in heptane, 0.850 mmol, 4 equiv). The reaction turned orange. After 2 h, the reaction was partitioned between saturated aqueous $NH_4Cl$ and DCM. The DCM layer was dried ($Na_2SO_4$) and concentrated in vacuo. The crude product was purified via silica gel flash chromatography (0-100% EtOAc/hexane) to provide the product (120 mg, 78%) as an 2:1 mixture of diastereomers. LCMS (ESI, M+1): 722.40.

Example 16

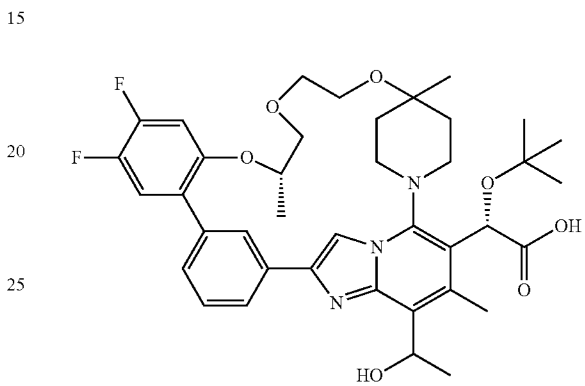

(2S)-2-(tert-Butoxy)-2-[(22S)-17,18-difluoro-5-(1-hydroxyethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic Acid, 2 Diastereomers To a 2:1 mixture of diastereomers of methyl 2S)-2-(tert-butoxy)-2-[(22S)-17,18-difluoro-5-(1-hydroxyethyl)-4,22,28-trimethyl-21,24,27-trioxa-1,7,34-triazahexacyclo[26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetate (50 mg, 0.069 mmol, 1 equiv) in THF (0.8 mL), MeOH (1.2 mL), and water (0.4 mL) was added LiOH (100 mg, 4.18 mmol, 60 equiv). The reaction was then heated at 60° C. for 2 h. Upon cooling to ambient temperature, the crude reaction was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 22 minutes, then a 5-minute hold at 100% B; Flow: 20 mL/min. Fractions containing the desired product were combined and dried via centrifugal evaporation. Diastereomer 1 (8.3 mg, 17%) and diasteromer 2 (17.3 mg, 35%) were isolated. Diastereomer 1: $^{1}$H NMR (500 MHz, DMSO-$d_6$) δ 8.42 (s, 1H), 8.18 (s, 1H), 8.11 (d, J=8.1 Hz, 1H), 7.58-7.45 (m, 2H), 7.43-7.32 (m, 2H), 6.08 (br. s., 1H), 5.43 (br. s., 1H), 4.91 (d, J=6.6 Hz, 1H), 4.00-3.86 (m, 1H), 3.80-3.57 (m, 8H), 3.03 (d, J=8.4 Hz, 1H), 2.39 (s, 3H), 2.02 (d, J=13.9 Hz, 1H), 1.83-1.66 (m, 3H), 1.52 (d, J=6.6 Hz, 3H), 1.22 (s, 3H), 1.20 (s, 9H), 1.09 (d, J=6.2 Hz, 3H); LCMS (ESI, M+1): 708.2. Diastereomer 2: $^{1}$H NMR (500 MHz, DMSO-$d_6$) δ 8.41 (s, 1H), 8.18 (s, 1H), 8.11 (d, J=8.1 Hz, 1H), 7.54 (t, J=7.7 Hz, 1H), 7.49 (dd, J=11.4, 9.5 Hz, 1H), 7.39 (dd, J=13.2, 7.0 Hz, 1H), 7.35 (d, J=7.7 Hz, 1H), 6.08 (br. s., 1H), 5.54 (d, J=6.2 Hz, 1H), 4.96-4.86 (m, 1H), 3.94 (t, J=10.3 Hz, 1H), 3.80-3.72 (m, 2H), 3.71-3.55 (m, 5H), 3.00 (d, J=9.2 Hz, 1H), 2.58 (d, J=10.6 Hz, 1H), 2.44 (s, 3H), 2.03 (d, J=13.2 Hz, 1H), 1.82-1.65 (m, 3H), 1.53 (d, J=6.6 Hz, 3H), 1.22 (s, 3H), 1.20 (s, 9H), 1.09 (d, J=6.2 Hz, 3H); LCMS (ESI, M+1): 708.2.

Example 17

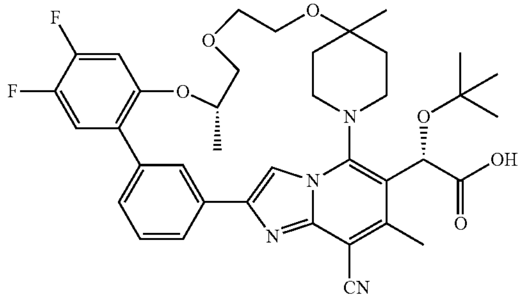 [SMILES: Cc1c([C@H](OC(C)(C)C)C(=O)O)c2n3cc(nc3c1C#N)-c1cccc(c1)-c1cc(F)c(F)cc1O[C@@H](C)COCCOC1(C)CCN2CC1]

(2S)-2-(tert-Butoxy)-2-[(22S)-5-cyano-17,18-difluoro-4,22,28-trimethyl-21,24,27-trioxa-1,7,34-triazahexacyclo$[26.2.2.1^{6,9}.1^{10,14}.0^{2,7}.0^{15,20}]$tetratriaconta-2,4,6(34),8,10(33),11,13,15(20),16,18-decaen3-yl]acetic Acid A solution of methyl (2S)-2-(tert-butoxy)-2-[(22S)-5,8-dibromo-17,18-difluoro-4,22,28-trimethyl-21,24,27-trioxa-1,7,34-triazahexacyclo$[26.2.2.1^{6,9}.1^{10,14}.0^{2,7}.0^{15,20}]$tetratriaconta-2,4,6(34),8,10(33),11,13,15(20),16,18-decaen-3-yl] acetate (30 mg, 0.036 mmol, 1 equiv), $Pd(dppf)_2$ (29 mg, 0.036 mmol, 1 equiv), and $Zn(CN)_2$ (8.4 mg, 72 mmol, 2 equiv) in degassed DMA (0.18 mL) was heated at 150° C. for 2 h. More $Pd(dppf)_2$ (29 mg, 0.036 mmol, 1 equiv) and $Zn(CN)_2$ (8.4 mg, 72 mmol, 2 equiv) was added and the reaction was heated at 150° C. for a further 18 h. Upon cooling to ambient temperature, MeOH (0.7 mL), THF (0.5 mL), and water (0.2 mL) were added followed by LiOH (100 mg, 4.18 mmol, 116 equiv). The reaction was then heated at 60° C. for 2 h. Upon cooling to ambient temperature, the crude reaction was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 22 minutes, then a 5-minute hold at 100% B; Flow: 20 mL/min. Fractions containing the desired product were combined and dried via centrifugal evaporation. The product (4.0 mg, 16%) was isolated. $^{1}H$ NMR (500 MHz, DMSO-$d_6$) δ 8.43 (s, 1H), 8.26 (s, 1H), 8.16 (d, J=7.7 Hz, 1H), 7.56 (t, J=7.7 Hz, 1H), 7.51 (dd, J=11.4, 9.5 Hz, 1H), 7.41-7.35 (m, 2H), 5.90 (s, 1H), 4.92 (d, J=5.5 Hz, 1H), 3.95-3.85 (m, 1H), 3.81-3.75 (m, 1H), 3.73-3.56 (m, 6H), 3.14 (br. s., 1H), 2.65 (s, 3H), 2.63 (br. s., 1H), 2.00 (d, J=12.8 Hz, 1H), 1.85-1.79 (m, 1H), 1.78-1.65 (m, 2H), 1.22 (s, 3H), 1.19 (s, 9H), 1.09 (d, J=6.2 Hz, 3H); LCMS (ESI, M+1): 689.2.

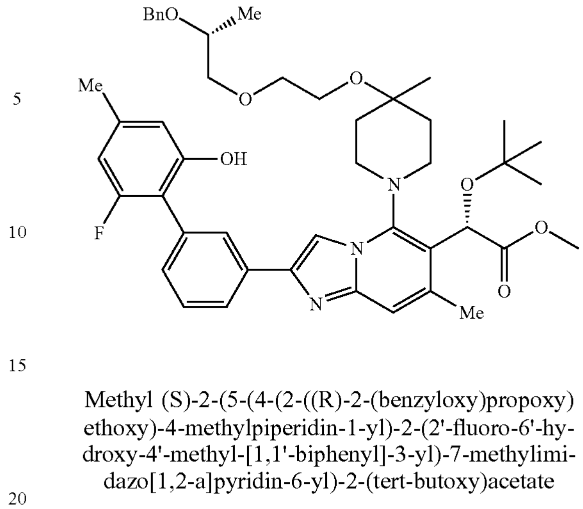

Methyl (S)-2-(5-(4-(2-((R)-2-(benzyloxy)propoxy)ethoxy)-4-methylpiperidin-1-yl)-2-(2'-fluoro-6'-hydroxy-4'-methyl-[1,1'-biphenyl]-3-yl)-7-methylimidazo[1,2-a]pyridin-6-yl)-2-(tert-butoxy)acetate To a solution of methyl (S)-2-(5-(4-(2-((R)-2-(benzyloxy)propoxy)ethoxy)-4-methylpiperidin-1-yl)-2-(3-bromophenyl)-7,8-dimethylimidazo[1,2-a]pyridin-6-yl)-2-(tert-butoxy)acetate (0.20 g, 0.271 mmol, 1 equiv), $Pd(OAc)_2$ (6 mg, 0.027 mmol, 0.1 equiv), SPhos (22 mg, 0.054 mmol, 0.2 equiv), and $Cs_2CO_3$ (221 mg, 0.679 mmol, 2.5 equiv) in degassed DMF (2.5 mL) and water (0.25 mL) at 100° C. was added dropwise a solution of (2-fluoro-6-hydroxy-4-methylphenyl)boronic acid (92 mg, 0.543 mmol, 2 equiv) in DMF (1 mL). After 5 min, LCMS shows complete conversion. After cooling to ambient temperature, the reaction mixture was partitioned between EtOAc and saturated aqueous $NH_4Cl$. The EtOAc layer was dried ($Na_2SO_4$) and concentrated in vacuo. The crude product was purified by silica gel flash chromatography (0-100% EtOAc/hexane) to provide to product (150 mg, 71%) as a white foam. LCMS (ESI, M+1): 782.50.

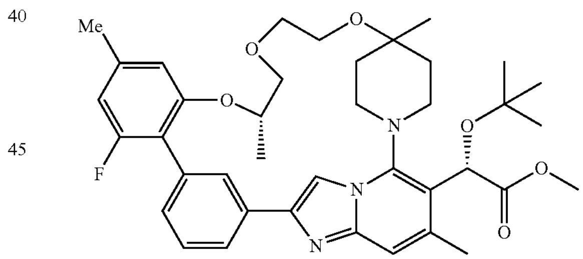

Methyl (2S)-2-(tert-butoxy)-2-[(22S)-16-fluoro-4,18,22,28-tetramethyl-21,24,27-trioxa-1,7,34-triazahexacyclo$[26.2.2.1^{6,9}.1^{10,14}.0^{2,7}.0^{15,20}]$tetratriaconta-2,4,6(34),8,10(33),11,13,15(20),16,18-decaen-3-yl] acetate To a solution of methyl (S)-2-(5-(4-(2-((R)-2-(benzyloxy)propoxy)ethoxy)-4-methylpiperidin-1-yl)-2-(2'-fluoro-6'-hydroxy-4'-methyl-[1,1'-biphenyl]-3-yl)-7-methylimidazo[1,2-a]pyridin-6-yl)-2-(tert-butoxy)acetate (200 mg, 0.256 mmol, 1 equiv) and camphorsulfonic acid (59 mg, 0.256 mmol, 1 equiv) in THF (2.6 mL) was added 10% Pd/C (27 mg, 0.026 mmol, 0.1 equiv). The reaction was then stirred under a balloon of hydrogen for 18 h. Upon completion, the reaction mixture was filtered through Celite eluting with THF. The combined filtrate was concentrated in vacuo to provide methyl (S)-2-(tert-butoxy)-2-(2-(2'-fluoro-6'-hydroxy-4'-methyl-[1,1'-biphenyl]-3-yl)-5-(4-(2-((R)-2-hydroxypropoxy)ethoxy)-4-methylpiperidin-1-yl)-7-methylimidazo[1,2-a]pyridin-6-yl)acetate. This material was taken up in THF (6 mL) and $PPh_3$ (81 mg, 0.307, 1.2 equiv) was added. To this mixture was added DIAD (0.060 mL, 0.307 mmol, 1.2 equiv). After stirring 0.5 h, the reaction was diluted with DCM and washed with saturated aqueous $NaHCO_3$. The DCM layer was dried ($Na_2SO_4$) and concentrated in vacuo. The crude product was purified by silica gel flash chromatography (0-100% EtOAc [2% TEA]/hexane) to provide to product (10 mg, 6%) as a white foam. $^1$H NMR (400 MHz, $CDCl_3$) δ 8.32 (s, 1H), 8.21 (d, J=7.8 Hz, 1H), 8.13 (s, 1H), 7.52 (t, J=7.7 Hz, 1H), 7.32 (s, 1H), 7.26 (d, J=2.3 Hz, 1H), 6.87 (dd, J=12.2, 6.9 Hz, 1H), 6.06 (s, 1H), 4.66-4.55 (m, 1H), 4.04 (t, J=10.7 Hz, 1H), 3.93 (dd, J=12.0, 7.3 Hz, 2H), 3.84 (t, J=10.7 Hz, 1H), 3.69 (s, 3H), 3.66 (d, J=3.0 Hz, 1H), 3.62-3.56 (m, 2H), 3.05 (d, J=9.3 Hz, 1H), 2.67 (d, J=8.5 Hz, 1H), 2.47 (s, 3H), 2.02-1.88 (m, 2H), 1.85-1.69 (m, 2H), 1.58 (s, 3H), 1.26 (s, 9H), 1.13 (d, J=6.3 Hz, 3H); LCMS (ESI, M+1): 674.45.

Example 18

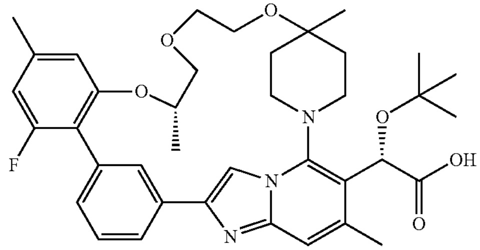 [SMILES: Cc1cc(F)c2c(c1)O[C@@H](C)COCCOC1(C)CCN(CC1)c1c([C@H](OC(C)(C)C)C(=O)O)c(C)cc3nc(cn13)-c1cccc-2c1]

(2S)-2-(tert-Butoxy)-2-[(22S)-16-fluoro-4,18,22,28-tetramethyl-21,24,27-trioxa-1,7,34-triazahexacyclo [26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic Acid To a solution of methyl (2S)-2-(tert-butoxy)-2-[(22S)-16-fluoro-4,18,22,28-tetramethyl-21,24,27-trioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (10 mg, 0.015 mmol, 1 equiv) in MeOH (0.7 mL), water (0.2 mL), and THF (0.5 mL) was added LiOH (11 mg, 0.445 mmol, 30 equiv). The reaction was heated at 60° C. for 2 h. Upon cooling to ambient temperature, the crude mixture was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation. The product (3.9 mg, 40%) was isolated. $^1$H NMR (500 MHz, DMSO-$d_6$) δ 8.15 (d, J=4.0 Hz, 2H), 8.08 (d, J=7.7 Hz, 1H), 7.46 (t, J=7.7 Hz, 1H), 7.28-7.21 (m, 2H), 6.92 (s, 1H), 6.72 (d, J=10.6 Hz, 1H), 5.88 (s, 1H), 4.91 (br. s., 1H), 4.01-3.91 (m, 1H), 3.75-3.55 (m, 7H), 3.12 (br. s., 1H), 2.57 (d, J=11.7 Hz, 1H), 2.41 (s, 3H), 2.37 (s, 3H), 1.98 (d, J=13.6 Hz, 1H), 1.82-1.76 (m, 1H), 1.74-1.66 (m, 2H), 1.21 (s, 3H), 1.18 (s, 9H), 1.08 (d, J=6.2 Hz, 3H); LCMS (ESI, M+1): 660.2.

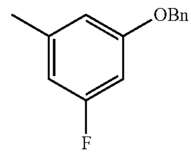 [SMILES: Cc1cc(F)cc(OCc2ccccc2)c1]

1-(Benzyloxy)-3-fluoro-5-methylbenzene

To a solution of 3-fluoro-5-methylphenol (25 g, 198 mmol, 1 equiv) in MeCN (400 mL) was added BnCl (27.6 mL, 238 mmol, 1.2 equiv) followed by $K_2CO_3$ (38.4 g, 277 mmol, 1.4 equiv). The yellow slurry was heated to reflux for 2 h. Upon cooling to ambient temperature, the reaction mixture was filtered. The filtrate was diluted with ether and washed with 1 N NaOH. The ether layer was dried (MgSO4) and concentrated in vacuo to provide the product (30.4 g, 71%) as a yellow oil. 1H NMR (500 MHz, $CDCl_3$) δ 7.47-7.39 (m, 4H), 7.38-7.33 (m, 1H), 6.62 (d, J=0.5 Hz, 1H), 6.56-6.50 (m, 2H), 5.05 (s, 2H), 2.34 (s, 3H).

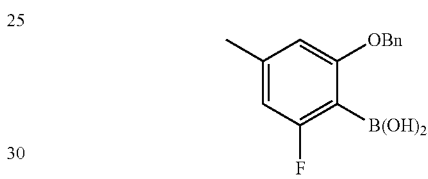

(2-(Benzyloxy)-6-fluoro-4-methylphenyl)boronic Acid

A solution of 1-(benzyloxy)-3-fluoro-5-methylbenzene (5 g, 23.1 mmol, 1 equiv) and TMEDA (3.5 mL, 23.1 mmol, 1 equiv) in THF (100 mL) was cooled to −78° C. (IPA/dry ice). s-BuLi (18.2 mL of a 1.4 M solution in cyclohexane, 25.4 mmol, 1.1 equiv) was added dropwise with a syringe over 60 sec. After 1.5 h, the reaction is a dark orange brown color. Triisopropyl borate (6.4 mL, 27.7 mmol, 1.2 equiv) added and the reaction was stirred 1.5 h. The reaction was quenched while cold with 1 N HCl (50 mL) and then partitioned between EtOAc and water. The EtOAc was dried ($Na_2SO_4$) and concentrated in vacuo. The crude product was triturated in hexane and the resultant solid was filtered to provide the product (4.2 g, 70%) as a free flowing white solid. $^1$H NMR (400 MHz, $CDCl_3$) δ 7.50-7.32 (m, 5H), 6.67 (s, 1H), 6.61 (d, J=11.5 Hz, 1H), 6.21 (d, J=7.5 Hz, 2H), 5.15 (s, 2H), 4.14 (q, J=7.0 Hz, 2H), 2.38 (s, 3H).

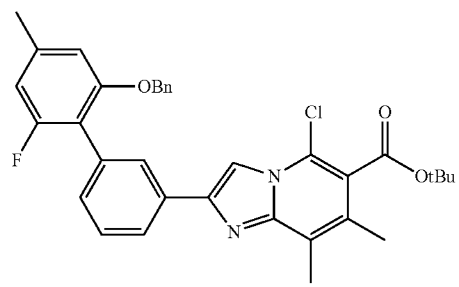 [SMILES: Cc1cc(F)c(-c2cccc(-c3cn4c(Cl)c(C(=O)OC(C)(C)C)c(C)c(C)c4n3)c2)c(OCc2ccccc2)c1]

tert-Butyl 2-(2'-(benzyloxy)-6'-fluoro-4'-methyl-[1,1'-biphenyl]-3-yl)-5-chloro-7,8-dimethylimidazo[1,2-a]pyridine-6-carboxylate tert-Butyl 2-(3-bromophenyl)-5-chloro-7,8-dimethylimidazo[1,2-a]pyridine-6-carboxylate (1 g, 2.30 mmol, 1 equiv), (2-(benzyloxy)-6-fluoro-4-methylphenyl)boronic acid (0.94 g, 2.52 mmol, 1.1 equiv), $PdCl_2$(dppf) (0.168 g, 0.229 mmol, 0.1 equiv), and $Cs_2CO_2$ (1.50 g, 4.59 mmol, 2 equiv) were dissolved in DMF (41.7 ml) and water (4.17 ml). The reaction mixture was degassed by bubbling $N_2$ through the mixture for 10 min. The reaction was then heated at 60° C. for 2 h. Upon cooling to ambient temperature the reaction was partitioned between EtOAc and water. The EtOAc layer was dried ($Na_2SO_4$) and concentrated in vacuo to provide the crude product. The crude product was purified by flash column silica gel chromatography (0-100% EtOAc/hex) to provide the product (1.0 g, 1.751 mmol, 76% yield) as a solid. LCMS (ESI, M+1): 571.25.

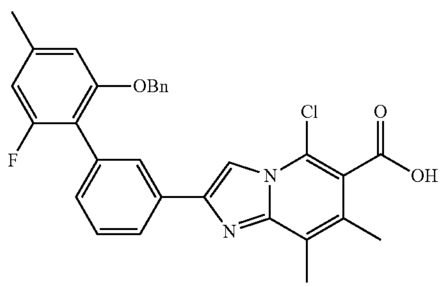 [SMILES: Cc1cc(F)c(-c2cccc(-c3cn4c(Cl)c(C(=O)O)c(C)c(C)c4n3)c2)c(OCc2ccccc2)c1]

2-(2'-(Benzyloxy)-6'-fluoro-4'-methyl-[1,1'-biphenyl]-3-yl)-5-chloro-7,8-dimethylimidazo[1,2-a]pyridine-6-carboxylic Acid tert-Butyl 2-(2'-(benzyloxy)-6-fluoro-4'-methyl-[1,1'-biphenyl]-3-yl)-5-chloro-7,8-dimethylimidazo[1,2-a]pyridine-6-carboxylate (4.1 g, 7.18 mmol, 1 equiv) was taken up in 4 N HCl in dioxane (200 mL). After 30 min, the reaction became a white slurry. Stir 16 h. The reaction is now a clear pale tan solution. Heat at 50° C. for 3 h. Upon cooling to ambient temperature, the reaction mixture was added slowly to vogorously stirring ether (1 L). After 10 min, the white solid was filtered to provide the product (3.4 g, 92%). LCMS (ESI, M+1): 515.20.

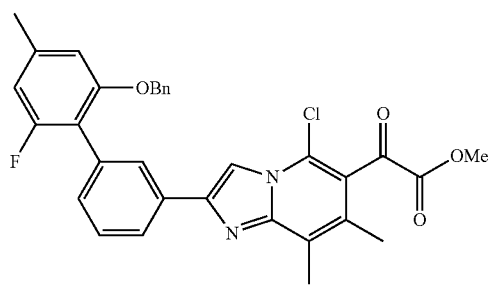 [SMILES: COC(=O)C(=O)c1c(C)c(C)c2nc(-c3cccc(-c4c(F)cc(C)cc4OCc4ccccc4)c3)cn2c1Cl]

Methyl 2-(2-(2'-(benzyloxy)-6'-fluoro-4'-methyl-[1,1'-biphenyl]-3-yl)-5-chloro-7,8-dimethylimidazo[1,2-a]pyridin-6-yl)-2-oxoacetate To a solution of 2-(2'-(benzyloxy)-6'-fluoro-4'-methyl-[1,1'-biphenyl]-3-yl)-5-chloro-7,8-dimethylimidazo[1,2-a]pyridine-6-carboxylic acid, HCl (3.4 g, 6.17 mmol, 1 equiv) and DIPEA (3.2 mL, 18.5 mmol, 3 equiv) in DCE (62 mL) was added HATU (2.81 g, 7.40 mmol, 1.2 equiv). After 1 h, 1-(cyanomethyl)tetrahydro-1H-thiophen-1-ium, hexafluorophosphate salt (2.36 h, 8.63 mmol, 1.4 equiv) added. The reaction was stirred for 18 h at which point more 1-(cyanomethyl)tetrahydro-1H-thiophen-1-ium, hexafluorophosphate salt (2.36 h, 8.63 mmol, 1.4 equiv) and DIPEA (3.2 mL, 18.5 mmol, 3 equiv) were added. After stirring 24 h, the reaction was diluted with EtOAc and washed with water, saturated aqueous sodium bicarbonate, dried ($Na_2SO_4$), and concentrated in vacuo to provide a tan foam. The crude sulfur ylide was taken up in THF (50 mL) and then diluted with MeOH (300 mL) and water (30 mL). $KHSO_5$ monohydrate (3.15 g, 18.5 mmol, 3 equiv, see *Eur. J. Org. Chem.* 2002, 3429 for preparation) was then added. After 18 h, more $KHSO_5$ monohydrate (3.15 g, 18.5 mmol, 3 equiv) was added. After 24 h, the reaction was diluted with THF and filtered. The filtrate was concentrated in vacuo. The residue was added to saturated aqueous sodium bicarbonate and extracted with DCM (×2). The combined DCM extracts were dried ($Na_2SO_4$) and concentrated in vacuo. The crude product was purified by flash column silica gel chromatography (5-100% EtOAc/hex) to provide the product (1.9 g, 55% yield) as a yellow solid. $^1H$ NMR (400 MHz, $CDCl_3$) δ 8.11 (s, 1H), 8.02 (d, J=7.5 Hz, 1H), 7.97 (s, 1H), 7.56-7.49 (m, 1H), 7.48-7.44 (m, 1H), 7.34-7.20 (m, 5H), 6.73-6.67 (m, 2H), 5.07 (s, 2H), 3.99 (s, 3H), 2.67 (s, 3H), 2.40 (s, 3H), 2.29 (s, 3H); LCMS (ESI, M+1): 557.20.

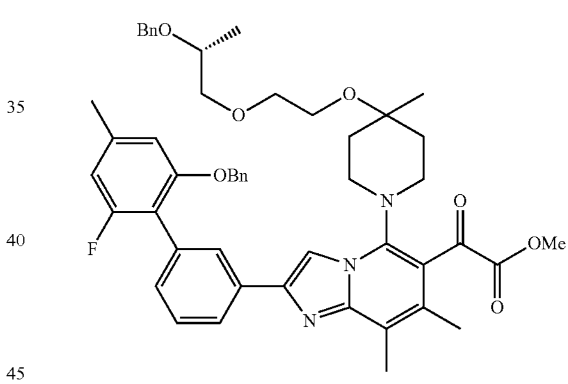

Methyl (R)-2-(2-(2'-(benzyloxy)-6'-fluoro-4'-methyl-[1,1'-biphenyl]-3-yl)-5-(4-(2-(2-(benzyloxy)propoxy)ethoxy)-4-methylpiperidin-1-yl)-7,8-dimethylimidazo[1,2-a]pyridin-6-yl)-2-oxoacetate To a solution of methyl 2-(2-(2'-(benzyloxy)-6'-fluoro-4'-methyl-[1,1'-biphenyl]-3-yl)-5-chloro-7,8-dimethylimidazo[1,2-a]pyridin-6-yl)-2-oxoacetate (1.9 g, 3.41 mmol, 1 equiv) in DMF (34 mL) was added (R)-4-(2-(2-(benzyloxy)propoxy)ethoxy)-4-methylpiperidine (1.26 g, 4.09 mmol, 1.2 equiv) and DIPEA (1.43 mL, 8.19 mmol, 2.4 equiv). After stirring 18 h, more (R)-4-(2-(2-(benzyloxy)propoxy)ethoxy)-4-methylpiperidine (0.2 g) was added. After stirring 24 h, more (R)-4-(2-(2-(benzyloxy)propoxy)ethoxy)-4-methylpiperidine (0.2 g) was added. After 3 h, the reaction was diluted with EtOAc and washed with water (×2), brine (×1), dried ($Na_2SO_4$), and concentrated in vacuo. The crude product was purified by flash column silica gel chromatography (0-100% EtOAc/hex) to provide the product (1.93 g, 68% yield) as a yellow solid. LCMS (ESI, M+1): 828.35.

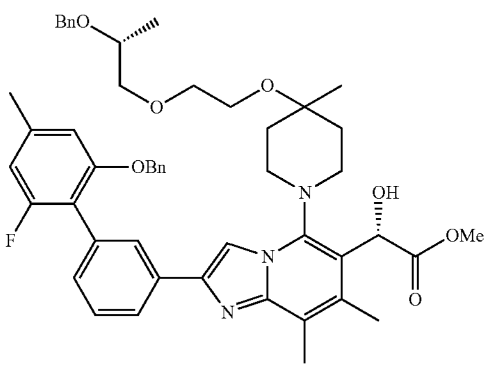 [SMILES: COC(=O)[C@@H](O)c1c(C)c(C)c2nc(-c3cccc(-c4c(F)cc(C)cc4OCc4ccccc4)c3)cn2c1N1CCC(C)(OCCOC[C@@H](C)OCc2ccccc2)CC1]

Methyl (S)-2-(2-(2'-(benzyloxy)-6'-fluoro-4'-methyl-[1,1'-biphenyl]-3-yl)-5-(4-(2-((R)-2-(benzyloxy)propoxy)ethoxy)-4-methylpiperidin-1-yl)-7,8-dimethylimidazo[1,2-a]pyridin-6-yl)-2-hydroxyacetate To a solution of (R)-methyl 2-(2-(2'-(benzyloxy)-6'-fluoro-4'-methyl-[1,1'-biphenyl]-3-yl)-5-(4-(2-(2-(benzyloxy)propoxy)ethoxy)-4-methylpiperidin-1-yl)-7,8-dimethylimidazo[1,2-a]pyridin-6-yl)-2-oxoacetate (1.93 g, 2.33 mmol, 1 equiv) and (R)-5,5-diphenyl-2-methyl-3,4-propano-1,3,2-oxazaborlidine (0.65 g, 2.33 mmol, 1 equiv) in toluene (47 mL) at −78° C. (IPA/$CO_2$) was added catecholborane (1.00 mL of a 50% solution in toluene, 4.66 mmol, 2 equiv). The reaction was then transferred to a freezer at (−20° C.). After 7 d, the reaction was diluted with EtOAc and washed with 10% $K_2CO_3$, brine, dried ($Na_2SO_4$) and concentrated in vacuo. The crude product was purified by flash column silica gel chromatography (10-100% EtOAc/hex) to provide the product (1.9 g, 98% yield) as a white solid. LCMS (ESI, M+1): 830.35.

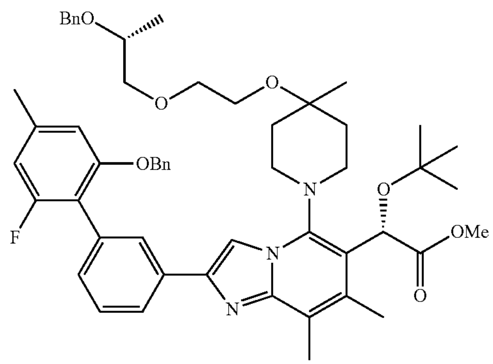 [SMILES: COC(=O)[C@@H](OC(C)(C)C)c1c(C)c(C)c2nc(-c3cccc(-c4c(F)cc(C)cc4OCc4ccccc4)c3)cn2c1N1CCC(C)(OCCOC[C@@H](C)OCc2ccccc2)CC1]

Methyl (S)-2-(2-(2'-(benzyloxy)-6'-fluoro-4'-methyl-[1,1'-biphenyl]-3-yl)-5-(4-(2-((R)-2-(benzyloxy)propoxy)ethoxy)-4-methylpiperidin-1-yl)-7,8-dimethylimidazo[1,2-a]pyridin-6-yl)-2-(tert-butoxy)acetate To a solution of (9-methyl 2-(2-(2'-(benzyloxy)-6'-fluoro-4'-methyl-[1,1'-biphenyl]-3-yl)-5-(4-(2-((R)-2-(benzyloxy)propoxy)ethoxy)-4-methylpiperidin-1-yl)-7,8-dimethylimidazo[1,2-a]pyridin-6-yl)-2-hydroxyacetate (1.9 g, 2.29 mmol, 1 equiv) in tert-BuOAc (114 mL) was added 70% perchloric acid (0.59 mL, 6.87 mmol, 3 equiv). After 2 h, the reaction was diluted with EtOAc and washed with 10% $K_2CO_3$, dried ($Na_2SO_4$), and concentrated in vacuo. The crude product was purified by flash column silica gel chromatography (0-100% EtOAc [2% TEA]/hex) to provide the product (1.04 g, 51% yield) as a white solid. LCMS (ESI, M+1): 886.45.

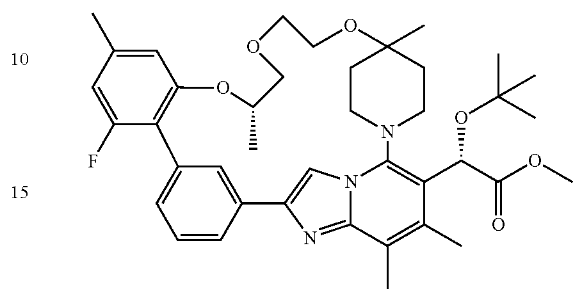

Methyl (2S)-2-(tert-butoxy)-2-((6S,Z)-46-fluoro-14,27,28,44,6-pentamethyl-5,8,11-trioxa-2 (5,2)-imidazo[1,2-a]pyridina-1(1,4)-piperidina-3(1,3),4(1,2)-dibenzenacycloundecaphane-26-yl)acetate To a solution of (9-methyl 2-(5-(4-(2-((R)-2-(benzyloxy)propoxy)ethoxy)-4-methylpiperidin-1-yl)-2-(2'-fluoro-6'-hydroxy-4'-methyl-[1,1'-biphenyl]-3-yl)-7,8-dimethylimidazo[1,2-a]pyridin-6-yl)-2-(tert-butoxy)acetate (0.53 g, 0.67 mmol, 1 equiv) and camphorsulfonic acid (0.16 g, 0.67 mmol, 1 equiv) in THF (33 mL) was added 10% Pd/C (71 mg, 0.067 mmol, 0.1 equiv). Reaction put under a balloon of hydrogen. After 18 h, the reaction was filtered through celite and the filtrate was concentrated in vacuo. The crude product was taken up in THF (100 mL). $PPh_3$ (0.210 g, 0.80 mmol, 1.2 equiv) and DIAD (0.16 mL, 0.80 mmol, 1.2 equiv) were added. After 1 h, the reaction was added to water and extracted with DCM (×3). The combined DCM extracts were dried ($Na_2SO_4$) and concentrated in vacuo. The crude product was purified by flash column silica gel chromatography (0-100% EtOAc [2% TEA]/hex) to provide the product (0.37 g, 81% yield) as a white solid. $^1$H NMR (400 MHz, $CDCl_3$) δ 8.25 (d, J=7.3 Hz, 1H), 8.09 (d, J=16.8 Hz, 2H), 7.59-7.46 (m, 1H), 7.33 (d, J=7.3 Hz, 1H), 6.71-6.58 (m, 2H), 6.21 (br. s., 1H), 4.72 (br. s., 1H), 4.06 (t, J=13.2 Hz, 1H), 3.96-3.80 (m, 3H), 3.73 (br. s., 1H), 3.68 (s, 3H), 3.64 (dd, J=12.2, 3.1 Hz, 1H), 3.56 (br. s., 2H), 3.01 (d, J=14.6 Hz, 1H), 2.68 (d, J=11.0 Hz, 1H), 2.62 (s, 3H), 2.39 (s, 3H), 2.37 (s, 3H), 1.99 (d, J=13.8 Hz, 1H), 1.90 (d, J=13.1 Hz, 1H), 1.80-1.68 (m, 2H), 1.29 (s, 9H), 1.26 (s, 3H), 1.13 (d, J=6.3 Hz, 3H); LCMS (ESI, M+1): 688.25.

Example 19

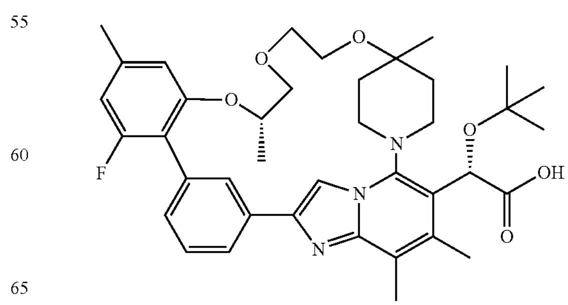

(2S)-2-(tert-Butoxy)-2-((6S,Z)-46-fluoro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetic Acid To a solution of methyl (2S)-2-(tert-butoxy)-2-((6S,Z)-46-fluoro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetate (1.14 g, 1.66 mmol, 1 equiv) in MeOH (15 mL) and THF (1.5 mL) was added 10 N NaOH (1.66 mL, 16.6 mmol, 10 equiv). The reaction was heated at 70° C. for 2 h. Upon cooling to ambient temperature, the crude reaction mixture was purified by C18 chromatography (0-100% MeCN/water) to provide the sodium salt of the product (0.84 g, 70% yield) as a white solid. A minor impurity was also isolated consistant with (2S)-2-(tert-butoxy)-2-((6S,Z)-46-fluoro-28-(hydroxymethyl)-14,27,44,6-tetramethyl-5,8,11-trioxa-2(5,2)-imidazo[1,2-a]pyridina-1(1,4)-piperidina-3(1,3),4(1,2)-dibenzenacycloundecaphane-26-yl)acetic acid (29 mg, 2%). $^{1}$H NMR (400 MHz, DMSO-$d_6$) δ 8.10 (d, J=8.5 Hz, 3H), 7.45 (t, J=7.9 Hz, 1H), 7.20 (d, J=4.5 Hz, 1H), 6.92 (s, 1H), 6.72 (d, J=10.8 Hz, 1H), 5.63 (s, 1H), 4.91 (br. s., 1H), 3.97 (t, J=11.3 Hz, 1H), 3.76-3.51 (m, 7H), 3.46-3.42 (m, 2H), 2.43 (s, 3H), 2.36 (s, 3H), 2.31 (s, 3H), 1.96-1.45 (m, 4H), 1.20 (s, 3H), 1.13 (s, 9H), 0.95 (d, J=6.5 Hz, 3H); LCMS (ESI, M+1): 674.30.

Example 20

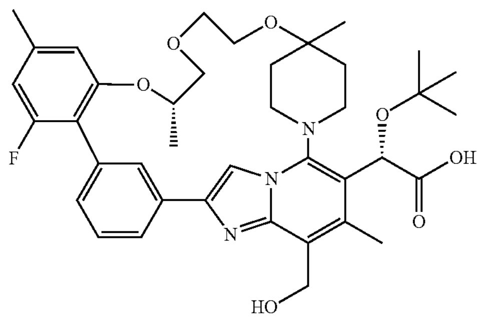 [SMILES: Cc1cc(F)c2c(c1)O[C@@H](C)COCCOC1(C)CCN(CC1)c1c([C@H](OC(C)(C)C)C(=O)O)c(C)c(CO)c3nc(cn13)-c1cccc-2c1]

(2S)-2-(tert-butoxy)-2-((6S,Z)-46-fluoro-28-(hydroxymethyl)-14,27,44,6-tetramethyl-5,8,11-trioxa-2(5,2)-imidazo[1,2-a]pyridina-1(1,4)-piperidina-3(1,3),4(1,2)-dibenzenacycloundecaphane-26-yl)acetic Acid Isolated from preceding reaction as a minor byproduct. LCMS (ESI, M+1): 690.25.

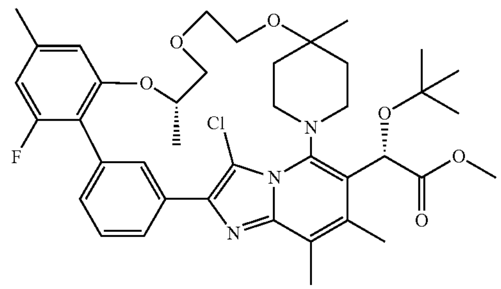 [SMILES: COC(=O)[C@@H](OC(C)(C)C)c1c(C)c(C)c2nc3c(Cl)n2c1N1CCC(C)(CC1)OCCOC[C@H](C)Oc1cc(C)cc(F)c1-c1cccc-3c1]

Methyl (2S)-2-(tert-butoxy)-2-((6S,E)-23-chloro-46-fluoro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetate To a solution of methyl (2S)-2-(tert-butoxy)-2-((6S,Z)-46-fluoro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetate. (1.0 g, 1.45 mmol, 1 equiv) in toluene (73 mL) was added NCS (0.194 g, 1.45 mmol, 1 equiv). After 3 h, the reaction was quenched by addition of tetrahydrothiophene (3 mL). The reaction was diluted with EtOAc and washed with saturated aqueous sodium bicarbonate, dried ($Na_2SO_4$), and concentrated in vacuo. The crude product was purified by flash column silica gel chromatography (0-20% EtOAc/DCM) to provide the product (0.73 g, 70% yield) as an off white solid. $^{1}$H NMR (400 MHz, $CDCl_3$) δ 8.36 (s, 1H), 7.97 (d, J=7.8 Hz, 1H), 7.51 (t, J=7.8 Hz, 1H), 7.39 (d, J=5.5 Hz, 1H), 6.66-6.57 (m, 2H), 6.16 (br. s., 1H), 4.75-4.53 (m, 1H), 4.31-4.06 (m, 3H), 3.70 (s, 3H), 3.87-3.55 (m, 5H), 3.24 (br. s., 1H), 2.60 (s, 3H), 2.53 (br. s., 1H), 2.38 (s, 6H), 1.92 (d, J=10.3 Hz, 2H), 1.79 (br. s., 1H), 1.66 (td, J=13.3, 5.5 Hz, 1H), 1.29 (s, 3H), 1.26 (s, 9H), 1.22 (d, J=6.5 Hz, 3H); LCMS (ESI, M+1): 722.20.

Example 21

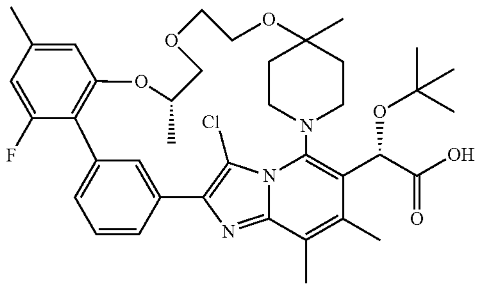 [SMILES: Cc1cc(F)c2c(c1)O[C@@H](C)COCCOC1(C)CCN(CC1)c1c([C@H](OC(C)(C)C)C(=O)O)c(C)c(C)c3nc(c(Cl)n13)-c1cccc-2c1]

Methyl (2S)-2-(tert-butoxy)-2-((6S,E)-23-chloro-46-fluoro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetate To a solution of methyl (2S)-2-(tert-butoxy)-2-((6S,E)-23-chloro-46-fluoro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetate (1.1 g, 1.52 mmol, 1 equiv) in MeOH (10 mL) and THF (5 mL) was added 10 N NaOH (1.5 mL, 15.0 mmol, 10 equiv). The reaction was heated at 60° C. for 2 h. Upon cooling to ambient temperature, the crude reaction mixture was purified by C18 chromatography (5-70% MeCN/water) to provide the sodium salt of the product (1.09 g, 93% yield) as a white solid. $^{1}$H NMR (400 MHz, DMSO-$d_6$) δ 8.28 (s, 1H), 7.87 (d, J=7.8 Hz, 1H), 7.49 (t, J=7.8 Hz, 1H), 7.30 (br. s., 1H), 6.87 (s, 1H), 6.73 (d, J=10.5 Hz, 1H), 5.50 (s, 1H), 4.82-4.64 (m, 1H), 4.15-3.51 (m, 10H), 2.42 (s, 3H), 2.36 (s, 3H), 2.32 (s, 3H), 1.91-1.79 (m, 1H), 1.74-1.64 (m, 1H), 1.62-1.54 (m, 1H), 1.53-1.45 (m, 1H), 1.24 (br. s., 9H), 1.12 (s, 3H), 0.94 (d, J=6.8 Hz, 3H); LCMS (ESI, M+1): 708.20.

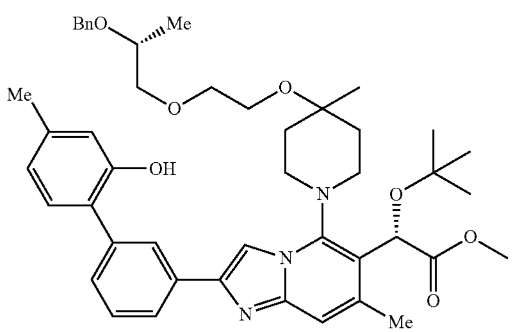 [SMILES: COC(=O)[C@@H](OC(C)(C)C)c1c(C)cc2nc(-c3cccc(-c4ccc(C)cc4O)c3)cn2c1N1CCC(C)(OCCOC[C@@H](C)OCc2ccccc2)CC1]

Methyl (S)-2-(5-(4-(2-((R)-2-(benzyloxy)propoxy)ethoxy)-4-methylpiperidin-1-yl)-2-(2'-hydroxy-4'-methyl-[1,1'-biphenyl]-3-yl)-7-methylimidazo[1,2-a]pyridin-6-yl)-2-(tert-butoxy)acetate To a solution of methyl (S)-2-(5-(4-(2-((R)-2-(benzyloxy)propoxy)ethoxy)-4-methylpiperidin-1-yl)-2-(3-bromophenyl)-7,8-dimethylimidazo[1,2-a]pyridin-6-yl)-2-(tert-butoxy)acetate (0.150 g, 0.204 mmol, 1 equiv), $Pd(OAc)_2$ (5 mg, 0.020 mmol, 0.1 equiv), SPhos (17 mg, 0.041 mmol, 0.2 equiv), and $Cs_2CO_3$ (166 mg, 0.509 mmol, 2.5 equiv) in degassed DMF (1.8 mL) and water (0.18 mL) at 100° C. was added dropwise a solution of 5-methyl-2-(4,4,5,5-tetramethyl-1,3,2-dioxaborolan-2-yl)phenol (71 mg, 0.305 mmol, 1.5 equiv) in DMF (0.5 mL). The orange solution was heated 1 h. After cooling to ambient temperature, the reaction mixture was partitioned between EtOAc and saturated aqueous $NH_4Cl$. The EtOAc layer was dried ($Na_2SO_4$) and concentrated in vacuo. The crude product was puriefied by silica gel flash chromatography (0-100% EtOAc/hexane) to provide to product (146 mg, 93%) as a viscous pale yellow oil. LCMS (ESI, M+1): 764.80.

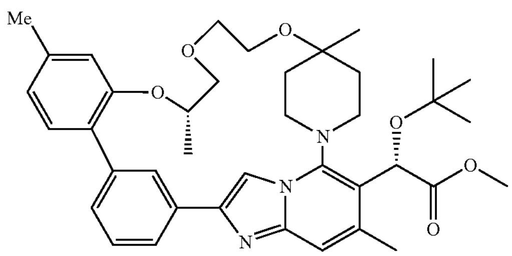 [SMILES: COC(=O)[C@@H](OC(C)(C)C)c1c(C)cc2nc3cn2c1N1CCC(C)(CC1)OCCOC[C@H](C)Oc1cc(C)ccc1-c1cccc-3c1]

Methyl (2S)-2-(tert-butoxy)-2-[(22S)-4,18,22,28-tetramethyl-21,24,27-trioxa-1,7,34-triazahexacyclo$[26.2.2.1^{6,9}.1^{10,14}.0^{2,7}.0^{15,20}]$tetratriaconta-2,4,6(34),8,10(33),11,13,15(20),16,18-decaen-3-yl]acetate To a solution of methyl (S)-2-(5-(4-(2-((R)-2-(benzyloxy)propoxy)ethoxy)-4-methylpiperidin-1-yl)-2-(2'-hydroxy-4'-methyl-[1,1'-biphenyl]-3-yl)-7-methylimidazo[1,2-a]pyridin-6-yl)-2-(tert-butoxy)acetate (145 mg, 0.190 mmol, 1 equiv) and camphorsulfonic acid (44 mg, 0.190 mmol, 1 equiv) in THF (9 mL) was added 10% Pd/C (20 mg, 0.019 mmol, 0.1 equiv). The reaction was then stirred under a balloon of hydrogen for 18 h. Upon completion, the reaction mixture was filtered through Celite eluting with THF. The combined filtrate was concentrate in vacuo. The crude residue was partitioned between saturated aqueous $NaHCO_3$ and EtOAc. The EtOAc layer was dried ($Na_2SO_4$) and concentrated in vacuo to deliver the crude diol (95 mg) as a pale yellow glass. LCMS (ESI, M+1): 674.45. The crude diol was taken up in THF (100 mL). $PPh_3$ (44 mg, 0.169 mmol, 1 equiv) was added followed by dropwise addition of DIAD (0.033 mL, 0.169 mmol, 1 equiv). The reaction turned dark yellow and then slowly lightened. After 1 h, dilute with EtOAc and wash with water. The EtOAc layer was dried ($Na_2SO_4$) and concentrated in vacuo. The crude product was purified by silica gel flash chromatography (0-100% EtOAc/hexane) to give the product (60 mg, 65%) as a pale yellow glass. $^1H$ NMR (500 MHz, $CDCl_3$) δ 8.36 (t, J=1.6 Hz, 1H), 8.18 (dt, J=7.9, 1.3 Hz, 1H), 8.14 (s, 1H), 7.52 (t, J=7.7 Hz, 1H), 7.38-7.32 (m, 3H), 6.91-6.86 (m, 2H), 6.08 (br. s., 1H), 4.80-4.70 (m, 1H), 4.08-3.94 (m, 3H), 3.91-3.83 (m, 1H), 3.75-3.71 (m, 2H), 3.70 (s, 3H), 3.64-3.54 (m, 2H), 3.07 (d, J=9.9 Hz, 1H), 2.69 (d, J=7.9 Hz, 1H), 2.48 (d, J=0.9 Hz, 3H), 2.42 (s, 3H), 2.04-1.98 (m, 1H), 1.92 (dd, J=13.4, 2.0 Hz, 1H), 1.85-1.71 (m, 2H), 1.31 (s, 3H), 1.27 (s, 9H), 1.16 (d, J=6.3 Hz, 3H); LCMS (ESI, M+1): 656.25.

Example 22

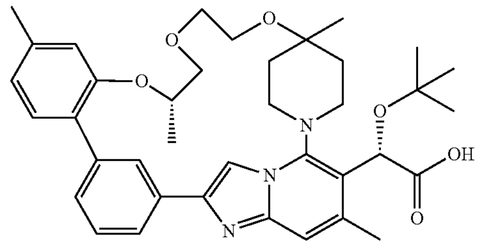 [SMILES: Cc1ccc2c(c1)O[C@@H](C)COCCOC1(C)CCN(CC1)c1c([C@H](OC(C)(C)C)C(=O)O)c(C)cc3nc(cn13)-c1cccc-2c1]

(2S)-2-(tert-Butoxy)-2-[(22S)-4,18,22,28-tetramethyl-21,24,27-trioxa-1,7,34-triazahexacyclo$[26.2.2.1^{6,9}.1^{10,14}.0^{2,7}.0^{15,20}]$tetratriaconta-2,4,6(34),8,10(33),11,13,15(20),16,18-decaen-3-yl]acetic Acid To a solution of methyl (2S)-2-(tert-butoxy)-2-[(22S)-4,18,22,28-tetramethyl-21,24,27-trioxa-1,7,34-triazahexacyclo$[26.2.2.1^{6,9}.1^{10,14}.0^{2,7}.0^{15,20}]$tetratriaconta-2,4,6(34),8,10(33),11,13,15(20),16,18-decaen-3-yl]acetate (10 mg, 0.015 mmol, 1 equiv) in MeOH (1 mL) was added 10 N NaOH (0.05 mL, 0.50 mL, 33 equiv). The reaction was heated at 80° C. for 2 h. After cooling to ambient temperature, the crude reaction was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 20 minutes, then a 5-minute hold at 100% B; Flow: 20 mL/min. Fractions containing the desired product were combined and dried via centrifugal evaporation. The product (6.0 mg, 61%) was isolated. $^1H$ NMR (500 MHz, DMSO-$d_6$) δ 8.38 (s, 1H), 8.11 (s, 1H), 8.05 (d, J=7.7 Hz, 1H), 7.47 (t, J=7.7 Hz, 1H), 7.32-7.26 (m, 2H), 7.20 (s, 1H), 7.01 (s, 1H), 6.84 (d, J=7.7 Hz, 1H), 5.77 (s, 1H), 4.87 (br. s., 1H), 4.00-3.91 (m, 1H), 3.83-3.55 (m, 7H), 3.29 (br. s., 1H), 2.59 (d, J=9.2 Hz, 1H), 2.41 (s, 3H), 2.36 (s, 3H), 1.96 (d, J=12.5 Hz, 1H), 1.81 (d, J=12.5 Hz, 1H), 1.69 (t, J=12.7 Hz, 2H), 1.22 (s, 3H), 1.17 (s, 9H), 1.11 (d, J=6.2 Hz, 3H); LCMS (ESI, M+1): 642.3.

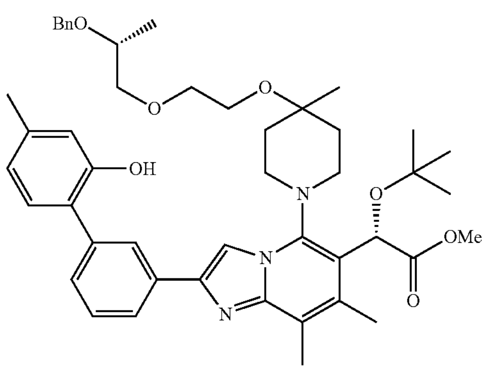 [SMILES: COC(=O)[C@@H](OC(C)(C)C)c1c(C)c(C)c2nc(-c3cccc(-c4ccc(C)cc4O)c3)cn2c1N1CCC(C)(OCCOC[C@@H](C)OCc2ccccc2)CC1]

Methyl (S)-2-(5-(4-(2-((R)-2-(benzyloxy)propoxy)ethoxy)-4-methylpiperidin-1-yl)-2-(2'-hydroxy-4'-methyl-[1,1'-biphenyl]-3-yl)-7,8-dimethylimidazo[1,2-a]pyridin-6-yl)-2-(tert-butoxy)acetate To a solution of methyl (S)-2-(5-(4-(2-((R)-2-(benzyloxy)propoxy)ethoxy)-4-methylpiperidin-1-yl)-2-(3-bromophenyl)-7,8-dimethylimidazo[1,2-a]pyridin-6-yl)-2-(tert-butoxy)acetate (0.40 g, 0.53 mmol, 1 equiv), $Pd(OAc)_2$ (12 mg, 0.053 mmol, 0.1 equiv), SPhos (44 mg, 0.107 mmol, 0.2 equiv), 5-methyl-2-(4,4,5,5-tetramethyl-1,3,2-dioxaborolan-2-yl)phenol (0.25 g, 1.07 mmol, 2 equiv), and 2 M $K_3PO_4$ (1.1 mL, 2.13 mmol, 4 equiv) in degassed dioxane (5 mL) was heated at 85° C. for 2 h. After cooling to ambient temperature, the reaction mixture was partitioned between ether and water. The organic layer was dried ($Na_2SO_4$) and concentrated in vacuo. The crude product was puriefied by silica gel flash chromatography (0-100% EtOAc [2% TEA]/hexane) to provide the product (0.50 g, ~100%). LCMS (ESI, M+1): 778.80.

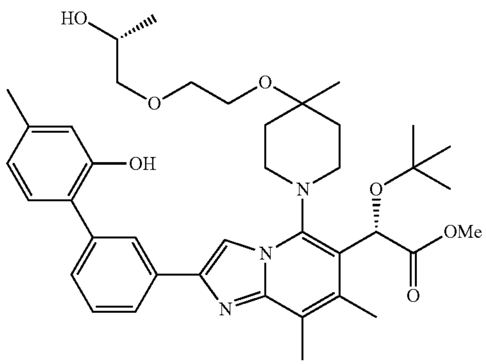 [SMILES: COC(=O)[C@@H](OC(C)(C)C)c1c(C)c(C)c2nc(-c3cccc(-c4ccc(C)cc4O)c3)cn2c1N1CCC(C)(OCCOC[C@@H](C)O)CC1]

Methyl (S)-2-(tert-butoxy)-2-(2-(2'-hydroxy-4'-methyl-[1,1'-biphenyl]-3-yl)-5-(4-(2-((R)-2-hydroxypropoxy)ethoxy)-4-methylpiperidin-1-yl)-7,8-dimethylimidazo[1,2-a]pyridin-6-yl)acetate To a solution of methyl (S)-2-(5-(4-(2-((R)-2-(benzyloxy)propoxy)ethoxy)-4-methylpiperidin-1-yl)-2-(2'-hydroxy-4'-methyl-[1,1'-biphenyl]-3-yl)-7,8-dimethylimidazo[1,2-a]pyridin-6-yl)-2-(tert-butoxy)acetate (500 mg, 0.64 mmol, 1 equiv) and camphorsulfonic acid (0.15 g, 0.64 mmol, 1 equiv) in THF (13 mL) was added 10% Pd/C (0.14 g, 0.129 mmol, 0.2 equiv). The reaction was then stirred under a balloon of hydrogen for 3 h. Upon completion, the reaction mixture was filtered through Celite eluting with THF. The combined filtrate was concentrate in vacuo. The crude residue was partitioned between saturated aqueous $NaHCO_3$ and DCM. The DCM layer was dried ($Na_2SO_4$) and concentrated in vacuo to deliver the crude diol (0.44 g, 100%) as a pale yellow glass. LCMS (ESI, M+1):688.25.

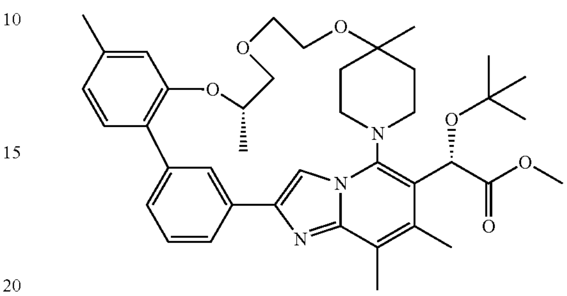

Methyl (2S)-2-(tert-butoxy)-2-((6S,Z)-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetate To a solution of methyl (S)-2-(tert-butoxy)-2-(2-(2'-hydroxy-4'-methyl-[1,1'-biphenyl]-3-yl)-5-(4-(2-((R)-2-hydroxypropoxy)ethoxy)-4-methylpiperidin-1-yl)-7,8-dimethylimidazo[1,2-a]pyridin-6-yl)acetate (0.44 g, 0.64 mmol, 1 equiv) in THF (32 mL) was added $PPh_3$ (0.20 g, 0.77 mmol, 1.2 equiv) was added followed by dropwise addition of DIAD (0.15 mL, 0.77 mmol, 1.2 equiv). After 30 min, dilute with DCM and wash with saturated aqueous sodium bicarbonate. The DCM layer was dried ($Na_2SO_4$) and concentrated in vacuo. The crude product was purified by silica gel flash chromatography (0-100% EtOAc [2% TEA]/hexane) to give the product (0.20 g, 47%). LCMS (ESI, M+1): 670.25.

Example 23

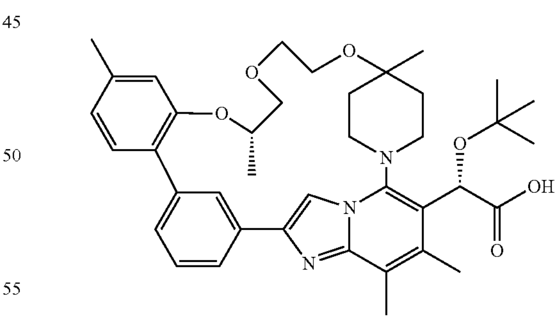

(2S)-2-(tert-Butoxy)-2-((6S,Z)-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetic Acid To a solution of methyl (2S)-2-(tert-Butoxy)-2-((6S,Z)-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetic acid (1.1 g, 1.64 mmol, 1 equiv) in MeOH (11 mL) and THF (5.5 mL) was added 1 N NaOH (8.2 mL, 8.21 mmol, 5 equiv). The reaction was heated to 60° C. and stirred 18 h. Upon cooling to ambient temperature, the reaction mixture was purified by C18 flash chromatograhy (0-100% MeCN/water) to provide the product as the sodium salt (1.05 g, 88%). $^1$H NMR (500 MHz, DMSO-$d_6$) δ 8.35 (s, 1H), 8.11 (d, J=7.9 Hz, 1H), 8.08 (s, 1H), 7.47 (t, J=7.6 Hz, 1H), 7.30 (d, J=7.7 Hz, 1H), 7.27 (d, J=7.7 Hz, 1H), 7.02 (s, 1H), 6.84 (d, J=7.6 Hz, 1H), 5.63 (s, 1H), 4.88 (td, J=6.5, 3.1 Hz, 1H), 3.96 (t, J=10.4 Hz, 1H), 3.83-3.74 (m, 2H), 3.72-3.66 (m, 1H), 3.66-3.55 (m, 4H), 3.52-3.44 (m, 1H), 2.56 (d, J=9.1 Hz, 1H), 2.45 (s, 3H), 2.37 (s, 3H), 2.32 (s, 3H), 1.92 (d, J=12.1 Hz, 1H), 1.83 (d, J=14.0 Hz, 1H), 1.72-1.58 (m, 2H), 1.21 (s, 3H), 1.14 (s, 9H), 1.12 (d, J=6.3 Hz, 3H); LCMS (ESI, M+1: 656.35.

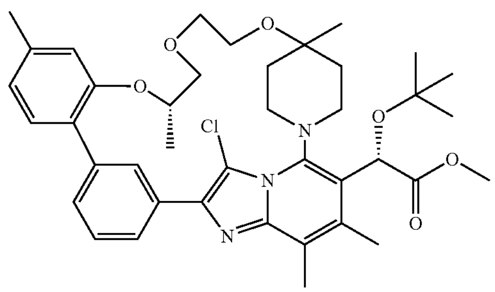 [SMILES: COC(=O)[C@@H](OC(C)(C)C)c1c(C)c(C)c2nc3c(Cl)n2c1N1CCC(C)(CC1)OCCOC[C@H](C)Oc1cc(C)ccc1-c1cccc-3c1]

Methyl (2S)-2-(tert-butoxy)-2-((6S,E)-23-chloro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetate To a solution of methyl (2S)-2-(tert-butoxy)-2-((6S,Z)-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetate (0.58 g, 0.87 mmol, 1 equiv) in toluene (43 mL) was added NCS (116 mg, 0.87 mmol, 1 equiv). After stirring 3 h, the reaction was concentrated in vacuo. The crude product was purified by silica gel flash chromatograhy (0-100% EtOAc/hexane) to provide the product (0.50 g, 82%). LCMS (ESI, M+1): 704.25.

Example 24

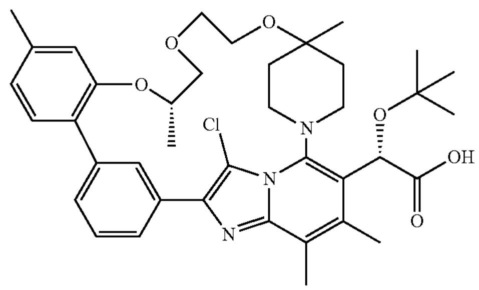 [SMILES: Cc1ccc2c(c1)O[C@@H](C)COCCOC1(C)CCN(CC1)c1c([C@H](OC(C)(C)C)C(=O)O)c(C)c(C)c3nc(c(Cl)n13)-c1cccc-2c1]

(2S)-2-(tert-Butoxy)-2-((6S,E)-23-chloro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetic Acid To a solution of methyl (2S)-2-(tert-butoxy)-2-((6S,E)-23-chloro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetate (0.50 g, 0.71 mmol, 1 equiv) in MeOH (4.7 mL) and THF (2.4 mL) was added 1 N NaOH (3.6 mL, 3.55 mmol, 5 equiv). The reaction was heated to 60° C. and stirred 16 h. Upon cooling to ambient temperature, the reaction mixture was purified by C18 flash chromatograhy (0-100% MeCN/water) to provide the product as the sodium salt (0.40 g, 74%). $^1$H NMR (500 MHz, DMSO-$d_6$) δ 8.63 (t, J=1.6 Hz, 1H), 7.93 (dt, J=7.9, 1.3 Hz, 1H), 7.52 (t, J=7.7 Hz, 1H), 7.34 (dt, J=7.8, 1.4 Hz, 1H), 7.27 (d, J=7.7 Hz, 1H), 7.01 (s, 1H), 6.85 (d, J=7.4 Hz, 1H), 5.54 (s, 1H), 4.79-4.70 (m, 1H), 4.10-4.01 (m, 1H), 4.00-3.92 (m, 1H), 3.89 (d, J=9.9 Hz, 1H), 3.86-3.79 (m, 1H), 3.73-3.68 (m, 1H), 3.67-3.54 (m, 4H), 2.43 (s, 3H), 2.41-2.38 (m, J=5.7 Hz, 1H), 2.38-2.36 (m, 3H), 2.34 (s, 3H), 1.91-1.79 (m, 2H), 1.73-1.64 (m, 1H), 1.62-1.54 (m, 1H), 1.21 (s, 3H), 1.18 (d, J=6.3 Hz, 3H), 1.14 (s, 9H); LCMS (ESI, M+1): 690.25.

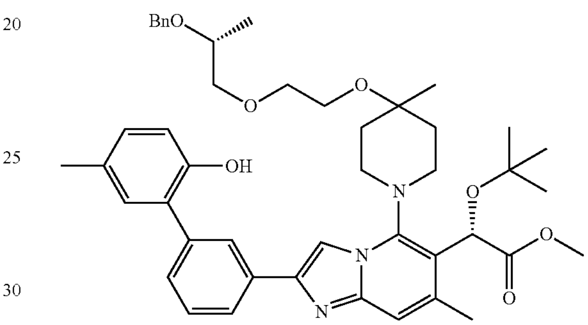

Methyl (S)-2-(5-(4-(2-((R)-2-(benzyloxy)propoxy)ethoxy)-4-methylpiperidin-1-yl)-2-(2'-hydroxy-5'-methyl-[1,1'-biphenyl]-3-yl)-7-methylimidazo[1,2-a]pyridin-6-yl)-2-(tert-butoxy)acetate To a solution of methyl (S)-2-(5-(4-(2-((R)-2-(benzyloxy)propoxy)ethoxy)-4-methylpiperidin-1-yl)-2-(3-bromophenyl)-7-methylimidazo[1,2-a]pyridin-6-yl)-2-(tert-butoxy)acetate (0.15 g, 0.204 mmol, 1 equiv), $Pd(OAc)_2$ (4.5 mg, 0.020 mmol, 0.1 equiv), SPhos (17 mg, 0.041 mmol, 0.2 equiv), and $Cs_2CO_3$ (166 mg, 0.509 mmol, 2.5 equiv) in degassed DMF (1.8 mL) and water (0.18 mL) at 100° C. was added dropwise a solution of (2-hydroxy-5-methylphenyl) boronic acid (62 mg, 0.407 mmol, 2 equiv) in DMF (1 mL). After 5 min, LCMS shows complete conversion. After cooling to ambient temperature, the reaction mixture was partitioned between EtOAc and saturated aqueous $NH_4Cl$. The EtOAc layer was dried ($Na_2SO_4$) and concentrated in vacuo. The crude product was puriefied by silica gel flash chromatography (0-100% EtOAc/hexane) to provide to product (150 mg, 96%) as a white foam. LCMS (ESI, M+1): 764.3.

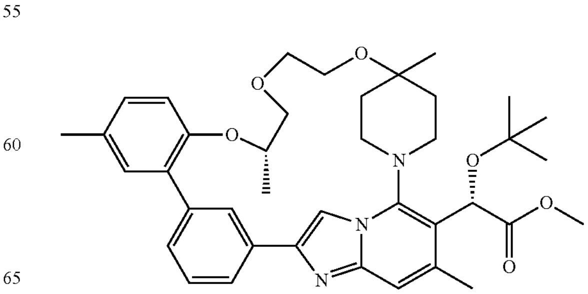

Methyl (2S)-2-(tert-butoxy)-2-[(22S)-4,17,22,28-tetramethyl-21,24,27-trioxa-1,7,34-triazahexacyclo [26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate To a solution of methyl (S)-2-(5-(4-(2-((R)-2-(benzyloxy)propoxy)ethoxy)-4-methylpiperidin-1-yl)-2-(2'-hydroxy-5'-methyl-[1,1'-biphenyl]-3-yl)-7,8-dimethylimidazo[1,2-a]pyridin-6-yl)-2-(tert-butoxy)acetate (150 mg, 0.196 mmol, 1 equiv) and camphorsulfonic acid (46 mg, 0.196 mmol, 1 equiv) in THF (2 mL) was added 10% Pd/C (21 mg, 0.020 mmol, 0.1 equiv). The reaction was then stirred under a balloon of hydrogen for 18 h. Upon completion, the reaction mixture was filtered through Celite eluting with THF. The combined filtrate was concentrate in vacuo. The crude residue was partitioned between saturated aqueous $NaHCO_3$ and EtOAc. The EtOAc layer was dried ($Na_2SO_4$) and concentrated in vacuo to deliver the crude diol. The crude diol was taken up in THF (5 mL). $PPh_3$ (62 mg, 0.235 mmol, 1.2 equiv) was added followed by dropwise addition of DIAD (0.046 mL, 0.235 mmol, 1.2 equiv). After 18 h, dilute with DCM and wash with saturated aqueous $NaHCO_3$. The DCM layer was dried ($Na_2SO_4$) and concentrated in vacuo. The crude product was purified by silica gel flash chromatography (0-100% EtOAc [2% TEA]/hexane) to give the product (120 mg, 65%) as an off white foam. LCMS (ESI, M+1): 656.40.

Example 25

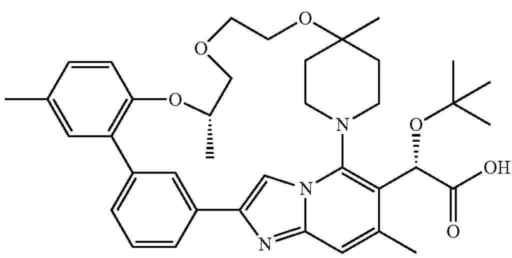 [SMILES: Cc1ccc2c(c1)-c1cccc(c1)-c1cn3c(c([C@H](OC(C)(C)C)C(=O)O)c(C)cc3n1)N1CCC(C)(CC1)OCCOC[C@H](C)O2]

(2S)-2-(tert-Butoxy)-2-[(22S)-4,17,22,28-tetramethyl-21,24,27-trioxa-1,7,34-triazahexacyclo [26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid To a solution of methyl (2S)-2-(tert-butoxy)-2-[(22S)-4,17,22,28-tetramethyl-21,24,27-trioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (6 mg, 0.009 mmol, 1 equiv) in MeOH (0.5 mL), water (0.2 mL), and THF (0.3 mL) was added LiOH (7 mg, 0.279 mmol, 30 equiv). The reaction was heated at 70° C. for 2 h. Upon cooling to ambient temperature, the crude mixture was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 15 minutes, then a 5-minute hold at 100% B; Flow: 20 mL/min. Fractions containing the desired product were combined and dried via centrifugal evaporation. The product (5.0 mg, 83%) was isolated. LCMS (ESI, M+1): 642.2.

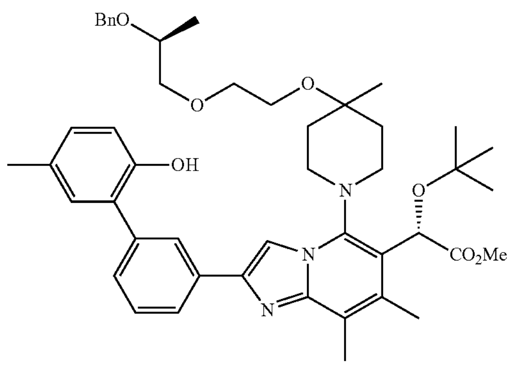 [SMILES: COC(=O)[C@@H](OC(C)(C)C)c1c(C)c(C)c2nc(-c3cccc(-c4cc(C)ccc4O)c3)cn2c1N1CCC(C)(OCCOC[C@H](C)OCc2ccccc2)CC1]

(S)-Methyl 2-(5-(4-(2-((S)-2-(benzyloxy)propoxy)ethoxy)-4-methylpiperidin-1-yl)-2-(2'-hydroxy-5'-methyl-[1,1'-biphenyl]-3-yl)-7,8-dimethylimidazo[1,2-a]pyridin-6-yl)-2-(tert-butoxy)acetate (2-Hydroxy-5-methylphenyl)boronic acid (142 mg, 0.932 mmol) in DMF (1 mL) was added dropwise to a stirring degassed soln of (9-methyl 2-(5-(4-(2-((S)-2-(benzyloxy)propoxy)ethoxy)-4-methylpiperidin-1-yl)-2-(3-bromophenyl)-7,8-dimethylimidazo[1,2-a]pyridin-6-yl)-2-(tert-butoxy)acetate (350 mg, 0.466 mmol), $Pd(OAc)_2$ (10.47 mg, 0.047 mmol), 2-dicyclohexyphosphino-2',6'-dimethoxybiphenyl (38.3 mg, 0.093 mmol), cesium carbonate (456 mg, 1.399 mmol) in DMF (4.238 mL) and Water (0.424 mL) at 100° C. After 1 h, mixture was cooled to room temp and partitioned between water and EtOAc. Organic layer was then dried ($Na_2SO_4$), filtered and concentrated. The residue was then purified by biotage (5-50% EtOAc/hexane) to afford (S)-methyl 2-(5-(4-(2-((S)-2-(benzyloxy)propoxy)ethoxy)-4-methylpiperidin-1-yl)-2-(2'-hydroxy-5'-methyl-[1,1'-biphenyl]-3-yl)-7,8-dimethylimidazo[1,2-a]pyridin-6-yl)-2-(tert-butoxy)acetate (300 mg, 0.386 mmol, 83% yield). $^1$H NMR (500 MHz, $CDCl_3$) δ 8.11 (s, 1H), 8.09-8.02 (m, 2H), 7.53 (t, J=7.6 Hz, 1H), 7.39 (d, J=7.9 Hz, 1H), 7.29 (s, 5H), 7.25-7.21 (m, 1H), 7.14 (s, 1H), 7.05 (d, J=8.2 Hz, 1H), 6.91-6.86 (m, 1H), 6.23 (s, 1H), 4.54-4.44 (m, 2H), 4.02 (t, J=11.1 Hz, 1H), 3.88-3.80 (m, 1H), 3.80-3.76 (m, 2H), 3.69 (s, 3H), 3.63-3.59 (m, 3H), 3.54-3.49 (m, 1H), 3.43 (dd, J=10.2, 4.3 Hz, 1H), 2.98 (d, J=7.7 Hz, 1H), 2.70 (d, J=7.9 Hz, 1H), 2.61 (s, 3H), 2.34 (s, 3H), 1.94 (d, J=13.4 Hz, 2H), 1.83-1.67 (m, 3H), 1.32-1.30 (m, 3H), 1.28 (m, 9H), 1.09 (d, J=6.3 Hz, 3H). LCMS (ESI, M+H)=778.8.

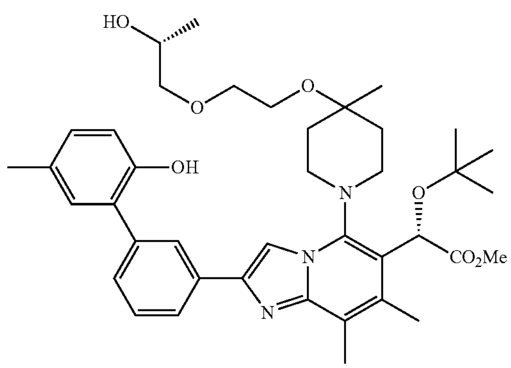 [SMILES: COC(=O)[C@@H](OC(C)(C)C)c1c(C)c(C)c2nc(-c3cccc(-c4cc(C)ccc4O)c3)cn2c1N1CCC(C)(OCCOC[C@@H](C)O)CC1]

(S)-Methyl 2-(tert-butoxy)-2-(2-(2'-hydroxy-5'-methyl-[1,1'-biphenyl]-3-yl)-5-(4-(2-((R)-2-hydroxypropoxy)ethoxy)-4-methylpiperidin-1-yl)-7,8-dimethylimidazo[1,2-a]pyridin-6-yl)acetate To a solution of (9-methyl 2-(5-(4-(2-((R)-2-(benzyloxy)propoxy)ethoxy)-4-methylpiperidin-1-yl)-2-(2'-hydroxy-5'-methyl-[1,1'-biphenyl]-3-yl)-7,8-dimethylimidazo[1,2-a]pyridin-6-yl)-2-(tert-butoxy)acetate (280 mg, 0.360 mmol) in MeOH (10 mL) was added DL-10-camphorsulfonic acid (84 mg, 0.360 mmol) followed by Pd/C (38.3 mg, 0.036 mmol) and the mixture was stirred under balloon hydrogen atmosphere. After 16 h, mixture was filtered and filterate was concentrated, partitioned between EtOAc and bicarb. Organic layer was then dried ($Na_2SO_4$), filtered and concentrated to afford (9-methyl 2-(tert-butoxy)-2-(2-(2'-hydroxy-5'-methyl-[1,1'-biphenyl]-3-yl)-5-(4-(2-((R)-2-hydroxypropoxy)ethoxy)-4-methylpiperidin-1-yl)-7,8-dimethylimidazo[1,2-a]pyridin-6-yl)acetate (240 mg, 0.349 mmol, 97% yield) as off-white solid. $^1$H NMR (500 MHz, $CDCl_3$) δ 8.08 (d, J=7.4 Hz, 2H), 8.04 (d, J=7.7 Hz, 1H), 7.56 (t, J=7.6 Hz, 1H), 7.41 (d, J=7.7 Hz, 1H), 7.19-7.14 (m, 1H), 7.08 (d, J=6.3 Hz, 1H), 6.91 (d, J=8.2 Hz, 1H), 6.20 (s, 1H), 5.89 (br. s., 1H), 4.15 (q, J=7.1 Hz, 2H), 4.02 (t, J=11.0 Hz, 1H), 3.88-3.75 (m, 3H), 3.69 (s, 3H), 3.64-3.60 (m, 2H), 3.45 (dd, J=10.2, 3.0 Hz, 1H), 3.20 (dd, J=10.1, 8.4 Hz, 1H), 3.05-2.98 (m, 1H), 2.75 (br. s., 2H), 2.61 (s, 3H), 2.39 (s, 3H), 2.35 (s, 3H), 1.96 (d, J=13.6 Hz, 2H), 1.84-1.72 (m, 1H), 1.33 (s, 3H), 1.29 (s, 9H), 1.02 (d, J=6.3 Hz, 3H). LCMS (ESI, M+1): 688.7.

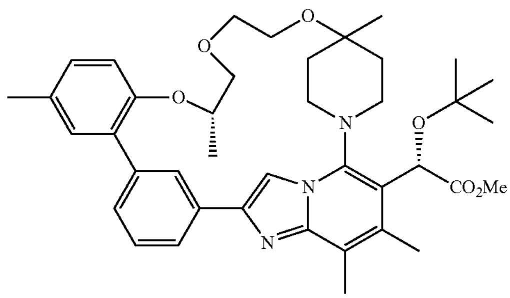 [SMILES: COC(=O)[C@@H](OC(C)(C)C)c1c(C)c(C)c2nc3cn2c1N1CCC(C)(CC1)OCCOC[C@H](C)Oc1ccc(C)cc1-c1cccc-3c1]

Methyl (2S)-2-(tert-butoxy)-2-[(22S)-4,5,17,22,28-pentamethyl-21,24,27-trioxa-1,7,34-triazahexacyclo[26.2.2.$1^{6,9}.1^{10,14}.0^{2,7}.0^{15,20}$]tetratriaconta-2,4,6(34),8,10(33),11,13,15(20),16,18-decaen-3-yl]acetate To a solution of (9-methyl 2-(tert-butoxy)-2-(2-(2'-hydroxy-5'-methyl-[1,1'-biphenyl]-3-yl)-5-(4-(2-((R)-2-hydroxypropoxy)ethoxy)-4-methylpiperidin-1-yl)-7,8-dimethylimidazo[1,2-a]pyridin-6-yl)acetate (240 mg, 0.349 mmol) in THF (100 mL) was added $PPh_3$ (137 mg, 0.523 mmol) followed by DIAD (0.102 mL, 0.523 mmol) and the resulting mixture was stirred at room temp for 16 h. Water was then added and the mixture was extracted with ethyl acetate, dried ($Na_2SO_4$), filtered and concentrated. The residue was then purified by Biotage (5-50% EtOAc/hexane) to afford methyl (2S)-2-(tert-butoxy)-2-[(22S)-4,5,17,22,28-pentamethyl-21,24,27-trioxa-1,7,34-triazahexacyclo[26.2.2.$1^{6,9}.1^{10,14}.0^{2,7}.0^{15,20}$]tetratriaconta-2,4,6(34),8,10(33),11,13,15(20),16,18-decaen-3-yl]acetate (140 mg, 0.209 mmol, 60% yield) as viscous oil. $^1$H NMR (500 MHz, $CDCl_3$) δ 8.32 (s, 1H), 8.25 (d, J=7.7 Hz, 1H), 8.12 (s, 1H), 7.53 (t, J=7.7 Hz, 1H), 7.35 (d, J=7.6 Hz, 1H), 7.27 (d, J=1.7 Hz, 1H), 7.14-7.10 (m, 1H), 6.97 (d, J=8.4 Hz, 1H), 6.22 (br. s., 1H), 4.68 (td, J=6.6, 3.3 Hz, 1H), 4.05 (t, J=11.7 Hz, 1H), 4.00-3.92 (m, 2H), 3.86 (t, J=10.9 Hz, 1H), 3.79-3.73 (m, 2H), 3.71 (d, J=3.3 Hz, 1H), 3.69 (s, 3H), 3.61-3.57 (m, 2H), 3.04 (d, J=8.5 Hz, 1H), 2.70 (d, J=9.5 Hz, 1H), 2.63 (s, 3H), 2.39 (s, 3H), 2.37 (s, 3H), 2.00 (d, J=12.0 Hz, 1H), 1.92 (d, J=14.8 Hz, 1H), 1.82-1.71 (m, 1H), 1.29 (s, 3H), 1.27 (s, 9H), 1.13 (d, J=6.3 Hz, 3H). LCMS (ESI, M+1): 670.45.

Example 26

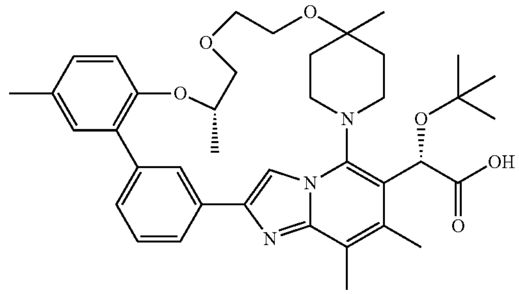 [SMILES: Cc1ccc2c(c1)-c1cccc(c1)-c1cn3c(c([C@H](OC(C)(C)C)C(=O)O)c(C)c(C)c3n1)N1CCC(C)(CC1)OCCOC[C@H](C)O2]

(2S)-2-(tert-Butoxy)-2-[(22S)-4,5,17,22,28-pentamethyl-21,24,27-trioxa-1,7,34-triazahexacyclo[26.2.2.$1^{6,9}.1^{10,14}.0^{2,7}.0^{15,20}$]tetratriaconta-2,4,6(34),8,10(33),11,13,15(20),16,18-decaen-3-yl]acetic Acid To a solution of methyl (2S)-2-(tert-butoxy)-2-[(22S)-4,5,17,22,28-pentamethyl-21,24,27-trioxa-1,7,34-triazahexacyclo[26.2.2.$1^{6,9}.1^{10,14}.0^{2,7}.0^{15,20}$]tetratriaconta-2,4,6(34),8,10(33),11,13,15(20),16,18-decaen-3-yl]acetate (140 mg, 0.209 mmol) in DCM (4 mL) was added NCS (13.95 mg, 0.105 mmol) and the resulting mixture was stirred at room temp for 2 h. Mixture was then diluted with DCM and washed with 0.1 N $Na_2S_2O_3$, dried ($Na_2SO_4$) filtered and concentrated. The residue was then treated with 10 N NaOH (0.209 mL, 2.090 mmol) in THF (20 mL)/MeOH (5 mL) at 70° C. for 5 h. Mixture was then cooled and purified by prep HPLC to afford two compounds, (2S)-2-(tert-butoxy)-2-[(22S)-4,5,17,22,28-pentamethyl-21,24,27-trioxa-1,7,34-triazahexacyclo[26.2.2.$1^{6,9}.1^{10,14}.0^{2,7}.0^{15,20}$]tetratriaconta-2,4,6(34),8,10(33),11,13,15(20),16,18-decaen-3-yl]acetic acid (32 mg, 0.049 mmol, 23% yield) and (2S)-2-(tert-butoxy)-2-[(22S)-8-chloro-4,5,17,22,28-pentamethyl-21,24,27-trioxa-1,7,34-triazahexacyclo-[26.2.2.$1^{6,9}.1^{10,14}.0^{2,7}.0^{15,20}$]tetratriaconta-2,4,6(34),8,10(33),11,13,15(20),16,18-decaen-3-yl]acetic acid (4 mg, 5.79 μmol, 3% yield). LCMS (M+H)=656.3

Example 27

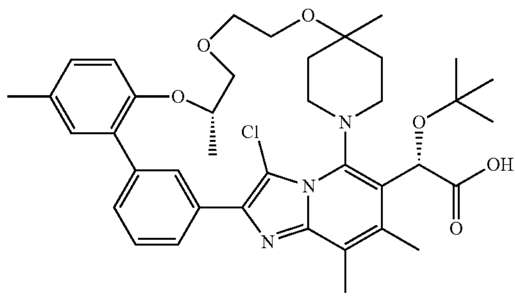 [SMILES: Cc1ccc2c(c1)-c1cccc(c1)-c1nc3c(C)c(C)c([C@H](OC(C)(C)C)C(=O)O)c(n3c1Cl)N1CCC(C)(CC1)OCCOC[C@H](C)O2]

(2S)-2-(tert-Butoxy)-2-[(22S)-8-chloro-4,5,17,22,28-pentamethyl-21,24,27-trioxa-1,7,34-triazahexacyclo [26.2.2.$1^{6,9}$.$1^{10,14}$.$0^{2,7}$.$0^{15,20}$]tetratriaconta-2,4,6(34),8,10(33),11,13,15(20),16,18-decaen-3-yl]acetic Acid Isolated from the same reaction as the previous compound. LCMS (M+H)=690.2.

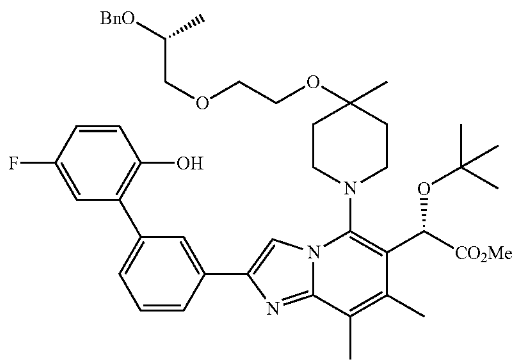 [SMILES: COC(=O)[C@@H](OC(C)(C)C)c1c(C)c(C)c2nc(-c3cccc(-c4cc(F)ccc4O)c3)cn2c1N1CCC(C)(OCCOC[C@@H](C)OCc2ccccc2)CC1]

Methyl (S)-2-(5-(4-(2-((R)-2-(benzyloxy)propoxy)ethoxy)-4-methylpiperidin-1-yl)-2-(5'-fluoro-2'-hydroxy-[1,1'-biphenyl]-3-yl)-7,8-dimethylimidazo[1,2-a]pyridin-6-yl)-2-(tert-butoxy)acetate A solution of (9-methyl 2-(5-(4-(2-((R)-2-(benzyloxy)propoxy)ethoxy)-4-methylpiperidin-1-yl)-2-(3-bromophenyl)-7,8-dimethylimidazo[1,2-a]pyridin-6-yl)-2-(tert-butoxy)acetate (0.40 g, 0.53 mmol, 1 equiv), 4-fluoro-2-(4,4,5,5-tetramethyl-1,3,2-dioxaborolan-2-yl)phenol (254 mg, 1.07 mmol, 2 equiv), $Pd(OAc)_2$ (12 mg, 0.053 mmol, 0.1 equiv), SPhos (44 mg, 0.107 mmol, 0.2 equiv), and 2 M $K_3PO_4$ (1.1 mL, 2.13 mmol, 4 equiv) in degassed dioxane (5 mL) was heated at 85° C. for 2 h. After cooling to ambient temperature, the reaction mixture was partitioned between ether and water. The ether layer was dried ($Na_2SO_4$) and concentrated in vacuo. The crude product was purified by silica gel flash chromatography (0-100% EtOAc [2% TEA]/hexane) to provide to product (0.41 g, 98%). LCMS (ESI, M+1)=782.40.

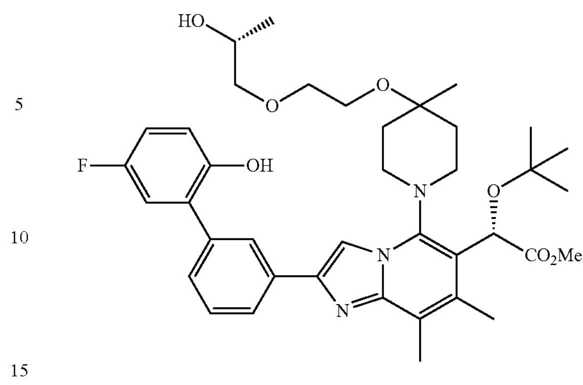

Methyl (S)-2-(tert-butoxy)-2-(2-(5'-fluoro-2'-hydroxy-[1,1'-biphenyl]-3-yl)-5-(4-(2-((R)-2-hydroxypropoxy)ethoxy)-4-methylpiperidin-1-yl)-7,8-dimethylimidazo[1,2-a]pyridin-6-yl)acetate To a solution of methyl (S)-2-(5-(4-(2-((R)-2-(benzyloxy)propoxy)ethoxy)-4-methylpiperidin-1-yl)-2-(5'-fluoro-2'-hydroxy-[1,1'-biphenyl]-3-yl)-7,8-dimethylimidazo[1,2-a]pyridin-6-yl)-2-(tert-butoxy)acetate (0.40 g, 0.51 mmol, 1 equiv) and camphorsulfonic acid (0.12 g, 0.51 mmol, 1 equiv) in THF (10 mL) was added 10% Pd/C (54 mg, 0.051 mmol, 0.1 equiv). The reaction was put under a balloon of hydrogen. After 18 h, the reaction was filtered through celite and the filtrate was concentrated in vacuo. The crude product was diluted with EtOAc and washed with saturated aqueous sodium bicarbonate. The EtOAc layer was dried ($Na_2SO_4$) and concentrated in vacuo to provide the product (0.26 g, 74% yield). LCMS (ESI, M+1): 692.20.

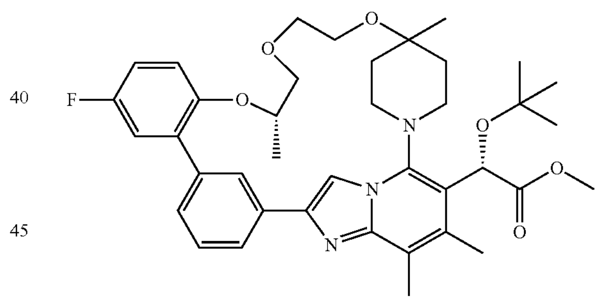

Methyl (2S)-2-(tert-butoxy)-2-((6S,Z)-45-fluoro-14,27,28,6-tetramethyl-5,8,11-trioxa-2(5,2)-imidazo[1,2-a]pyridina-1(1,4)-piperidina-3(1,3),4(1,2)-dibenzenacycloundecaphane-26-yl)acetate To a solution of (9-methyl 2-(tert-butoxy)-2-(2-(5'-fluoro-2'-hydroxy-[1,1'-biphenyl]-3-yl)-5-(4-(2-((R)-2-hydroxypropoxy)ethoxy)-4-methylpiperidin-1-yl)-7,8-dimethylimidazo[1,2-a]pyridin-6-yl)acetate (0.25 g, 0.376 mmol, 1 equiv) and $PPh_3$ (0.12 g, 0.45 mmol, 1.2 equiv) in THF (8 mL) was added DIAD (0.088 mL, 0.45 mmol, 1.2 equiv). After 18 h, the reaction was diluted with EtOAc and washed with saturated aqueous sodium bicarbonate. The EtOAc layer was dried ($Na_2SO_4$) and concentrated in vacuo. The crude product was purified by flash column silica gel chromatography (0-100% EtOAc [2% TEA]/hex) to provide the product (0.15 g, 59% yield) as an off white solid. LCMS (ESI, M+1): 674.55.

Example 28

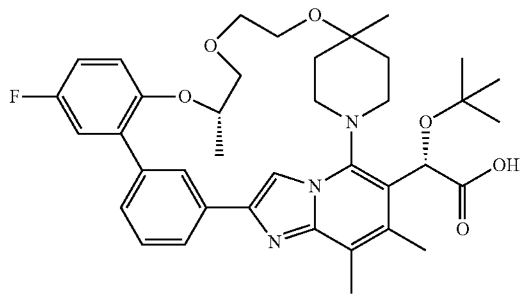 [SMILES: Cc1c([C@H](OC(C)(C)C)C(=O)O)c2n3cc(nc3c1C)-c1cccc(c1)-c1cc(F)ccc1O[C@@H](C)COCCOC1(C)CCN2CC1]

(2S)-2-(tert-Butoxy)-2-((6S,Z)-45-fluoro-14,27,28,6-tetramethyl-5,8,11-trioxa-2(5,2)-imidazo[1,2-a]pyridina-1(1,4)-piperidina-3(1,3),4(1,2)-dibenzenacycloundecaphane-26-yl)acetic Acid To a solution of methyl (2S)-2-(tert-butoxy)-2-((6S,Z)-45-fluoro-14,27,28,6-tetramethyl-5,8,11-trioxa-2(5,2)-imidazo[1,2-a]pyridina-1(1,4)-piperidina-3(1,3),4(1,2)-dibenzenacycloundecaphane-26-yl)acetate (60 mg, 0.089 mmol, 1 equiv) in MeOH (0.9 mL), water (0.3 mL) and THF (0.6 mL) was added 8 N NaOH (0.33 mL, 0.267 mmol, 30 equiv). The reaction was heated at 60° C. for 2 h. Upon cooling to ambient temperature, the crude reaction mixture was purified via C18 chromatography (5-70% MeCN/water) to provide the product (57 mg, 98% yield) as a white solid. $^1$H NMR (400 MHz, $CDCl_3$) δ 8.33 (s, 1H), 8.24 (d, J=7.5 Hz, 1H), 8.10 (s, 1H), 7.52 (t, J=7.8 Hz, 1H), 7.31 (d, J=8.0 Hz, 1H), 7.18 (d, J=2.0 Hz, 1H), 7.01-6.94 (m, 2H), 6.08 (br. s., 1H), 4.60 (br. s., 1H), 4.20-3.36 (m, 9H), 2.69 (d, J=8.5 Hz, 1H), 2.57 (br. s., 3H), 2.25 (br. s., 3H), 1.96-1.83 (m, 2H), 1.68 (br. s., 2H), 1.21 (s, 3H), 1.14-1.02 (m, 12H); LCMS (ESI, M+1): 760.20.

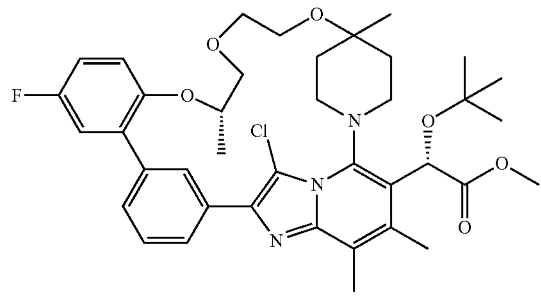 [SMILES: COC(=O)[C@@H](OC(C)(C)C)c1c(C)c(C)c2nc3c(Cl)n2c1N1CCC(C)(CC1)OCCOC[C@H](C)Oc1ccc(F)cc1-c1cccc-3c1]

Methyl (2S)-2-(tert-butoxy)-2-((6S,E)-23-chloro-45-fluoro-14,27,28,6-tetramethyl-5,8,11-trioxa-2(5,2)-imidazo[1,2-a]pyridina-1(1,4)-piperidina-3(1,3),4(1,2)-dibenzenacycloundecaphane-26-yl)acetate To a solution of methyl (2S)-2-(tert-butoxy)-2-((6S,Z)-45-fluoro-14,27,28,6-tetramethyl-5,8,11-trioxa-2(5,2)-imidazo[1,2-a]pyridina-1(1,4)-piperidina-3(1,3),4(1,2)-dibenzenacycloundecaphane-26-yl)acetate (50 mg, 0.074 mmol, 1 equiv) in DCM (10 mL) was added a solution of NCS (10 mg, 0.074 mmol, 1 equiv) in DCM (5 mL). After 1 h, the reaction was diluted with DCM and washed with 0.1 N $Na_2S_2O_3$. The DCM layer was dried ($Na_2SO_4$) and concentrated in vacuo. The crude product was purified by silica gel flash chromatography (0-100% EtOAc/hexane) to provide the product (20 mg, 38%). LCMS (ESI, M+1): 708.15.

Example 29

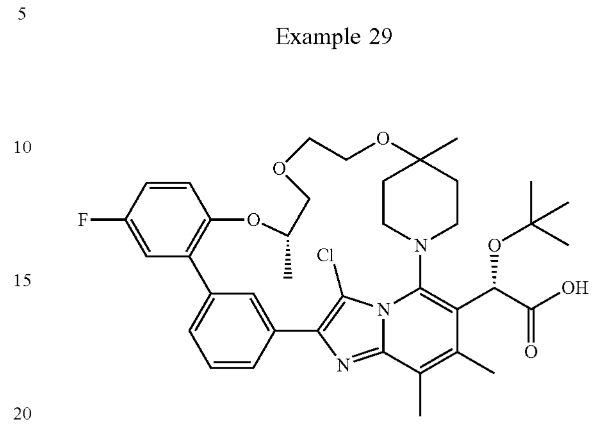

(2S)-2-(tert-butoxy)-2-((6S,E)-23-chloro-45-fluoro-14,27,28,6-tetramethyl-5,8,11-trioxa-2(5,2)-imidazo[1,2-a]pyridina-1(1,4)-piperidina-3(1,3),4(1,2)-dibenzenacycloundecaphane-26-yl)acetic Acid To a solution of methyl (2S)-2-(tert-butoxy)-2-((6S,E)-23-chloro-46-fluoro-14,27,28,44,6-pentamethyl-5,8,11-trioxa-2(5,2)-imidazo[1,2-a]pyridina-1(1,4)-piperidina-3(1,3),4(1,2)-dibenzenacycloundecaphane-26-yl)acetate (20 mg, 0.028 mmol, 1 equiv) in MeOH (0.3 mL), water (0.1 mL) and THF (0.2 mL) was added 8 N NaOH (0.106 mL, 0.847 mmol, 30 equiv). The reaction was heated at 60° C. for 2 h. Upon cooling to ambient temperature, the crude reaction mixture was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 15 minutes, then a 5-minute hold at 100% B; Flow: 20 mL/min. Fractions containing the desired product were combined and dried via centrifugal evaporation to provide the product (4.1 mg, 20% yield) as a white solid. $^1$H NMR (500 MHz, DMSO-$d_6$) δ 8.67 (s, 1H), 7.98 (d, J=7.7 Hz, 1H), 7.57 (t, J=7.7 Hz, 1H), 7.44 (d, J=7.7 Hz, 1H), 7.31-7.11 (m, 3H), 5.92 (br. s., 1H), 4.76-4.56 (m, 1H), 4.05 (br. s., 1H), 3.95 (t, J=10.8 Hz, 1H), 3.87 (d, J=10.6 Hz, 1H), 3.71-3.65 (m, 1H), 3.64-3.52 (m, 3H), 2.49 (s, 3H), 2.47-2.42 (m, J=5.1 Hz, 3H), 2.33 (s, 3H), 1.86 (d, J=12.5 Hz, 2H), 1.74 (br. s., 1H), 1.61 (d, J=4.4 Hz, 1H), 1.21 (s, 3H), 1.18 (s, 9H), 1.14 (d, J=6.2 Hz, 3H); LCMS (ESI, M+1): 694.20.

Biological Methods

Inhibition of HIV Replication:

A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC18 at the PvuII site. The NL-RLuc virus was prepared by transfection of 293T cells with the plasmid pNLRLuc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/\text{drug conc.})^m]$ (Johnson V A, Byington R T. Infectivity Assay. In Techniques in HIV Research. ed. Aldovini A, Walker B D. 71-76. New York: Stockton Press. 1990). Results are shown in Table 1. Activity equal to A refers to a compound having an $EC_{50}\leq 100$ nM, while B and C denote compounds having an $EC_{50}$ between 100 nM and luM (B) or >1 uM (C).

TABLE 1

| Example | Activity | $EC_{50}$ μM |
|---|---|---|
| 1 | A | 0.001 |
| 2 | A | |
| 3 | B | 0.305 |
| 4 | A | |
| 5 | B | 0.283 |
| 6 | A | 0.002 |
| 7 | A | |
| 8 | A | |
| 9 | A | |
| 10 | A | 0.005 |
| 11 | A | |
| 12 | A | 0.012 |
| 13 | A | |
| 14 | A | |
| 15 | A | |
| 16 | A | 0.002 |
| 17 | A | |
| 18 | A | |
| 19 | A | |
| 20 | ND | ND |
| 21 | A | 0.002 |
| 22 | A | |
| 23 | A | |
| 24 | A | |
| 25 | A | 0.002 |
| 26 | A | |
| 27 | A | |
| 28 | A | |
| 29 | A | 0.001 |

ND = Not determined

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I

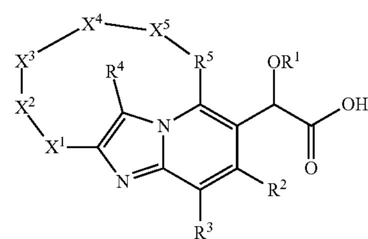

wherein:

$R^1$ is alkyl;

$R^2$ is alkyl;

$R^3$ is selected from hydrogen, cyano, halo, alkyl, hydroxyalkyl, alkoxyalkyl, $(Ar^1)$alkyl, or alkenyl;

$R^4$ is selected from hydrogen, halo, or alkyl;

$R^5$ is piperidinyl substituted with 0-3 substituents selected from halo, alkyl, haloalkyl, hydroxy, alkoxy, and haloalkoxy;

$Ar^1$ is selected from pyrazolyl or triazolyl;

$X^1$ is phenyl substituted with 0-3 substituents selected from cyano, halo, alkyl, haloalkyl, alkoxy, and haloalkoxy;

$X^2$ is phenyl substituted with 0-3 substituents selected from cyano, halo, alkyl, haloalkyl, alkoxy, and haloalkoxy;

$X^3$ is —O—;

$X^4$ is alkyleneoxyalkylene; and $X^5$ is —O—;

or a pharmaceutically acceptable salt thereof.

2. A compound or salt of claim 1 wherein $R^3$ is selected from cyano, hydroxyalkyl, alkoxyalkyl, $(Ar^1)$alkyl, or alkenyl.

3. A compound or salt of claim 1 wherein $R^4$ is selected from hydrogen or halo.

4. A pharmaceutical composition comprising a compound or salt of claim 1.

5. The composition of claim 4 further comprising at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

6. The composition of claim 5 wherein the other agent is dolutegravir.

7. A method for treating HIV infection comprising administering a compound of claim 1, or a pharmaceutically acceptable salt thereof, to a patient in need thereof.

8. The method of claim 7 further comprising administering at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

9. The method of claim 8 wherein the other agent is dolutegravir.

* * * * *